United States Patent [19]

Zbinden

[11] Patent Number: 5,688,815
[45] Date of Patent: Nov. 18, 1997

[54] HYDROXYPYRIDINONES

[75] Inventor: Paul Zbinden, Witterswil, Switzerland

[73] Assignee: Ciba Geigy Corporation, Summit, N.J.

[21] Appl. No.: 722,820

[22] Filed: Sep. 27, 1996

[30] Foreign Application Priority Data

Sep. 29, 1995 [CH] Switzerland .............. 2759/95

[51] Int. Cl.$^6$ .............. A61K 31/44; C07D 211/94
[52] U.S. Cl. .............. 514/348; 546/296
[58] Field of Search .............. 514/348; 546/296

[56] References Cited

U.S. PATENT DOCUMENTS

| | | | |
|---|---|---|---|
| 4,980,371 | 12/1990 | Parker et al. | 514/461 |
| 5,112,968 | 5/1992 | Treuner | 540/355 |
| 5,256,676 | 10/1993 | Hider et al. | 514/348 |

FOREIGN PATENT DOCUMENTS

| | | |
|---|---|---|
| 0316279 | 5/1989 | European Pat. Off. . |
| 0335745 | 10/1989 | European Pat. Off. . |
| 0494754 | 7/1992 | European Pat. Off. . |
| 2118176 | 10/1983 | United Kingdom . |
| 2136807 | 9/1984 | United Kingdom . |
| 2269589 | 2/1994 | United Kingdom . |

*Primary Examiner*—C. Warren Ivy
*Assistant Examiner*—D. Margaret M. Mach
*Attorney, Agent, or Firm*—Marla J. Mathias

[57] ABSTRACT

Described are 3-hydroxypyridin-4-ones of formula I

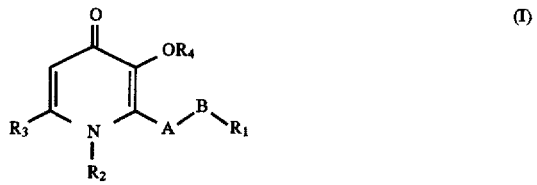

wherein $R_1-R_4$, A and B are as defined in the description. The compounds have valuable pharmaceutical properties and are especially effective as chelators of iron. They can be used to treat excess iron in the bodies of warm-blooded animals.

10 Claims, No Drawings

HYDROXYPYRIDINONES

The invention relates to compounds of formula I

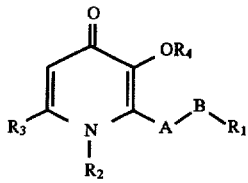

wherein:

- $R_1$ is hydrogen, halogen, substituted or unsubstituted lower alkyl or lower alkoxy, lower alkoxycarbonyl, amino, substituted or unsubstituted lower alkylamino or di-lower alkylamino, aminocarbonyl, substituted or unsubstituted N-lower alkylaminocarbonyl or N,N-di-lower alkylaminocarbonyl, carboxyl, lower alkylsulfonyl, aminosulfonyl, cyano, hydroxy, nitro, tetrazolyl, or lower alkylenedioxy which with the group B forms a heterocyclic oxygen-containing ring system;
- $R_2$ is hydrogen, substituted or unsubstituted lower alkyl or lower alkylenehydroxy, substituted or unsubstituted lower alkylene-lower alkoxy, lower alkylenecarboxy, lower alkylenecarbonyl-lower alkoxy, substituted or unsubstituted lower alkyleneamine, substituted or unsubstituted N-lower alkanoyl-lower alkyleneamine, lower alkanoyloxy-lower alkylene, formyl-lower alkylene, or $R_2$ together with A and the atoms to which they are bonded forms a substituted or unsubstituted oxygen-containing heterocyclic ring or $R_2$ together with $R_3$ and the atoms to which they are bonded forms a substituted or unsubstituted oxygen-containing heterocyclic ring;
- $R_3$ is hydrogen, substituted or unsubstituted lower alkyl, carboxyl, substituted or unsubstituted lower alkanoyloxy-lower alkylene, aminocarbonyl, substituted or unsubstituted N-lower alkylaminocarbonyl, N,N-di-lower alkylaminocarbonyl, or $R_3$ together with $R_2$ and the atoms to which they are bonded forms a substituted or unsubstituted oxygen-containing heterocyclic ring;
- $R_4$ is hydrogen, lower alkanoyl, lower alkoxycarbonyl, or a radical that can be removed under physiological conditions;
- A is substituted or unsubstituted methylene, carbonyl, or A together with $R_2$ and the atoms to which they are bonded forms a substituted or unsubstituted oxygen-containing heterocyclic ring; and
- B is mono- or poly-substituted or unsubstituted aryl or mono- or poly-substituted or unsubstituted heteroaryl;

and to the stereoisomers, tautomers and salts thereof, especially pharmaceutically acceptable salts thereof; to processes for the preparation of those compounds, to pharmaceutical compositions comprising those compounds and to the use of those compounds in the therapeutic treatment of the human or animal body or in the preparation of pharmaceutical compositions.

Within the scope of the present Application, the general terms used hereinbefore and hereinafter preferably have the following definitions:

Halogen is, for example, chlorine, bromine or fluorine, but may also be iodine.

The prefix "lower" denotes a radical having up to and including 7, and especially up to and including 4, carbon atoms.

Alkyl and alkylene are straight-chained or branched. On their own, for example lower alkyl, or as constituents of other groups, for example lower alkoxy, lower alkylamine, lower alkyl-aminocarbonyl, lower alkylenehydroxy, they may be unsubstituted or substituted, for example, by halogen, hydroxy or by trifluoromethyl; they are preferably unsubstituted or substituted by hydroxy.

Methylene may be unsubstituted or substituted, for example, by lower alkyl, halogen or by hydroxy; it is preferably unsubstituted or substituted by hydroxy.

Lower alkyl is, for example n-propyl, isopropyl, n-butyl, isobutyl, see-butyl, tert-butyl, n-pentyl, neopentyl, n-hexyl or n-heptyl, preferably methyl, ethyl and n-propyl.

Lower alkoxy is, for example, n-propoxy, isopropoxy, n-butoxy, isobutoxy, sec-butoxy, tert-butoxy, n-amyloxy, isoamyloxy, preferably methoxy and ethoxy. Lower alkoxycarbonyl is, for example, lower alkyl—O—C(O)—, for example n-propoxycarbonyl, isopropoxycarbonyl, n-butoxycarbonyl, se-butoxycarbonyl, tert-butoxycarbonyl, preferably methoxycarbonyl and ethoxycarbonyl.

Lower alkylamino is, for example, n-propylamino, n-butylamino, iso-propylamino, iso-butylamino, preferably methylamino and ethylamino.

Di-lower alkylamino is, for example, dimethylamino, diethylamino, di-n-propylamino, n-butylamino, di-n-butylamino, n-propyl-n-butylamino, preferably dimethylamino, diethylamino and methylethylamino.

Aminocarbonyl denotes the carbamoyl radical

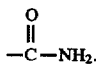

N-Lower alkylaminocarbonyl is, for example, N-methylcarbamoyl, N-ethylcarbamoyl, N-n-propylcarbamoyl, N-isopropylcarbamoyl, preferably N-methylcarbamoyl and N-ethylcarbamoyl.

N,N-Di-lower alkylaminocarbonyl is, for example, N,N-dimethylcarbamoyl, N,N-diethylcarbamoyl, N-methyl-N-ethylcarbamoyl, N,N-di-n-propylcarbamoyl, N-methyl-N-isopropylcarbamoyl, preferably N,N-dimethylcarbamoyl, N,N-diethylcarbamoyl and N-methyl-N-ethyl-carbamoyl.

Lower alkylene on its own or as a constituent of other groups, such as lower alkylenedioxy, lower alkylenehydroxy, lower alkyleneamine, lower alkylenecarboxy, lower alkanoyloxy-lower alkylene, is the group —$(CH_2)_n$—, wherein n is a natural number from 1 to 7 inclusive, preferably from 1 to 4 inclusive, and is, for example, methylene, 1,2-ethylene, 1,3-propylene or 1,4-butylene.

Lower alkylenedioxy is the group —O—$(CH_2)_n$—O—, wherein n is a natural number from 1 to 7 inclusive, and is, for example, methylenedioxy, 1,2-ethylenedioxy, 1,3-n-propylenedioxy, preferably methylenedioxy and 1,2-ethylenedioxy.

Lower alkylenehydroxy is the group —$(CH_2)_n$—OH, wherein n is a natural number from 1 to 7 inclusive, preferably from 1 to 4 inclusive, and is, for example, methylenehydroxy, ethylenehydroxy, propylenehtdroxy, but especially ethylenehydroxy and propylenecarboxy.

Lower alkylene-lower alkoxy is lower alkylenehydroxy etherified by lower alkyl, for example methoxymethylene, methoxyethylene, ethoxymethylene, ethoxyethylene, especially ethoxyethylene, while lower alkanoyloxy-lower alkylene is lower alkylenehydroxy esterified by lower alkanoyl, for example acetoxyethylene or acetoxypropylene, preferably acetoxyethylene.

Lower alkylenecarboxy is the group

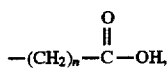

wherein n is a natural number from 1 to 7 inclusive, preferably from 1 to 4 inclusive, and is, for example, methylenecarboxy, ethylenecarboxy, propylenecarboxy, butylenecarboxy, especially methylenecarboxy, ethylenecarboxy or propylenecarboxy, while lower alkylenecarbonyl-lower alkoxy is lower alkylenecarboxy esterified by lower alkyl, for example ethylenecarboxylic acid methyl ester, ethylenecarboxylic acid ethyl ester, propylenecarboxylic acid methyl ester, propylenecarboxylic acid ethyl ester, butylenecarboxylic acid methyl ester or butylenecarboxylic acid ethyl ester, especially ethylenecarboxylic acid ethyl ester, propylenecarboxylic acid ethyl ester or butylenecarboxylic acid ethyl ester.

Lower alkyleneamine is the group —(CH$_2$)$_n$—NH$_2$, wherein n is a natural number from 1 to 7 inclusive, preferably from 1 to 4 inclusive, and is, for example, methyleneamine, ethyleneamine, propyleneamine or butyleneamine, but also radicals wherein one or two hydrogens at the nitrogen have been replaced by lower alkyl, preferably N-methyl-lower alkyleneamine, N,N-dimethyl-lower alkyleneamine, N-ethyl-lower alkyleneamine, N,N-di-lower alkyleneamine or N-methyl-N-ethyl-lower alkyleneamine.

In the radical N-lower alkanoyl-lower alkyleneamine, one of the hydrogens of the lower alkyleneamine that are bonded to the nitrogen has been replaced by a lower alkanoyl radical, for example acetamidoethylene or acetamidopropylene, especially acetamidoethylene.

Lower alkanoyl is, for example, acetyl, propanoyl or butanoyl, but also formyl.

Formyl-lower alkylene is the group

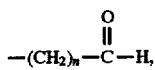

wherein n is a natural number from 1 to 7 inclusive, preferably from 1 to 4 inclusive, and is, for example, ethylenealdehyde, propylenealdehyde or butylenealdehyde, especially ethylenealdehyde.

Lower alkoxycarbonyl is the group

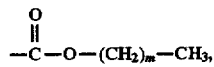

wherein m is a natural number from 0 to 6 inclusive, preferably from 0 to 3 inclusive, and is especially methyloxycarbonyl.

Oxygen-containing heterocyclic rings are saturated or unsaturated rings having from five up to and including seven ring members of which at least one is oxygen and in which one or more further hetero atoms, for example nitrogen, may be present, for example dioxolane, dioxane, oxazole, oxazine; optionally, one or more ring carbon atoms may also have been oxidised to carbonyl as, for example, in dioxanone, oxazolone, oxazinone. They may be unsubstituted or substituted, especially unsubstituted or substituted by lower alkyl, lower alkoxy or by hydroxy.

Aryl is, for example, phenyl or naphthyl that is substituted or unsubstituted. Aryl is preferably phenyl that is unsubstituted or substituted by one or more, especially one or two, substituents, for example lower alkyl, lower alkoxy, hydroxy, nitro, amino, halogen, trifluoromethyl, carboxy, amino or cyano. Aryl is especially unsubstituted phenyl or naphthyl, or phenyl that is substituted by lower alkyl, lower alkoxy, hydroxy, halogen or by trifluoromethyl.

Heteroaryl is an aromatic radical having from 3 up to and including 7, especially from 5 up to and including 7, ring atoms, wherein at least one of the ring atoms is a hetero atom, for example pyrrolyl, furanyl, thiophenyl, pyridyl, pyranyl, pyrimidinyl. Preference is given to azaheteroaryl, that is to say at least one of the ring atoms is a nitrogen atom. Azaheteroaryl may contain further ring hetero atoms, for example nitrogen, oxygen or sulfur, and is, for example, pyrrolyl, pyridyl, pyrimidinyl or pyrazinyl. Heteroaryl may be substituted or unsubstituted. Preference is given to heteroaryl that is unsubstituted or substituted by one or more, especially one or two, substituents, for example lower alkyl, halogen or trifluoromethyl. Heteroaryl is especially unsubstituted pyridyl.

Radicals such as pyrrolyl, pyridyl, pyrimidinyl and pyrazinyl may be bonded via a ring nitrogen atom or a ring carbon atom; radicals such as pyridyl or pyrimidinyl are preferably bonded via a carbon atom.

Salts of compounds of formula I are especially pharmaceutically acceptable salts, especially salts with bases, such as corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, mono-, di- or tri-lower alkylamines, hydroxy-lower alkylamines, for example mono-, di- or tri-hydroxy-lower alkylamines, hydroxy-lower alkyl-lower alkyl-amines or polyhydroxy-lower alkylamines. Cyclic amines are, for example, morpholine, thiomorpholine, piperidine or pyrrolidine. Suitable mono-lower alkylamines are, for example, ethyl- and tert-butyl-amine; suitable di-lower alkylamines are, for example, diethyl- and diisopropyl-amine and suitable tri-lower alkylamines are, for example, trimethyl- and triethyl-amine. Suitable hydroxy-lower alkylamines are, for example, mono-, di- and tri-ethanolamine; suitable hydroxy-lower alkyl-lower alkyl-amines are, for example, N,N-dimethylamino- and N,N-diethylamino-ethanol, and there is suitable as polyhydroxy-lower alkylamine, for example, glucosamine. In other cases, it is also possible to form acid addition salts, for example with strong inorganic acids, such as mineral acids, for example sulfuric acid, a phosphoric acid or a hydrohalic acid, with strong organic carboxylic acids, such as lower alkanecarboxylic acids, for example acetic acid, saturated or unsaturated dicarboxylic acids, for example malonic, maleic or fumaric acid, or hydroxycarboxylic acids, for example tartaric or citric acid, or with sulfonic acids, such as lower alkanesulfonic acids or unsubstituted or substituted benzenesulfonic acids, for example methane- or p-toluenesulfonic acid. Compounds of formula I having an acid group, for example carboxy, and a basic group, for example amino, may also be present in the form of internal salts, i.e. in zwitterionic form, or one part of the molecule may be in the form of an internal salt and another part in the form of a normal salt. Salts that are unsuitable for pharmaceutical applications are also included, since they can be used, for example, in the isolation and/or purification of free compounds I and of the pharmaceutically acceptable salts thereof.

The compounds of formula I have valuable pharmacological properties, especially pronounced binding of trivalent metal ions, especially those of iron (A. E. Martell and R. J. Motekaitis, "Determination and Use of Stability Constants", VCH Publishers, New York 1992). As can be demonstrated, for example, in the animal model using gall bladder fistula rats that are not overloaded with iron (R. J. Bergeron et al., *J. Med. Chem.* 34, 2072–2078 (1991); G. F. Smith, W. H. McCurdy and H. Diehl, *Analyst*77, 418–422 (1952)) or monkeys that are overloaded with iron (R. J. Bergeron et al., *Blood*81, 2166–2173 (1993)) at doses of from approximately 50 μmol/kg, they are capable, inter alia, of preventing the deposition of iron-containing pigments and, where there are existing iron deposits in the organism, of effecting excretion of the iron.

Various diseases of warm-blooded animals, especially humans, lead to an excess of iron(III) ions in the blood and to the deposition of iron-containing pigments in tissue, for example in the case of haemochromatosis, haemosiderosis, cirrhosis of the liver and poisoning with compounds of iron. Other diseases and pathological conditions of the human body (and of the bodies of other warm-blooded animals) associated with excessive loading of the organism with iron(III) ions ($Fe^{3+}$ ions) are, for example, thalassaemia, sickle-cell anaemia, sideroachrestic anaemia, aplastic anaemia and other forms of anaemia in which haemosiderosis (i.e. a local or general increase in iron reserves in otherwise undamaged body tissue) is involved. The type includes pathological conditions that develop in patients after multiple blood transfusions, or after repeated dialysis treatments where kidney function is absent or impaired. A reduction in iron(III) concentration is also of interest in the treatment of diseases caused by iron(III)-dependent microorganisms and parasites, which treatment is of fundamental importance not only in human medicine, for example in the case of malaria, but also in veterinary medicine. The formation of complexes with other trivalent metals can also be used to effect their excretion from the organism, for example to effect the removal of aluminium in the case of dialysis encephalopathy and osteomalacia, and in Alzheimer's disease.

Desferrioxamine B (H. Bickel, H. Keberle and E. Vischer, *Helv. Chim. Acta* 46, 1385–1389 [1963]) has already been known and used therapeutically for those purposes for a long time. However, a disadvantage of that composition is the fact that, when administered orally, desferrioxamine and its salts exhibit only low, inadequate activity and in all the possible applications mentioned above require a parenteral dosage form. For example, an especially effective method that is recommended is administration of the active ingredient by means of a slow (8- to 12-hour) subcutaneous infusion which, however, necessitates the use of a portable mechanical device, such as an electrically operated infusion syringe. Apart from their inconvenience, such solutions have the disadvantage that they require high levels of treatment, which greatly limits their use and, in particular, makes comprehensive treatment of thalassaemia in countries of the Mediterranean region, of the Middle East, India and South East Asia, of malaria worldwide and of sickle cell anaemia in the African countries impossible. Those widespread diseases continue to represent a serious problem for health authorities in those countries and make the search for a simpler and cheaper treatment, preferably by means of a composition that is effective orally, the most pressing task in that field.

It is known from GB 2 118 176 that oral doses of 1,2-dimethyl-3-hydroxy-pyrid-4-one and alkyl derivatives thereof are capable of reducing excess iron in tissue. There are, however, clear indications that, for example, the former compound, which is also known by the name of deferriprone, exhibits significant toxicity and can thus lead to serious side effects. Moreover, on administration, such compounds are capable of penetrating the blood/brain barrier and of causing undesired side effects in the brain. Compared with the known compounds, the novel compounds of the present invention have proved not only to be more effective orally but also to be well tolerated.

The present invention thus makes available compounds of formula I that are distinguished both by their outstanding oral effectiveness and by their ability to be tolerated even at high doses.

The invention relates more especially to compounds of formula I wherein $R_1$ is hydrogen, halogen, substituted or unsubstituted lower alkyl or lower alkoxycarbonyl, amino, lower alkylamino, di-lower alkylamino, aminocarbonyl, substituted or unsubstituted N-lower alkylaminocarbonyl or N,N-di-lower alkylaminocarbonyl, carboxyl, cyano, hydroxy, nitro, or lower alkylenedioxy which with the group B forms a heterocyclic oxygen-containing ring system;

$R_2$ is hydrogen, substituted or unsubstituted lower alkyl or lower alkylenehydroxy, substituted or unsubstituted lower alkylene-lower alkoxy, lower alkylenecarboxy, lower alkylenecarbonyl-lower alkoxy, substituted or unsubstituted lower alkyleneamine, substituted or unsubstituted N-lower alkanoyl-lower alkyleneamine, or $R_2$ together with A and the atoms to which they are bonded forms a substituted or unsubstituted oxygen-containing heterocyclic ring or $R_2$ together with $R_3$ and the atoms to which they are bonded forms a substituted or unsubstituted oxygen-containing heterocyclic ring;

$R_3$ is hydrogen, substituted or unsubstituted lower alkyl, carboxyl, substituted or unsubstituted lower alkanoyloxy-lower alkylene, substituted or unsubstituted lower alkyleneaminocarbonyl, or $R_3$ together with $R_2$ and the atoms to which they are bonded forms a substituted or unsubstituted oxygen-containing heterocyclic ring;

$R_4$ is hydrogen, lower alkanoyl, lower alkoxycarbonyl or a radical that can be removed under physiological conditions;

A is substituted or unsubstituted methylene, carbonyl, or A together with $R_2$ and the atoms to which they are bonded forms a substituted or unsubstituted oxygen-containing heterocyclic ring; and B is mono- or poly-substituted or unsubstituted aryl or mono- or poly-substituted or unsubstituted heteroaryl;

and to the stereoisomers, tautomers and pharmaceutically acceptable salts thereof.

The invention relates especially to compounds of formula I wherein $R_1$ is hydrogen, halogen, substituted or unsubstituted lower alkyl, substituted or unsubstituted lower alkoxy, cyano, hydroxy or nitro;

$R_2$ is substituted or unsubstituted lower alkyl, substituted or unsubstituted lower alkylenehydroxy or lower alkyleneamine, or $R_2$ together with A forms an unsubstituted saturated oxygen-containing heterocyclic ring;

$R_3$ is hydrogen;

$R_4$ is hydrogen, lower alkanoyl, lower alkoxycarbonyl or a radical that can be removed under physiological conditions;

A is substituted or unsubstituted methylene, carbonyl, or A together with $R_2$ and the atoms to which they are bonded forms an unsubstituted oxygen-containing heterocyclic ring; and B is mono-substituted or unsubstituted aryl or mono-substituted or unsubstituted heteroaryl;

and to the stereoisomers, tautomers and pharmaceutically acceptable salts thereof.

The invention relates above all to compounds of formula I wherein $R_1$ is hydrogen, halogen or unsubstituted lower alkyl;

$R_2$ is substituted or unsubstituted lower alkyl, substituted or unsubstituted lower alkylenehydroxy, or $R_2$ together with A and the atoms to which they are bonded forms an unsubstituted oxygen-containing heterocyclic ring;

$R_3$ and $R_4$ are hydrogen;

A is substituted or unsubstituted methylene, or A together with $R_2$ and the atoms to which they are bonded forms an unsubstituted oxygen-containing heterocyclic ring; and B is mono-substituted or unsubstituted aryl or mono-substituted or unsubstituted heteroaryl;

and to the stereoisomers, tautomers and pharmaceutically acceptable salts thereof.

The invention relates especially to the specific compounds described in the Examples and to salts thereof.

The invention relates very especially to 3-hydroxy-1-(2-hydroxy-ethyl)-2-(hydroxy-phenyl-methyl)-1H-pyridin-4-one; 3-hydroxy-1-(2-hydroxy-ethyl)-2-(4-methyl-benzyl)-1H-pyridin-4-one; 3-hydroxy-1-(2-hydroxy-ethyl)-2-(hydroxy-4-fluorophenyl-methyl)-1H-pyridin-4-one; 3-hydroxy-1-(2-hydroxy-ethyl)-2-(4-fluorobenzyl)-1H-pyridin-4-one; 3-hydroxy-1-(2-hydroxy-ethyl)-2-(hydroxy-4-chlorophenyl-methyl)-1H-pyridin-4-one; 3-hydroxy-1-(2-hydroxy-ethyl)-2-(4-chlorobenzyl)-1H-pyridin-4-one; or a stereoisomer, a tautomer or a pharmaceutically acceptable salt thereof.

The compounds can be prepared in a manner known per se by, for example, reacting a compound of formula II

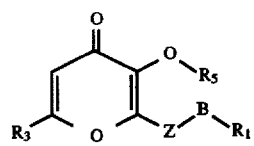

(II)

wherein $R_1$, $R_3$ and B are as defined for formula I, Z is unsubstituted or substituted methylene (substituents being, if necessary, in protected form) or carbonyl and $R_5$ has the same meaning as $R_4$ as defined for formula I or, if necessary, is a suitable protecting group, with a compound of formula III

 (III)

wherein $R_2$ is as defined for formula I, to form a compound of formula IV

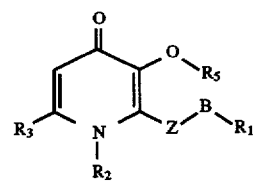

(IV)

wherein $R_1$, $R_2$, $R_3$, $R_5$, B and Z are as defined for formulae I and II, and converting that compound, a) if necessary by simultaneously removing a protecting group $R_5$ and a protecting group that may be present at the group Z, into a compound of formula I and, if desired, into a different compound of formula I, and/or, if desired, converting a resulting salt into the free compound or into a different salt, and/or, if desired, converting a resulting free compound of formula I having salt-forming properties into a salt, or b) if necessary after removing a protecting group $R_5$ or a protecting group that may be present at the group Z, first into a different protected form of a compound of formula I and, if desired, into a protected form of a different compound of formula I, and then, by removing the remaining protecting groups, into a compound of formula I, and, if desired, into a different compound of formula I, and/or, if desired, converting a resulting salt into the free compound or into a different salt, and/or, if desired, converting a resulting free compound of formula I having salt-forming properties into a salt.

In the following detailed description of the process, the symbols $R_1$–$R_5$, A, B and Z are each as defined for formulae I and II, unless otherwise indicated.

The process corresponds to the reaction known per se of 3-hydroxypyran-4-ones with ammonia or primary amines.

Protecting groups and their introduction and removal are described, for example, in J. F. W. McOmie, "Protective Groups in Organic Chemistry", Plenum Press, London, New York 1973, and in "Methoden der organischen Chemie", Houben-Weyl, 4th edition, Vol. 15/1, Georg-Thieme-Verlag, Stuttgart 1974 and in Theodora W. Greene, "Protective Groups in Organic Synthesis", John Wiley & Sons, New York 1981. It is a characteristic of protecting groups that they can be removed readily, i.e. without undesired secondary reactions taking place, for example by solvolysis, reduction, photolysis or also under physiological conditions.

Hydroxy groups may be present, for example, in the form of a readily cleavable ester or ether group, preferably an alkanoyl or aralkanoyl ester group or a cycloheteroalkyl, aralkyl or alkoxyalkyl ether group, but also a silyl ester or silyl ether group, especially in the form of an acetyl or benzoyl ester or of a tetrahydropyranyl, benzyl or methoxymethyl ether.

The reaction between the pyranone of formula II and the amine of formula III takes place without a solvent or in suitable inert polar solvents, especially mono- or polyhydric alcohols, for example lower alkanols or lower alkanepolyols, such as methanol, propanol, isopropanol, glycol, propanediol, or especially ethanol, ethylene glycol or diethylene glycol. In some cases the addition of a base, for example a tertiary amine, is advantageous.

The reaction takes place at room temperature or at elevated temperatures, preferably from room temperature to the reflux temperature of the reaction mixture. The temperature can also be increased or reduced during the period of the reaction.

The starting materials of formula II are novel and the present invention relates also thereto. They can be prepared in accordance with processes known per se by reacting pyromeconic acid [CAS-Registry No.: 496-63-9] or suitable derivatives with the corresponding aryl or heteroaryl aldehydes and, if necessary, subsequently introducing suitable protecting groups, and, where appropriate, derivatising further in accordance with methods known per se.

For example, compounds of formula II are obtained by reacting pyromeconic acid in ethanolic sodium hydroxide solution in a manner known per se with an aldehyde of formula V

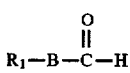

$$R_1—B—\overset{\overset{O}{\|}}{C}—H \qquad (V)$$

wherein $R_1$ and B are as defined for formula I and then, if desired, introducing suitable protecting groups, that is to say, for example, etherifying the 3-hydroxy function with an aralkyl halide in a manner known per se and protecting the exocyclic hydroxy function with a cycloheteroalkyl ether.

The removal of the protecting groups that are not constituents of the desired end product of formula I is effected in a manner known per se, for example by means of solvolysis, especially hydrolysis, alcoholysis or acidolysis, or by means of reduction, especially hydrogenolysis or chemical reduction, as appropriate step-wise or simultaneously.

Compounds of formula I can also be converted into different compounds of formula I.

For example, a compound of formula I wherein A is hydroxymethylidene can be oxidised to the corresponding carbonyl compound, yielding a compound of formula I wherein A is carbonyl. The reaction is carried out, for example, in an inert non-polar solvent, such as a halo-lower alkane, with the addition of a bisalkanesulfoxide and a pyridine-$SO_3$ complex.

A compound of formula I wherein A is hydroxymethylidene can, for example, also be reduced to the corresponding alkane, yielding a compound of formula I wherein A is methylene. For that purpose, for example, the compound is first acylated and then, in the presence of a catalyst, for example palladium, reacted with hydrogen.

A compound of formula I wherein $R_2$ is hydroxyalkylene and A is hydroxymethylidene can be reacted in a manner known per se, for example in the presence of an acid, to form an internal ether, with the result that $R_2$ and A, together with the atoms to which they are bonded, form an oxygen-containing azaheterocycle.

A compound of formula I wherein $R_2$ is hydroxyalkylene and $R_3$ is carboxy can be reacted in a manner known per se, for example in the presence of an acid, to form an internal ester, with the result that $R_2$ and $R_3$, together with the atoms to which they are bonded, form an oxygen-containing azaheterocycle.

A compound of formula I wherein $R_2$ is lower alkylenecarboxy and A is hydroxymethylidene can be reacted in a manner known per se, for example in the presence of an acid, to form an internal ester, with the result that $R_2$ and A, together with the atoms to which they are bonded, form an oxygen-containing azaheterocycle.

If starting compounds of formula I or any of the intermediates contain interfering reactive groups, for example carboxy, hydroxy or amino groups, those groups can be temporarily protected by readily removable protecting groups. Advantageously, however, a suitable intermediate of formula IV can be used for the reaction.

Customary processes are used for working up the obtainable compounds of formula I or the salts thereof, and, if necessary, the intermediates, for example solvolysis of excess reagents; recrystallisation; chromatography, for example partition, ion or gel chromatography; partitioning between inorganic and organic solvent phases; single or multiple extraction, especially after acidifying or increasing the basicity or the salt content; drying over hygroscopic salts or at elevated temperature, where appropriate while passing a stream of gas through or over the reaction mixture; digesting; filtering; washing; dissolving; concentrating by evaporation (if necessary in vacuo or under a high vacuum); distillation; precipitation; centrifuging; crystallisation, for example of compounds obtained in oil form or from the mother liquor, inoculation with a crystal of the end product also being possible; or a combination of two or more of the mentioned working-up steps, which can also be used repeatedly, etc.

Starting materials and intermediates can be used in pure form, for example after working-up, as just mentioned, in partly purified form or also, for example, directly in the form of the crude product.

The compounds, including their salts, may also be obtained in the form of hydrates or solvates, or their crystals may include, for example, the solvent used for crystallisation.

Solvents and diluents are, for example, water, alcohols, for example lower alkanols, such as methanol, ethanol, propanol or butanol, diols, such as ethylene glycol, triols or polyols, such as glycerol or diethylene glycol, or aryl alcohols, such as phenol or benzyl alcohol, acid amides, for example carboxylic acid amides, such as N,N-dimethylformamide or N,N-dimethylacetamide, amides of inorganic acids, such as hexamethylphosphoric acid triamide, ethers, for example cyclic ethers, such as tetrahydrofuran or dioxane, or acyclic ethers, such as diethyl ether or ethylene glycol dimethyl ether, halogenated hydrocarbons, such as halo-lower alkanes, for example methylene chloride or chloroform, ketones, such as acetone, nitriles, such as acetonitrile, esters, such as ethyl acetate, bisalkanesulfoxides, such as dimethyl sulfoxide, nitrogen-containing heterocycles, such as N-methylpyrrolidone or pyridine, hydrocarbons, for example lower alkanes, such as hexane or heptane, or aromatic compounds, such as benzene, toluene or xylene(s), or mixtures of those solvents, it being possible for suitable solvents to be selected for each of the above-mentioned reactions and working-up steps.

In the process of the present invention, the starling materials and intermediates used, in each case in free form or in salt form, are preferably those that lead to the compounds I described at the beginning as being especially valuable or the salts thereof. The invention relates also to novel staffing materials and intermediates, in each case in free form or in salt form, for the preparation of the compounds I or the salts thereof, to the use thereof and to processes for the preparation thereof.

The invention relates also to those forms of the process in which a compound obtainable as intermediate at any stage of the process is used as starting material and the remaining process steps are carried out or in which a starting material is formed under the reaction conditions or is used in the form of a derivative, for example a salt, thereof.

Salts of compounds I can be prepared in a manner known per se. For example, acid addition salts of compounds I are obtained by treatment with a suitable acid or a suitable ion-exchange reagent and salts with bases by treatment with a suitable base or a suitable ion exchange reagent. Salts of compounds of formula I can be converted into the free compounds I in customary manner; for example, acid addition salts can be converted by treatment with a suitable basic agent or a suitable ion exchange reagent, and salts with bases, for example, by treatment with a suitable acid or a suitable ion exchange reagent.

Salts of compounds I can be converted into different salts of compounds I in a manner known per se; for example, acid addition salts can be converted into different acid addition salts by treatment of a salt of an organic acid, such as a hydrochloride, with a suitable metal salt, such as a sodium, barium or silver salt, of an acid, for example silver acetate, in a suitable solvent in which an organic salt that is formed, for example silver chloride, is insoluble and thus separates out from the reaction mixture.

Depending upon the procedure and/or the reaction conditions, the compounds I having salt-forming properties can be obtained in free form or in the form of salts.

In view of the close relationship between the compound I in free form and in the form of its salts, hereinabove and hereinbelow any reference to the free compound I and its salts is to be understood as including also the corresponding salts and the free compound I, respectively, as appropriate and expedient.

The compounds I, including the salts of salt-forming compounds, may also be obtained in the form of their hydrates and/or may include other solvents, for example solvents which may have been used for the crystallisation of compounds in solid form.

Depending upon the starting materials and procedures chosen, the compounds I and their salts may be present in the form of one of the possible isomers, for example stereoisomers or tautomers, or as a mixture thereof. There are obtainable as pure isomers, for example, pure enantiomers, pure diastereoisomers or pure tautomers. Accordingly, there may be present as isomeric mixtures, for example, racemates or diastereoisomeric mixtures. Mixtures of isomers of compounds I in free form or in salt form obtainable in accordance with the process or by another method can be separated into the components in customary manner, for example on the basis of the physicochemical differences between the constituents in known manner by means of fractional crystallisation, distillation and/or chromatography. Advantageously, the more active isomer is isolated.

The invention relates also to the use of compounds I and the pharmaceutically acceptable salts thereof in the treatment of diseases that cause or are caused by an excess of iron in the human or animal body, preferably in the form of pharmaceutically acceptable preparations, especially in a method for the therapeutic treatment of the human body, and to such a method of treatment.

The invention relates likewise to pharmaceutical compositions comprising a compound I or a pharmaceutically acceptable salt thereof as active ingredient, and to processes for the preparation thereof. Those pharmaceutical compositions are those for enteral, especially oral, and also rectal administration and those for parenteral administration to warm-blooded animals, especially humans, the pharmacological active ingredient being present alone or together with customary pharmaceutical excipients. The pharmaceutical compositions comprise (in percent by weight), for example, from approximately 0.001% to 100%, preferably from approximately 0.1% to approximately 100%, active ingredient.

Pharmaceutical compositions for enteral and parenteral administration are, for example, those in unit dose forms, such as dragées, tablets, dispersible tablets, effervescent tablets, capsules, suspensible powders, suspensions or suppositories, or ampoules. They are prepared in a manner known per se, for example by means of conventional confectioning, mixing, granulating or lyophilising processes. Pharmaceutical compositions for oral administration can be obtained, for example, by combining the active ingredient with solid carriers, if desired granulating a resulting mixture, and processing the mixture or granules, if desired or necessary after the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and also binders, such as starch pastes using, for example, corn, wheat, rice or potato starch, gelatin, tragacanth, methylcellulose and/or polyvinylpyrrolidone, and/or, if desired, disintegrators, such as the above-mentioned starches, also carboxymethyl starch, crosslinked polyvinylpyrrolidone, agar or alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores can be provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, for example for identification purposes or to indicate different doses of active ingredient.

Dispersible tablets are tablets that disintegrate rapidly in relative small amounts of liquid, for example water, and may comprise flavourings or substances for masking the inherent taste of the active ingredient. They can be used advantageously for the oral administration of large single doses in which the amount of active ingredient to be administered is so great that it cannot be taken comfortably, especially by children, when administered in the form of tablets that are to be swallowed whole or unchewed. Other orally administrable pharmaceutical compositions are hard gelatin capsules and also soft, sealed capsules consisting of gelatin and a plasticiser, such as glycerol or sorbitol. The hard gelatin capsules may comprise the active ingredient in the form of granules, for example in admixture with fillers, such as lactose, binders, such as starches, and/or glidants, such as talc or magnesium stearate, and if desired stabilisers. In soft capsules the active ingredient is preferably dissolved or suspended in suitable liquids, such as fatty oils, paraffin oil or liquid polyethylene glycols, it likewise being possible to add stabilisers.

Furthermore, there are also suitable for an oral dosage form suspensible powders, for example those known as "Powder in Bottle", abbreviated to "PIB", or ready-to-drink suspensions. For that dosage form, the active ingredient is mixed, for example, with pharmaceutically acceptable surfactants, such as sodium lauryl sulfate or polysorbate, suspension agents, for example hydroxypropylcellulose, hydroxypropylmethylcellulose or another such agent known from the prior art and previously described, for example, in the "Handbook of Pharmaceutical Excipients", pH-regulators, such as citric acid or tartaric acid and the salts thereof, or a USP buffer and, where appropriate, fillers, for example lactose, and other excipients and introduced into suitable vessels, advantageously single-dose vials or ampoules. Immediately before administration, a specific amount of water is added and the suspension is prepared by shaking. Alternatively, the water can be added before the introduction into the vessels.

Suitable rectally administrable pharmaceutical compositions are, for example, suppositories that consist of a combination of the active ingredient with a suppository base material. Suitable suppository base materials are, for example, natural or synthetic triglycerides, paraffin hydrocarbons, polyethylene glycols or higher alkanols. It is also possible to use gelatin rectal capsules which comprise a combination of the active ingredient with a base material. Suitable base materials are, for example, liquid triglycerides, polyethylene glycols or paraffin hydrocarbons.

For parenteral administration there are suitable, especially, aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions which comprise viscosity-increasing substances, for example sodium carboxymethylcellulose, sorbitol and/or dextran, and optionally also stabilisers.

The dosage of the active ingredient may depend on various factors, such as the effectiveness and duration of action of the active ingredient, the severity of the disease to be treated and/or of its symptoms, the mode of administration and the species, sex, age, weight and/or individual condition of the warm-blooded animal. In the case of oral administration the daily doses to be administered are from 10 to approximately 120 mg/kg, especially from 20 to approximately 80 mg/kg and, for a warm-blooded animal having a body weight of approximately 40 kg, preferably from approximately 400 mg to approximately 4800 mg, especially approximately 800 mg to 3200 mg, advantageously divided into from 2 to 12 single doses.

The Examples that follow are intended to illustrate the invention described hereinbefore, but without limiting the invention thereto. (Unless otherwise indicated, hereinbefore and hereinafter the definitions of the following abbreviations are: dimethylformamide=N,N-dimethylformamide; ether= diethyl ether;, HCl=hydrochloric acid (aqueous solution); NaOH=sodium hydroxide solution (aqueous); m.p.=melting point).

EXAMPLE 1

3-Hydroxy-1-(2-hydroxy-ethyl)-2-(hydroxy-phenyl-methyl)-1H-pyridin-4-one 12.37 g of 3-benzyloxy-1-(2-hydroxy-ethyl)-2-(hydroxy-phenyl-methyl)-1H-pyridin-4-one are dissolved in 200 ml of methanol and hydrogenated at room temperature over 1.2 g of palladium on carbon (5%) until 1 mol of $H_2$ per mol of starting material has been taken up. The catalyst is removed by filtration and the filtrate is concentrated to dryness by evaporation using a rotary evaporator. Recrystallisation from methanol yields 3-hydroxy-1-(2-hydroxy-ethyl)-2-(hydroxy-phenyl-methyl)-1H-pyridin-4-one in the form of colourless crystals. M.p.: 198°–200° C.

The starting material can be prepared, for example, as follows:

a) 3-Benzyloxy-2-(hydroxy-phenyl-methyl)-pyran-4-one: 29.5 g of 3-hydroxy-2-(hydroxy-phenyl-methyl)-pyran-4-one (described in: BE 651427 [CAS No.: 4940-15-2]) and 40 g of powdered potassium carbonate are introduced with stirring into 210 ml of dimethylformamide. 24.3 g of benzyl bromide are added and the suspension is stirred at room temperature for 18 hours. For working-up, the reaction mixture is poured into 1000 ml of water and extracted twice with 300 ml of ethyl acetate each time. The organic phases are washed four times with 50 ml of water each time, combined and dried over magnesium sulfate. The drying agent is removed by filtration and the filtrate is concentrated by evaporation using a rotary evaporator. The residue is stirred with diethyl ether and filtered. Drying yields 3-benzyloxy-2-(hydroxy-phenyl-methyl)-pyran-4-one in the form of pale-yellow crystals. M.p.:121°–122° C.

b) 3-Benzyloxy-2-[phenyl-(tetrahydropyran-2-yloxy)-methyl]-pyran-4-one: 250 ml of dichloromethane and 10 ml of 3,4-dihydro-2H-pyran [CAS No.:110-87-2] are added to 23.1 g of 3-benzyloxy-2-(hydroxy-phenyl-methyl)-pyran-4-one. After the addition of 0.1 g of p-toluene-sulfonic acid, stirring is carried out at room temperature for 5 hours. The solution is washed once with dilute sodium hydrogen carbonate solution and twice with water and then dried over magnesium sulfate and filtered. Concentration by evaporation yields 3-benzyloxy-2-[phenyl-(tetrahydropyran-2-yloxy)-methyl]-pyran-4-one in the form of a yellowish crystalline diastereoisomeric mixture. M.p.: 115°–116.5° C.

c) 3-Benzyloxy-1-(2-hydroxy-ethyl)-2-[phenyl-(tetrahydropyran-2-yloxy)-methyl]-1H-pyridin-4-one: 11.8 g of 3-benzyloxy-2-[phenyl-(tetrahydropyran-2-yloxy)-methyl]-pyran-4-one, together with 10 ml of ethanolamine, are boiled under reflux for 26 hours in 100 ml of ethanol. For working-up, the ethanol is removed using a rotary evaporator. The residue is taken up in 200 ml of ethyl acetate and washed three times with 50 ml of water each time. The organic phase is dried over magnesium sulfate, filtered and concentrated to dryness by evaporation using a rotary evaporator. 3-Benzyloxy-1-(2-hydroxy-ethyl)-2-[phenyl-(tetrahydropyran-2-yloxy)-methyl]-1H-pyridin-4-one, in the form of a brown resin, remains as residue. Diastereoisomeric mixture, $R_1$ value: 0.2 (silica gel 60; ethyl acetate/ethanol 9/1).

d) 3-Benzyloxy-1-(2-hydroxy-ethyl)-2-(hydroxy-phenyl-methyl)-1H-pyridin-4-one: 3.39 g of 3-benzyloxy-1-(2-hydroxy-ethyl)-2-[phenyl-(tetrahydropyran-2-yloxy)-methyl]-1H-pyridin-4-one are boiled under reflux for 3 hours in 40 ml of ethanol and 10 ml of 2N HCl. For working-up, the ethanol is removed using a rotary evaporator. The residue is diluted with 50 ml of water and covered with 10 ml of ethyl acetate. Then, with stirring, 25 ml of saturated aqueous sodium hydrogen carbonate solution are added. The resulting product is filtered off and washed with water and ethyl acetate. After drying, 3-benzyloxy-1-(2-hydroxy-ethyl)-2-(hydroxy-phenyl-methyl)-1H-pyridin-4-one remains, in the form of colourless crystals. M.p.: 191.5°–192.5° C.

EXAMPLE 2

2-Benzyl-3-hydroxy-1-(2-hydroxy-ethyl)-1H-pyridin-4-one 2.14 g of 3-benzyloxy-1-(2-hydroxy-ethyl)-2-(hydroxy-phenyl-methyl)-1H-pyridin-4-one (Example 1d) are hydrogenated in 200 ml of methanol over 0.5 g of palladium on carbon (5%) under normal pressure and at a temperature of 50° C. until 2 mol of $H_2$ per mol of starting material have been taken up. The catalyst is removed by filtration and the filtrate is concentrated by evaporation using a rotary evaporator. The residue is recrystallised from ethanol, yielding 2-benzyl-3-hydroxy-1-(2-hydroxy-ethyl)-1H-pyridin-4-one in the form of colourless crystals. M.p.: 228°–230° C.

The same product can also be prepared as follows:

0.915 g of 2-benzyl-3-hydroxy-1-(2-acetoxy-ethyl)-1H-pyridin-4-one (Example 42) are stirred at room temperature in a mixture of 2 ml of 2N NaOH and 10 ml of ethanol for 24 hours. Then 2 ml of 2N HCl are added and the reaction mixture is stirred at room temperature for one hour, filtered and washed with cold ethanol. Drying yields 2-benzyl-3-hydroxy-1-(2-hydroxy-ethyl)-1H-pyridin-4-one.

EXAMPLE 3

2-[(4-Fluorophenyl)-hydroxy-methyl]-3-hydroxy-1-(2-hydroxy-ethyl)-1H-pyridin-4-one 1.72 g of 2-[(4-fluorophenyl)-hydroxy-methyl]-3-benzyloxy-1-(2-hydroxy-ethyl)-1H-pyridin-4-one are hydrogenated analogously to Example 1, yielding 2-[(4-fluorophenyl)-hydroxy-methyl]-3-hydroxy-1-(2-hydroxy-ethyl)-1H-pyridin-4-one. Colourless crystals, m.p.: 180°–185° C., crystal transformation, then m.p.: 200°–203° C.

The starting material can be prepared, for example, as follows:

a) 2-[4-Fluorophenyl)-hydroxy-methyl]-3-hydroxy-pyran-4-one: With stirring at room temperature, 5.6 g of pyromeconic acid (3-hydroxy-pyran-4-one) [CAS No.: 496-63-9] are dissolved in 10 ml of water and 24.5 ml of 2N NaOH. 6.33 g of 4-fluorobenzaldehyde and 25 ml of ethanol are added and the reaction mixture is stirred at room temperature for 18 hours. For working-up, the ethanol is removed using a rotary evaporator and the aqueous solution that remains is neutralised with 24.5 ml of 2N HCl. The product that has crystallised out is filtered off, washed with water and dried, yielding 2-[(4-fluorophenyl)-hydroxy-methyl]-3-hydroxy-pyran-4-one in the form of colourless crystals. M.p.: 154°–156° C.

b) 2-[(4-Fluorophenyl)-hydroxy-methyl]-3-benzyloxy-pyran-4-one: Reaction of 9 g of 2-[(4-fluorophenyl)-hydroxy-methyl]-3-hydroxy-pyran-4-one with benzyl bromide in dimethylformamide and potassium carbonate analogously to Example 1a yields: 2-[(4-fluorophenyl)-hydroxy-methyl]-3-benzyloxy-pyran-4-one. Colourless crystals, m.p.: 117°–117.5° C.

c) 3-Benzyloxy-2-[(4-fluorophenyl)-(tetrahydropyran-2-yloxy)-methyl]pyran-4-one: Reaction of 10.8 g of 2-[(4-fluorophenyl)-hydroxy-methyl]-3-benzyloxy-pyran-4-one with 3,4-dihydro-2H-pyran analogously to Example 1b yields: 3-benzyloxy-2-[(4-fluorophenyl)-(tetrahydropyran-2-yloxy)-methyl]-pyran-4-one in the form of a crystalline diastereoisomeric mixture. M.p.: 104°–107° C.

d) 3-Benzyloxy-1-(2-hydroxy-ethyl)-2-[(4-fluorophenyl)-(tetrahydropyran-2-yloxy)-methyl]-1H-pyridin-4-one: 4.1 g of 3-benzyloxy-2-[(4-fluorophenyl)-(tetrahydropyran-2-yloxy)-methyl]-pyran-4-one in 40 ml of ethanol and 8 ml of ethanolamine are boiled under reflux for 24 hours. Working-up analogously to Example 1c yields 3-benzyloxy-1-(2-hydroxy-ethyl)-2-[(4-fluorophenyl)-(tetrahydropyran-2-yloxy)-methyl]-1H-pyridin-4-one in the form of a brittle resin, $R_f$ value: 0.15 (silica gel 60, ethyl acetate/ethanol 9/1).

e) 2-[4-Fluorophenyl)-hydroxy-methyl]-3-benzyloxy-1-(2-hydroxy-ethyl)-1H-pyridin-4-one: 13.7 g of 3-benzyloxy-1-(2-hydroxy-ethyl)-2-[(4-fluorophenyl)-(tetrahydropyran-2-yloxy)-methyl]-1H-pyridin-4-one are boiled under reflux for 3 hours in 150 ml of ethanol and 50 ml of 2N HCl. For working-up, the ethanol is removed using a rotary evaporator. The residue is diluted with 50 ml of water and covered with 50 ml of ethyl acetate. Then, with stirring, 50 ml of 2N NaOH are added. The resulting product is filtered off and washed with water and ethyl acetate. After drying, 2-[(4-fluorophenyl)-hydroxy-methyl]-3-benzyloxy-1-(2-hydroxy-ethyl)-1H-pyridin-4-one remains, in the form of colourless crystals. M.p.: 187°–187.5° C.

EXAMPLE 4

3-Hydroxy-1-methyl-2-(hydroxy-phenyl-methyl)-1H-pyridin-4-one:

Under normal pressure and at room temperature, 0.643 g of 3-benzyloxy-1-methyl- 2-(hydroxy-phenyl-methyl)-1H-pyridin-4-one is hydrogenated in 25 ml of methanol over 0.1 g of palladium on carbon (5%) until 1 mol of $H_2$ per mol of starting material has been taken up. Removal of the catalyst and recrystallisation from methanol yield 3-hydroxy-1-methyl-2-(hydroxy-phenyl-methyl)-1H-pyridin-4-one. M.p.: 210°–213° C.

The starting material can be prepared, for example, as follows:

a) 3-Benzyloxy-2-[phenyl-(tetrahydropyran-2-yloxy)-methyl]-1-methyl-1H-pyridin-4-one: 50 ml of a 30% solution of methylamine in ethanol are added to 4.6 g of 3-benzyloxy-2-[phenyl-(tetrahydropyran-2-yloxy)-methyl]-pyran-4-one (Example 1b) and the reaction mixture is covered and left to stand at room temperature for 96 hours. For working-up, the reaction mixture is concentrated to dryness by evaporation using a rotary evaporator. A crude diastereoisomeric mixture of 3-benzyloxy-2-[phenyl-(tetrahydropyran-2-yloxy)-methyl]-1-methyl-1H-pyridin-4-one is obtained. $R_f$ value: 0.2 (silica gel 60, ethyl acetate/ethanol 9/1).

b) 3-Benzyloxy-1-methyl-2-(hydroxy-phenyl-methyl)-1H-pyridin-4-one: From 4.1 g of 3-benzyloxy-2-[phenyl-(tetrahydropyran-2-yloxy)-methyl]-1-methyl-1H-pyridin-4-one there is obtained analogously to Example 1d: 3-benzyloxy-1-methyl-2-(hydroxy-phenyl-methyl)-1H-pyridin-4-one in the form of pale-yellow crystals. M.p.: 181.5°–183.5° C.

EXAMPLE 5

2-Benzoyl-3-hydroxy-1-(2.-hydroxy-ethyl)-1H-pyridin-4-one

At room temperature and under normal pressure, 0.95 g of 2-benzoyl-3-benzyloxy-1-(2-benzyloxy-ethyl)-1H-pyridin-4-one is hydrogenated in methanol until 2 mol of $H_2$ per mol of starting material have been taken up. The catalyst is removed and the reaction mixture is concentrated by evaporation using a rotary evaporator. The residue is chromatographed on 20 g of silica gel. A mixture of ethyl acetate and ethanol in a ratio of 95:5 is used as eluant. With fraction sizes of 17 ml, the product in fractions 6–20 is eluted. Recrystallisation from ethanol yields 2-benzoyl-3-hydroxy-1-(2-hydroxy-ethyl)-1H-pyridin-4-one in the form of colourless crystals. M.p.: 195°–200° C.

The starting material can be prepared, for example, as follows:

a) 3-Benzyloxy-1-(2-benzyloxy-ethyl)-2-[phenyl-(tetrahydropyran-2-yloxy)-methyl]-1H-pyridin-4-one: 3.39 g of 3-benzyloxy-2-[phenyl-(tetrahydropyran-2-yloxy)-methyl]-pyran-4-one (Example 1b), together with 5 ml of 2-benzyloxyethylamine in 25 ml of diethylene glycol, are stirred at 120° C. for 26 hours. For working-up, the reaction mixture is diluted with 300 ml of water and extracted twice with 100 ml of ethyl acetate each time. The organic phases are washed three times with 50 ml of water each time. The organic phases are combined, dried over magnesium sulfate and filtered and the flitrate is concentrated to dryness by evaporation using a rotary evaporator. The residue is chromatographed on 260 g of silica gel. A mixture of ethyl acetate and ethanol in a ratio of 98/2 is used as eluant. With fraction sizes of 140 ml, fractions 11–24 contain the product. 3-Benzyloxy-1-(2-benzyloxy-ethyl)-2-[phenyl-(tetrahydropyran-2-yloxy)-methyl]-1H-pyridin-4-one is obtained in the form of clear yellow resin. Diastereoisomeric mixture, $R_f$ value: 0.31 (silica gel 60, ethyl acetate/ethanol 95/5).

b) 3-Benzyloxy-1-(2-benzyloxy-ethyl)-2-(hydroxy-phenyl-methyl)-1H-pyridin-4-one: 2.65 g of 3-benzyloxy-1-(2- benzyloxy-ethyl)-2-[phenyl-(tetrahydropyran-2-yloxy)-methyl]-1H-pyridin-4-one are boiled under reflux for 3 hours in 25 ml of ethanol and 10 ml of 2N HCl. The ethanol is removed using a rotary evaporator and the remaining aqueous solution is neutralised with excess aqueous sodium hydrogen carbonate solution. The resulting product is extracted twice with 50 ml of ethyl acetate each time. The organic phases are washed twice with 20 ml of water each time. The organic phases are combined, dried over magnesium sulfate and filtered and the flitrate is concentrated to dryness by evaporation using a rotary evaporator. The residue is recrystallised from ethyl acetate, yielding 3-benzyloxy-1-(2-benzyloxy-ethyl)-2-(hydroxy-phenyl-methyl)-1H-pyridin-4-one. Yellowish crystals, m.p.: 154°–155° C.

c) 2-Benzoyl-3-benzyloxy-1-(2-benzyloxy-ethyl)-1H-pyrdin-4-one: 1.79 g of 3-benzyloxy-1-(2-benzyloxy-ethyl)-2-(hydroxy-phenyl-methyl)-1H-pyridin-4-one are introduced into 20 ml of dichloroethane and 5 ml of dimethyl sulfoxide. 3.5 ml of triethylamine are added and the reaction mixture is cooled with an ice-bath to an internal temperature of 3°–5° C. Then 2.58 g of pyridine $SO_3$ complex [CAS No.: 26412-87-3] are added and the mixture is allowed to thaw to room temperature. After stirring for 18 hours at room temperature, the reaction mixture is extracted by shaking twice with water and the organic phase is dried over magnesium sulfate, filtered and concentrated to dryness by evaporation using a rotary evaporator. The residue is chromatographed on silica gel. A mixture of ethyl acetate and ethanol in a ratio of 95/5 is used as eluant. 2-Benzoyl-3-benzyloxy-1-(2-benzyloxy-ethyl)-1H-pyridin-4-one is obtained in the form of a thick yellow oil. $R_f$ value: 0.18 (silica gel 60, ethyl acetate/ethanol 95/5).

EXAMPLE 6

3-Hydroxy-1-(2-hydroxy-ethyl)-2-(hydroxy-pyridin-3-yl-methyl)-1H-pyridin-4-one

At room temperature and under normal pressure, 0.6 g of 3-benzyloxy-1-(2-hydroxy-ethyl)-2-(hydroxy-pyridin-3-yl-methyl)-1H-pyridin-4-one are hydrogenated in 20 ml of methanol until 1 mol of $H_2$ per mol of starting material has been taken up. The catalyst is removed by filtration and the flitrate is concentrated to dryness by evaporation. The residue is recrystallised from methanol, yielding 3-hydroxy-1-(2-hydroxy-ethyl)-2-(hydroxy-pyridin-3-yl-methyl)-1H-pyridin-4-one in the form of colourless crystals, m.p.: 189°–190.5° C.

The starting material can be prepared, for example, as follows:

a) 2-(Hydroxy-pyridin-3-yl-methyl)-3-hydroxy-pyran-4-one: With stirring at room temperature, 5.6 g of pyromeconic acid are dissolved in 11 ml of water and 23.7 ml of 2N NaOH. 5.52 g of pyridine-3-carbaldehyde [CAS No.: 500-22-1] are added and the reaction mixture is stirred at room temperature for 18 hours and then neutralised with 23.7 ml of 2N HCl. The resulting crystal suspension is cooled in an ice-bath for 2 hours and then filtered and washed with a small amount of cold water. Drying yields 2-(hydroxy-pyridin-3-yl-methyl)-3-hydroxy-pyran-4-one. Pale-yellow crystals, m.p.: 176°–180° C. with decomposition.

b) 3-Benzyloxy-2-(hydroxy-pyridin-3-yl-methyl)-pyran-4-one: 60 ml of dimethylformamide are poured over 10.6 g of 2-(hydroxy-pyridin-3-yl-methyl)-3-hydroxy-pyran-4-one and 14 g of potassium carbonate. The mixture is stirred in an ice-bath and 8.27 g of benzyl bromide are added. After stirring for 6 hours in an ice-bath, the reaction mixture is allowed to thaw to room temperature and stirred at that temperature for a further 16 hours. The reaction mixture is then poured into 500 ml of water and extracted twice with 100 ml of ethyl acetate each time. The organic phases are washed four times with 50 ml of water each time. The organic phases are combined, dried over magnesium sulfate and filtered and the filtrate is concentrated to dryness by evaporation using a rotary evaporator. The residue is chromatographed on 300 g of silica gel. A mixture of ethyl acetate and ethanol in a ratio of 95/5 is used as eluant. 3-Benzyloxy-2-(hydroxy-pyridin-3-yl-methyl)-pyran-4-one is obtained in the form of a brittle yellow foam. $R_f$ value: 0.4 (silica gel 60, ethyl acetate/ethanol 9/1).

c) 3-Benzyloxy-2-[pyridin-3-yl-(tetrahydropyran-2-yloxy)-methyl]-pyran-4-one: 7.39 g of 3-benzyloxy-2-(hydroxy-pyridin-3-yl-methyl)-pyran-4-one are dissolved in 75 ml of dichloromethane and 4.3 ml of 3,4-dihydro-2H-pyran, 5 ml of a solution of HCl in diethyl ether (5N) are added and the reaction mixture is left to stand at room temperature for 48 hours. Shaking is carded out once with 50 ml of saturated sodium hydrogen carbonate solution and twice with 20 ml of water each time. The organic phase is dried over magnesium sulfate, filtered and concentrated to dryness by evaporation. 3-Benzyloxy-2-[pyridin-3-yl-(tetra-hydropyran-2-yloxy)-methyl]-pyran-4-one in the form of a yellow resin is obtained as residue. Diastereoisomeric mixture. $R_f$ value: 0.42 (silica gel 60, ethyl acetate/ethanol 9/1).

d) 3-Benzyloxy-1-(2-hydroxy-ethyl)-2-[pyridin-3-yl-(tetrahydropyran-2-yloxy)-methyl]-1H-pyridin-4-one: 4.3 g of 3-benzyloxy-2-[pyridin-3-yl-(tetrahydropyran-2-yloxy)-methyl]-pyran-4-one, together with 5 ml of ethanolamine, are boiled under reflux for 18 hours in 50 ml of ethanol and then the ethanol is removed using a rotary evaporator. Working-up analogously to Example 1c yields 3-benzyloxy-1-(2-hydroxy-ethyl)-2-[pyridin-3-yl-(tetrahydropyran-2-yl-oxy)-methyl]-1H-pyridin-4-one in the form of a viscous yellow resin. Diastereoisomeric mixture, $R_f$ value: 0.41 (silica gel 60, dichloromethane/ethanol 4/1).

e) 3-Benzyloxy-1-(2-hydroxy-ethyl)-2-(hydroxy-pyridin-3-yl-methyl)-1H-pyridin-4-one: 2.7 g of 3-benzyloxy-1-(2-hydroxy-ethyl)-2-[pyridin-3-yl-(tetrahydropyran-2-yloxy)-methyl]-1H-pyridin-4-one are boiled under reflux for 3 hours in a mixture of 12 ml of ethanol and 12 ml of 2N HCl. The ethanol is removed using a rotary evaporator and the aqueous solution that remains is neutralised with excess aqueous sodium hydrogen carbonate solution. The resulting product is extracted twice with 50 ml of ethyl acetate each time. The organic phases are washed twice with 20 ml of water each time. The organic phases are combined, dried over magnesium sulfate and filtered and the filtrate is concentrated to dryness by evaporation using a rotary evaporator. Recrystallisation from dichloromethane yields 3-benzyloxy-1-(2-hydroxy-ethyl)-2-(hydroxy-pyridin-3-yl-methyl)-1H-pyridin-4-one in the form of colourless crystals. M.p.: 182°–183° C.

EXAMPLE 7

3-Hydroxy-2-(hydroxy-pyridin-3-yl-methyl)-1-methyl-1H-pyridin-4-one

Under normal pressure and at room temperature, 1.34 g of 3-benzyloxy-2-(hydroxy-pyridin-3-yl-methyl)-1-methyl- 1H-pyridin-4-one are hydrogenated in 30 ml of methanol over 0.13 g of palladium on carbon (5%) until 1 mol of $H_2$ per mol of starting material has been taken up. Removal of the catalyst and recrystallisation from methanol/water yield 3-hydroxy-2-(hydroxy-pyridin-3-yl-ethyl)-1-methyl-1H-pyridin-4-one in the form of the monohydrate. M.p.: 215°–220° C.

The starting material can be prepared, for example, as follows:

a) 3-Benzyloxy-1-methyl-2-[pyridin-3-yl-(tetrahydropyran-2-yloxy)-methyl]-1H-pyridin-4-one: 13 ml of ethanol and 13 ml of a 30% solution of methylamine in ethanol are added to 2 g of 3-benzyloxy-2-[pyridin-3-yl-(tetrahydropyran-2-yloxy)-methyl]-pyran-4-one (Example 6c). The reaction mixture is heated for one hour at 40° C. and then for 24 hours under reflux. For working-up, the reaction mixture is concentrated to dryness by evaporation using a rotary evaporator. The residue is chromatographed on 75 g of silica gel. A mixture of ethyl acetate and ethanol in a ratio of 6/1 is used as eluant. 3-Benzyloxy-1-methyl-2-[pyridin-3-yl-(tetrahydropyran-2-yloxy)-methyl]-1H-pyridin-4-one is obtained in the form of a yellow foam. Diastereoisomeric mixture, $R_f$ value: 0.09 (silica gel 60, ethyl acetate/ethanol 6/1).

b) 3-Benzyloxy-2-(hydroxy-pyridin-3-yl-methyl)-1-methyl-1H-pyridin-4-one: 2.45 g of 3-benzyloxy-1-methyl-2-[pyridin-3-yl-(tetrahydropyran-2-yloxy)-methyl]-1H-pyridin-4-one are left to stand for 20 hours at room temperature in a mixture of 10 ml of ethanol and 10 ml of 2N HCl. The ethanol is removed using a rotary evaporator and the aqueous solution that remains is neutralised with excess aqueous sodium hydrogen carbonate solution. The resulting product is extracted twice with 50 ml of ethyl acetate each time. The organic phases are washed twice with 20 ml of water each time. The organic phases are combined, dried over magnesium sulfate and filtered and the filtrate is concentrated to dryness by evaporation using a rotary evaporator. Recrystallisation from ethyl acetate yields 3-benzyloxy-2-(hydroxy-pyridin-3-yl-methyl)-1-methyl-1H-pyridin-4-one. Light-beige crystals, m.p.: 169°–174° C.

EXAMPLE 8

4-[3-Hydroxy-2-(hydroxy-phenyl-methyl)-4-oxo-4H-pyridin-1-yl]-butyric acid

Catalytic hydrogenation of 0.733 g of 4-[3-benzyloxy-2-(hydroxy-phenyl-methyl)-4-oxo-4H-pyridin-1-yl]-butyric acid analogously to Example 1 and recrystallisation from methanol yield: 4-[3-hydroxy-2-(hydroxy-phenyl-methyl)-4-oxo-4H-pyridin-1-yl]-butyric acid. Reddish crystals. M.p.: 192°–195° C.

The starting material can be prepared, for example, as follows:

a) 4-{3-Benzyloxy-4oxo-2-[phenyl-tetrahydropyran-2-yloxy)-methyl]-4H pyridin-1-yl}-butyric acid: 2.5 g of 3-benzyloxy-2-[phenyl-(tetrahydropyran-2-yloxy)-methyl]-pyran-4-one (Example 1b) and 2.57 g of 4-aminobutyric acid [CAS No.: 56-12-2] are stirred for 12 hours at 120° C. in a mixture of 10 ml of tributylamine and 5 ml of ethylene glycol. The reaction mixture is then poured into 100 ml of water and adjusted to pH 5 with dilute hydrochloric acid. The resulting product is extracted twice with 50 ml of ethyl acetate each time. The organic phases are washed twice with 20 ml of water each time. The organic phases are combined, dried over magnesium sulfate and filtered and the filtrate is concentrated to dryness by evaporation using a rotary evaporator. Recrystallisation from ethyl acetate yields 4-{3-benzyloxy-4-oxo-2-[phenyl-tetrahydropyran-2-yloxy)-methyl]-4H-pyridin-1-yl}-butyric acid. Diastereoisomeric mixture, colourless crystals. M.p.: 205°–210° C.

b) 4-[3-Benzyloxy-2-(hydroxy-phenyl-methyl)-4-oxo-4H-pyridin-1-yl]-butyric acid: 0.95 g of 4-{3-benzyloxy-4-oxo-2-[phenyl-tetrahydropyran-2-yloxy)-methyl]-4H-pyridin-1-yl}-butyric acid are boiled under reflux for 3 hours in a mixture of 10 ml of ethanol and 10 ml of 2N HCl. 15 ml of 2N NaOH are added and the ethanol is removed using a rotary evaporator. The solution that remains is diluted with 50 ml of water and extracted twice with 50 ml of ethyl acetate each time. The ethyl acetate phases are discarded. The aqueous alkaline phase is rendered acidic with 6 ml of 2N HCl and the resulting product is extracted twice with 50 ml of ethyl acetate each time. The organic phases are washed twice with 20 ml of water each time. The organic phases are combined, dried over magnesium sulfate and filtered and the filtrate is concentrated to dryness by evaporation using a rotary evaporator. Recrystallisation from methanol yields 4-[3-benzyloxy-2-(hydroxy-phenyl-methyl)-4-oxo-4H-pyridin-1-yl]-butyric acid. Colourless crystals, m.p.: 205°–210° C.

EXAMPLE 9

4-(2-Benzyl-3-hydroxy-4-oxo-4H-pyridin-1-yl)-butyric acid

Hydrogenation of 1.2 g of 4-[2-(acetoxy-phenyl-methyl)-3-benzyloxy-4-oxo-4H-pyridin-1-yl]-butyric acid analogously to Example 2 and recrystallisation from ethanol yield 4-(2-benzyl-3-hydroxy-4-oxo-4H-pyridin-1-yl)-butyric acid. Beige crystals, m.p.: 170°–172° C.

The starting material can be prepared, for example, as follows:

a) 4-[2-(Acetoxy-phenyl-methyl)-3-benzyloxy-4-oxo-4H-pyridin-1-yl]-butyric acid: At room temperature, 1.28 g of 4-[3-benzyloxy-2-(hydroxy-phenyl-methyl)-4-oxo-4H-pyridin-1-yl]-butyric acid (Example 8b) are suspended in 60 ml of dichloromethane. 1.1 ml of pyridine and 0.48 ml of acetic anhydride are added. 0.05 g of 4-dimethyl-aminopyridine [CAS No.: 1122-58-3] is added and the reaction mixture is then stirred at room temperature for 18 hours. For working-up, the reaction mixture is washed once with 10 ml of 2N HCl and three times with 10 ml of water. The organic phase is dried over magnesium sulfate and filtered. The filtrate is concentrated by evaporation using a rotary evaporator, yielding 4-[2-(acetoxy-phenyl-methyl)-3-benzyloxy-4-oxo-4H-pyridin-1-yl]-butyric acid. Beige, amorphous foam. $R_f$ value 0.22 (silica gel 60, dichloromethane/ethanol 4/1).

EXAMPLE 10

3-Hydroxy-1-[2-(2-hydroxy-ethoxy)-ethyl]-2-(hydroxy-phenyl-methyl)-1H-pyridin-4-one From 2.04 g of 3-benzyloxy-1-[2-(2-hydroxy-ethoxy)-ethyl]-2-(hydroxy-phenyl-methyl)-1H-pyridin-4-one there is obtained analogously to Example 1: 3-hydroxy-1-[2-(2-hydroxy-ethoxy)-ethyl]-2-(hydroxy-phenyl-methyl)-1H-pyridin-4-one. Colourless crystals, m.p.: 157°–159° C.

The starting material can be prepared, for example, as follows:

a) 3-Benzyloxy-1-[2-(2-hydroxy-ethoxy)-ethyl]-2-[phenyl-(tetrahydropyran-2-yloxy)-methyl]-1H-pyridin-4-one:

From 3-benzyloxy-2-[phenyl-(tetrahydropyran-2-yloxy)-methyl]-pyran-4-one (Example 1b) there is obtained analogously to Example 1c: 3-benzyloxy-1-[2-(2-hydroxy-ethoxy)-ethyl]-2-[phenyl-(tetrahydropyran-2-yloxy)-methyl]-1H-pyridin-4-one. Diastereoisomeric mixture, $R_f$ value 0.08 (silica gel 60, ethyl acetate/ethanol 6/1).

b) 3-Benzyloxy-1-[2-(2-hydroxy-ethoxy)-ethyl]-2-(hydroxy-phenyl-methyl)-1H-pyridin-4-one: From 2.8 g of 3-benzyloxy-1-[2-(2-hydroxy-ethoxy)-ethyl]-2-[phenyl-(tetrahydropyran-2-yloxy)-methyl]-1H-pyridin-4-one there is obtained analogously to Example 1d: 3-benzyloxy-1-[2-(2-hydroxy-ethoxy)-ethyl]-2-(hydroxy-phenyl-methyl)-1H-pyridin-4-one. Colourless crystals, m.p.: 151°–152° C.

EXAMPLE 11

3-Hydroxy-1-(2-hydroxy-ethyl)-2-[hydroxy-(4-hydroxy-3-methoxy-phenyl)-methyl]-1H-pyridin-4-one Under normal pressure and at room temperature, 1.1 g of 3-benzyloxy-2-[(4-benzyloxy-3-methoxy-phenyl)-hydroxy-methyl]-1-(2-hydroxy-ethyl)-1H-pyridin-4-one are hydrogenated in 50 ml of methanol over 0.2 g of palladium on carbon (5%) until 2 mol of $H_2$ per mol of starting material have been taken up. Removal of the catalyst and recrystallisation from ethanol yield 3-hydroxy-1-(2-hydroxy-ethyl)-2-[hydroxy-(4-hydroxy-3-methoxy-phenyl)-methyl]-1H-pyridin-4-one. M.p.: 179°–190° C.

The starting material can be prepared, for example, as follows:

a) 2-[(4-Benzyloxy-3-methoxy-phenyl)-hydroxy-methyl]-3-hydroxy-pyran-4-one: From 3.36 g of pyromeconic acid and 7.27 g of 3-methoxy-4-benzyloxy-benzaldehyde there is obtained analogously to Example 3a: 2-[(4-benzyloxy-3-methoxy-phenyl)-hydroxy-methyl]-3-hydroxy-pyran-4-one. M.p.: crystal transformation from 142° C., decomposition from 190° C.

b) 3-Benzyloxy-2-[(4-benzyloxy-3-methoxy-phenyl)-hydroxy-methyl]-pyran-4-one: From 3.74 g of 2-[(4-benzyloxy-3-methoxy-phenyl)-hydroxy-methyl]-3-hydroxy-pyran-4-one there is obtained analogously to Example 1a: 3-benzyloxy-2-[(4-benzyloxy-3-methoxy-phenyl)-3-methoxy-phenyl)-hydroxy-methyl]-pyran-4-one. M.p.: 116°–117° C.

c) 3-Benzyloxy-2-[(4-benzyloxy-3-methoxy-phenyl)-(tetrahydropyran-2-yloxy)-methyl]-pyran-4-one: From 3-benzyloxy-2-[(4-benzyloxy-3-methoxy-phenyl)-hydroxy-methyl]-pyran-4-one there is obtained analogously to Example 6c: 3-benzyloxy-2-[(4-benzyloxy-3-methoxy-phenyl)-(tetrahydropyran-2-yloxy)-methyl]-pyran-4-one. Diastereoisomeric mixture, $R_f$ value 0.8 (silica gel 60, ethyl acetate/dichloromethane 1/1).

d) 3-Benzyloxy-2-[(4-benzyloxy-3-methoxy-phenyl)-(tetrahydropyran-2-yloxy)-methyl]-1-(2-hydroxy-ethyl)-1H-pyridin-4-one: From 3-benzyloxy-2-[(4-benzyloxy-3-methoxy-phenyl)-(tetrahydropyran-2-yloxy)-methyl]-pyran-4-one there is obtained analogously to Example 1c: 3-benzyloxy-2-[(4-benzyloxy-3-methoxy-phenyl)-(tetrahydropyran-2-yloxy)-methyl]-1-(2-hydroxy-ethyl)-1H-pyridin-4-one. Diastereoisomeric mixture, $R_f$ value 0.18 (silica gel 60, ethyl acetate/ethanol 9/1).

e) 3-Benzyloxy-2-[(4-benzyloxy-3-methoxy-phenyl)-hydroxy-methyl]-1-(2-hydroxy-ethyl)-1H-pyridin-4-one: From 1.58 g of 3-benzyloxy-2-[(4-benzyloxy-3-methoxy-phenyl)-(tetrahydro-pyran-2-yloxy)-methyl]-1-(2-hydroxy-ethyl)-1H-pyridin-4-one there is obtained analogously to Example 6b after recrystallisation from ethyl acetate: 3-benzyloxy-2-[(4-benzyloxy-3-methoxy-phenyl)-hydroxy-methyl]-1-(2-hydroxy-ethyl)-1H-pyridin-4-one. Colourless crystals, m.p.:172°–173° C.

EXAMPLE 12

3-Hydroxy-1-(2-hydroxy-ethyl)-6-hydroxymethyl-2-(hydroxy-phenyl-methyl)-1H-pyridin-4-one Hydrogenation of 0.834 g of 3-benzyloxy-1-(2-hydroxy-ethyl)-6-hydroxymethyl-2-(hydroxy-phenyl-methyl)-1H-pyridin-4-one analogously to Example 1 yields 3-hydroxy-1-(2-hydroxy-ethyl)-6-hydroxymethyl-2-(hydroxy-phenyl-methyl)-1H-pyridin-4-one in the form of an amorphous foam. $R_f$ value 0.15 (silica gel 60, ethyl acetate/ethanol 6/1).

The starting material can be prepared, for example, as follows:

a) 3-Hydroxy-6-hydroxymethyl-2-(hydroxy-phenyl-methyl)-pyran-4-one: From 2.82 g of kojic acid [CAS No.: 501-30-4] and 2.33 g of benzaldehyde there is obtained analogously to Example 3a: 3-hydroxy-6-hydroxymethyl-2-(hydroxy-phenyl-methyl)-pyran-4-one. M.p.: 148–149.5° C.

b) 3-Benzyloxy-6-hydroxymethyl-2-(hydroxy-phenyl-methyl)-pyran-4-one: From 3-hydroxy-6-hydroxymethyl-2-(hydroxy-phenyl-methyl)-pyran-4-one there is obtained analogously to Example 6b: 3-benzyloxy-6-hydroxymethyl-2-(hydroxy-phenyl-methyl)-pyran-4-one. Yellow resin, $R_f$ value 0.57 (silica gel 60, ethyl acetate/ethanol 9/1).

c) 3-Benzyloxy-6-methoxymethoxymethyl-2-(methoxymethoxy-phenyl-methyl)-pyran-4-one: 7.0 g of 3-benzyloxy-6-hydroxymethyl-2-(hydroxy-phenyl-methyl)-pyran-4-one are dissolved in 15 ml of dimethoxymethane and 150 ml of dichloromethane. 0.2 g of p-toluenesulfonic acid is added and the solution is boiled under reflux for 48 hours over an extraction thimble filled with molecular sieve (5 Å). After cooling, washing is carried out once with 20 ml of saturated sodium hydrogen carbonate solution and twice with 20 ml of water each time. The reaction mixture is dried over magnesium sulfate and filtered and then concentrated to dryness by evaporation. The residue consists of approximately 80% 3-benzyloxy-6-methoxymethoxymethyl-2-(methoxymethoxy-phenyl-methyl)-pyran-4-one. $R_f$ value 0.55 (silica gel 60, ethyl acetate/ethanol 98/2).

d) 3-Benzyloxy-1-(2-hydroxy-ethyl)-6-methoxymethoxymethyl-2-(methoxymethoxy-phenyl-methyl)-1H-pyridin-4-one: From 3-benzyloxy-6-methoxymethoxymethyl-2-(methoxymethoxy-phenyl-methyl)-pyran-4-one there is obtained analogously to Example 1c: 3-benzyloxy-1-(2-hydroxy-ethyl)-6-methoxymethoxymethyl-2-(methoxymethoxy-phenyl-methyl)-1H-pyridin-4-one. Brown resin, $R_f$ value 0.36 (silica gel 60, ethyl acetate/ethanol 6/1).

e) 3-Benzyloxy-1-(2-hydroxy-ethyl)-6-hydroxymethyl-2-(hydroxy-phenyl-methyl)-1H-pyridin-4-one: From 2.1 g of 3-benzyloxy-1-(2-hydroxy-ethyl)-6-methoxymethoxymethyl-2-(methoxy-methoxy-phenyl-methyl)-1H-pyridin-4-one there is obtained analogously to Example 6e, after recrystallisation from dichloromethane: 3-benzyloxy-1-(2-hydroxy-ethyl)-6-hydroxymethyl-2-(hydroxy-phenyl-methyl)-1H-pyridin-4-one. M.p.: crystal transformation from 166° C., then 189°–191° C.

EXAMPLE 13

1-(2,3-Dihydroxy-propyl)-3-hydroxy-2-(hydroxy-phenyl-methyl)-1H-pyridin-4-one

Hydrogenation of 1.63 g of 3-benzyloxy-1-(2,3-dihydroxy-propyl)-2-(hydroxy-phenyl-methyl)-1H-pyridin-4-one analogously to Example 1 yields 1-(2,3-dihydroxy-propyl)-3-hydroxy-2-(hydroxy-phenyl-methyl)-1H-pyridin-4-one in the form of a colourless amorphous foam. Diastereoisomeric mixture, $R_f$ value 0.15 (silica gel 60, dichloromethane/ethanol 4/1).

The starting material can be prepared, for example, as follows:

a) 3-Benzyloxy-1-(2,3-dihydroxy-propyl)-2-[phenyl-(tetrahydropyran-2-yloxy)methyl]-1H-pyridin-4-one: 3.93 g of 3-benzyloxy-2-[phenyl-(tetrahydropyran-2-yloxy)-methyl]-pyran-4-one (Example 1b) and 3 g of 3-amino-1,2-propanediol [CAS No.: 616-30-8] are stirred together at 110° C. for 17 hours. 50 ml of water and 20 ml of ethyl acetate are added to the melt. At room temperature, fine needles of a pale-yellow product crystallise out. The crystals are filtered off and washed with water and ethyl acetate. Drying yields 3-benzyloxy-1-(2,3-dihydroxy-propyl)-2-[phenyl-(tetrahydropyran-2-yloxy)methyl]-1H-pyridin-4-one in the form of a diastereoisomeric mixture. M.p.: 198°–215° C. The above flitrate is separated in a separating funnel. The organic phase is washed twice with water and concentrated to dryness by evaporation using a rotary evaporator. The residue is recrystallised from 20 ml of ethyl acetate and, after drying, further 3-benzyloxy-1-(2,3-dihydroxy-propyl)-2-[phenyl-(tetrahydropyran-2-yloxy)methyl]-1H-pyridin-4-one is obtained. Yellow cuboid crystals. Diastereoisomeric mixture. M.p.: 190°–206° C.

b) 3-Benzyloxy-1-(2,3-dihydroxy-propyl)-2-(hydroxy-phenyl-methyl)-1H-pyridin-4-one: From 2.1 g of 3-benzyloxy-1-(2,3-dihydroxy-propyl)-2-[phenyl-(tetrahydropyran-2-yloxy)methyl]-1H-pyridin-4-one there is obtained analogously to Example 6e, after chromatography: 3-benzyloxy-1-(2,3-dihydroxy-propyl)-2-(hydroxy-phenyl-methyl)-1H-pyridin-4-one. Colourless foam, diastereoisomeric mixture. $R_f$ value 0.22 (silica gel 60, dichloromethane/ethanol 4/1).

EXAMPLE 14

2-Benzyl-1-(2,3-dihydroxy-propyl)-3-hydroxy-1H-pyridin-4-one

From 0.6 g of 3-benzyloxy-1-(2,3-dihydroxy-propyl)-2-(hydroxy-phenyl-methyl)-1H-pyridin-4-one (Example 13b) there is obtained analogously to Example 2: 2-benzyl-1-(2,3-dihydroxy-propyl)-3-hydroxy-1H-pyridin-4-one. Crystallisation from methanol, m.p.: 185°–186° C.

EXAMPLE 15

N-(2-Hydroxy-ethyl)-4-{hydroxy-[3-hydroxy-1-(2-hydroxy-ethyl)-4-oxo-1,4-dihydro-pyridin-2-yl]-methyl}-benzamide From 1.18 g of 4-{[3-benzyloxy-1-(2-hydroxy-ethyl)-4-oxo-1,4-dihydro-pyridin-2-yl]-hydroxy-methyl}-N-(2-hydroxy-ethyl)-benzamide monohydrate there is obtained analogously to Example 1: N-(2-hydroxy-ethyl)-4-{hydroxy-[3-hydroxy-1-(2-hydroxy-ethyl)-4-oxo-1,4-dihydro-pyridin-2-yl]-methyl}-benzamide. Pink-coloured, amorphous foam, $R_f$ value 0.05 (silica gel 60, dichloromethane/ethanol 4/1).

The starting material can be prepared, for example, as follows:

a) 4-[Hydroxy-(3-hydroxy-4-oxo-4H-pyran-2-yl)-methyl]-benzoic acid: 4.48 g of pyromeconic acid and 7.51 g of 4-carboxybenzaldehyde [CAS No.: 619-66-9] are dissolved in 8 ml of water, 43 ml of 2N NaOH and 15 ml of methanol. The brown solution has a pH of 10. The solution is left to stand at room temperature for 18 hours. The methanol is removed using a rotary evaporator and the aqueous solution that remains is neutralised with 43 ml of 2N HCl. The product that precipitates is filtered off and dried, yielding 4-[hydroxy-(3-hydroxy-4-oxo-4H-pyran-2-yl)-methyl]-benzoic acid. M.p.: from 184° C. with decomposition.

b) 4-[(3-Benzyloxy-4-oxo-4H-pyran-2-yl)-hydroxy-methyl] benzoic acid benzyl ester: 10.5 g of 4-[hydroxy-(3-hydroxy-4-oxo-4H-pyran-2-yl)-methyl]-benzoic acid and 22 g of powdered potassium carbonate are stirred in 120 ml of dimethylformamide at room temperature. 14 g of benzyl bromide are added and the suspension is stirred at room temperature for 18 hours. For working-up, the suspension is poured into 500 ml of water and extracted twice with 200 ml of ethyl acetate each time. The organic phases are washed four times with 50 ml of water each time, combined and dried over magnesium sulfate. The drying agent is removed by filtration and the filtrate is concentrated by evaporation using a rotary evaporator. Chromatography yields 4-[(3-benzyloxy-4-oxo-4H-pyran-2-yl)-hydroxy-methyl]benzoic acid benzyl ester. Yellow oil, $R_f$ value 0.19 (silica gel 60, hexane/dichloromethane/ethyl acetate 1/1/1).

c) 4-[(3-Benzyloxy-4-oxo-4H-pyran-2-yl)-(tetrahydropyran-2-yloxy)-methyl]-benzoic acid benzyl ester: From 4-[(3-benzyloxy-4-oxo-4H-pyran-2-yl)-hydroxy-methyl]-benzoic acid benzyl ester there is obtained analogously to Example 6c: 4-[(3-benzyloxy-4-oxo-4H-pyran-2-yl)-(tetrahydropyran-2-yloxy)-methyl]-benzoic acid benzyl ester. Yellow resin, $R_f$ value 0.57 (silica gel 60, hexane/dichloromethane/ethyl acetate 1/1/1).

d) 4-{[3-Benzyloxy-1-(2-hydroxy-ethyl)-4-oxo-1,4-dihydro-pyridin-2-yl]-(tetrahyodropyran-2-yl-oxy)-methyl}-N-(2-hydroxy-ethyl)-benzamide: Reaction of 4-[(3-benzyloxy-4-oxo-4H-pyran-2-yl)-(tetrahydropyran-2-yloxy)-methyl]-benzoic acid benzyl ester analogously to Example 1c yields: 4-{[3-benzyloxy-1-(2-hydroxy-ethyl)-4-oxo-1,4-dihydro-pyridin-2-yl]-(tetrahydropyran-2-yloxy)-methyl}-N-(2-hydroxy-ethyl)-benzamide in the form of a diastereoisomeric mixture. Yellow resin, $R_f$ value 0.19 (silica gel 60, dichloromethane/ethanol 4/1).

e) 4-{[3-Benzyloxy-1-(2-hydroxy-ethyl)-4-oxo-1,4-dihydro-pyridin-2-yl]-hydroxy-methyl}-N-(2-hydroxy-ethyl)-benzamide: 2.25 g of 4-{[3-benzyloxy-1-(2-hydroxy-ethyl)-4-oxo-1,4-dihydro-pyridin-2-yl]-(tetrahydropyran-2-yloxy)-methyl}-N-(2-hydroxy-ethyl)-benzamide are boiled under reflux for 90 minutes in 15 ml of methanol and 5.5 ml of 2N HCl. The methanol is removed using a rotary evaporator and the residue is neutralised with excess aqueous sodium hydrogen carbonate solution. The resulting product is extracted twice with 50 ml of ethyl acetate each time. The organic phases are washed twice with 20 ml of water each time. The organic phases are combined, dried over magnesium sulfate and filtered and the flitrate is concentrated to dryness by evaporation using a rotary evaporator. Recrystallisation from water yields 4-{[3-benzyloxy-1-(2-hydroxy-ethyl)-4-oxo-1,4-dihydro-pyridin-2-yl]- hydroxy-methyl}-N-(2-hydroxy-ethyl)-benzamide in the form of the monohydrate. M.p.: from 108° C. with decomposition to 227° C.

EXAMPLE 16

[3-Hydroxy-2-(hydroxy-phenyl-methyl)-4-oxo-4H-pyridin-1-yl]-acetic acid

Catalytic hydrogenation of 1.02 g of [3-benzyloxy-2-(hydroxy-phenyl-methyl)-4-oxo-4H-pyridin-1-yl]-acetic acid sodium salt tetrahydrate analogously to Example 1, and recrystallisation from methanol, yields: [3-hydroxy-2-(hydroxy-phenyl-methyl)-4-oxo-4H-pyridin-1-yl]-acetic acid in the form of the sodium salt dihydrate. Light-beige crystals. M.p.: loss of water of crystallisation from 120° C., decomposition from 300° C.

The starting material can be prepared, for example, as follows:

a) {3-Benzyloxy-4-oxo-2-[phenyl-(tetrahydropyran-2-yloxy)-methyl]-4H-pyridin-1-yl}-acetic acid ethyl ester: 2.5 g of 3-benzyloxy-2-[phenyl-(tetrahydropyran-2-yloxy)-methyl]-pyran-4-one (Example 1b) and 3.5 g of glycine ethyl ester hydrochloride [CAS No.: 623-33-6] are stirred in a mixture of 25 ml of tributylamine and 5 ml of ethylene glycol at 110° C. for 40 hours. 200 ml of water are added and the pH is adjusted to 4 with dilute hydrochloric acid. Extraction is carried out twice with 100 ml of ethyl acetate each time. The organic phases are washed three times with 50 ml of water each time, dried over magnesium sulfate, filtered and concentrated by evaporation. Chromatography yields {3-benzyloxy-4-oxo-2-[phenyl-(tetrahydropyran-2-yloxy)-methyl]-4H-pyridin-1-yl}-acetic acid ethyl ester. Yellow resin. $R_f$ value 0.25 (silica gel 60, dichloromethane/ethanol 9/1).

b) [3-Benzyloxy-2-(hydroxy-phenyl-methyl)-4-oxo-4H-pyridin-1-yl]-acetic acid ethyl ester: Treatment of 1.3 g of {3-benzyloxy-4-oxo-2-[phenyl-(tetrahydropyran-2-yloxy)-methyl]-4H-pyridin-1-yl}-acetic acid ethyl ester with 2N HCl and ethanol and chromatography analogously to Example 6e yield [3-benzyloxy-2-(hydroxy-phenyl-methyl)-4-oxo-4H-pyridin-1-yl]-acetic acid ethyl ester in the form of a yellowish resin. $R_f$ value 0.4 (silica gel 60, dichloromethane/ethanol 9/1).

c) [3-Benzyloxy-2-(hydroxy-phenyl-methyl)-4-oxo-4H-pyridin-1-yl]-acetic acid: At room temperature, 1.2 g of [3-benzyloxy-2-(hydroxy-phenyl-methyl)-4-oxo-4H-pyridin-1-yl]-acetic acid ethyl ester are dissolved in 5 ml of 2N NaOH and 1 ml of ethanol. The reaction mixture is left to stand for 20 hours at room temperature and then cooled for one hour in an ice-bath. The reaction mixture is filtered and washed with a small amount of ice-water. Drying at room temperature yields [3-benzyloxy-2-(hydroxy-phenyl-methyl)-4-oxo-4H-pyridin-1-yl]-acetic acid in the form of the sodium salt tetrahydrate. Colourless flakes. M.p.: after crystal transformation at 85°–95° C., 190°–195° C.

EXAMPLE 17

4-{2-[(4-Fluoro-phenyl)-hydroxy-methyl]-3-hydroxy-4-oxo-4H-pyridin-1-yl}-butyric acid Hydrogenation of 1.9 g of 4-{3-benzyloxy-2-[(4-fluoro-phenyl)-hydroxy-methyl]-4-oxo-4H-pyridin-1-yl}-butyric acid analogously to Example 1 and recrystallisation from methanol yield: 4-{2-[(4-fluoro-phenyl)-hydroxy-methyl]-3-hydroxy-4-oxo-4H-pyridin-1-yl}-butyric acid. pink crystals, m.p.: 177.5°–178° C.

The starting material can be prepared, for example, as follows:

a) 4-{3-Benzyoxy-2-[(4fluro-phenyl)-(tetrahydropyran-2-yloxy)-methyl]-4oxo-4H-pyridin-1-yl}-butyric acid: Reaction of 4.1 g of 3-benzyloxy-2-[(4-fluorophenyl)-(tetrahydropyran-2-yloxy)-methyl]-pyran-4-one (Example 3c) with 4-aminobutyric acid analogously to Example 8a yields: 4-{3-benzyloxy-2-[(4-fluoro-phenyl)-(tetrahydropyran-2-yloxy)-methyl]-4-oxo-4H-pyridin-1-yl}-butyric acid in the form of a diastereoisomeric mixture. Beige crystals, m.p.: 187°–190° C.

b) 4-{3-Benzyloxy-2-[(4-fluoro-phenyl)-hydroxy-methyl]-4-oxo-4H-pyridin-1-yl}-butyric acid: From 1.0 g of 4-{3-benzyloxy-2-[(4-fluoro-phenyl)-(tetrahydropyran-2-yloxy)-methyl]-4-oxo- 4H-pyridin-1-yl}-butyric acid there is obtained analogously to Example 8b: 4-{3-benzyloxy-2-[(4-fluoro-phenyl)-hydroxy-methyl]-4-oxo-4H-pyridin-1-yl}-butyric acid. Colourless crystals. M.p.: 215°–220° C.

EXAMPLE 18

{2-[(4-Fluoro-phenyl)-hydroxy-methyl]-3-hydroxy-4-oxo-4H-pyridin-1-yl}-acetic acid Hydrogenation of 1.47 g of {3-benzyloxy-2-[(4-fluoro-phenyl)-hydroxy-methyl]-4-oxo-4H-pyridin-1-yl}-acetic acid analogously to Example 1 and recrystallisation from ethyl acetate yield: (2-[(4-fluoro-phenyl)-hydroxy-methyl]-3-hydroxy-4-oxo-4H-pyridin-1-yl)-acetic acid. Colourless crystals, m.p.: 123°–127° C.

The starting material can be prepared, for example, as follows:

a) {3-Benzyloxy-2-[{4-fluoro-phenyl}-(tetrahydropyran-2-yloxy)-methyl]-4-oxo-4H-pyridin-1-yl}-acetic acid: 5.54 g of 3-benzyloxy-2-[(4-fluorophenyl)-(tetrahydropyran-2-yloxy)-methyl]-pyran-4-one (Example 3c) and 4.5 g of glycine are stirred in a mixture of 55 ml of diethylene glycol and 30 ml of tri-n-butylamine at 110° C. for 48 hours. The reaction mixture is diluted with 100 ml of water and 75 ml of 2N HCl and extracted three times with 100 ml of ethyl acetate each time. The organic phases are washed three times with 50 ml of water each time. The organic phases are combined, dried over magnesium sulfate and filtered. The filtrate is concentrated to dryness by evaporation using a rotary evaporator. The residue that remains is crude {3-benzyloxy-2-[(4-fluoro-phenyl)-(tetrahydropyran-2-yloxy)-methyl]-4-oxo-4H-pyridin-1-yl}-acetic acid in the form of a diastereoisomeric mixture. $R_f$ value 0.12 (silica gel 60, dichloromethane/ethanol 4/1).

b) {3-Benzyloxy-2-[(4-fluoro-phenyl)-hydroxy-methyl]-4-oxo-4H-pyridin-1-yl}-acetic acid: Treatment of 6.0 g of crude {3-benzyloxy-2-[(4-fluoro-phenyl)-(tetrahydropyran-2-yloxy)-methyl]-4-oxo-4H-pyridin-1-yl}-acetic acid with dilute hydrochloric acid analogously to Example 8b yields: {3-benzyloxy-2-[(4-fluoro-phenyl)-hydroxy-methyl]-4-oxo-4H-pyridin-1-yl}-acetic acid. Colourless crystals. M.p.: 147°–150° C.

EXAMPLE 19

N-{2-[3-Hydroxy-2-{hydroxy-phenyl-methyl)-4-oxo-4H-pyridin-1-yl]-ethyl}-acetamide Hydrogenation of 0.389 g of N-{2-[3-benzyloxy-2-(hydroxy-phenyl-methyl)-4-oxo-4H-pyridin-1-yl]-ethyl}-acetamide analogously to Example 1 and crystallisation from ether yield N-{2-[3-hydroxy-2-(hydroxy-phenylmethyl)-4-oxo-4H-pyridin-1-yl]-ethyl}-acetamide. Beige crystals, m.p.: 187.5°–190° C.

The starting material can be prepared, for example, as follows:

a) 1-(2-Amino-ethyl)-3-benzyloxy-2-[phenyl-(tetrahydrodyran-2-yloxy}-methyl]-1H-pyridin-4-one.: 6.5 g of 3-benzyloxy-2-[phenyl-(tetrahydropyran-2-yloxy)-methyl]-pyran-4-one (Example 1b) are boiled under reflux for 8 hours, together with 13 ml of ethylenediamine, in 65 ml of ethanol. Working-up analogously to Example 1c yields 1-(2-amino-ethyl)-3-benzyloxy-2-[phenyl-(tetrahydropyran-2-yloxy)-methyl]-1H-pyridin-4-one in the form of a diastereoisomeric mixture. $R_f$ value 0.2 (silica gel 60, dichloromethane/ethanol 4/1).

b) N-2-{3-Benzyloxy-4-oxo-2-[phenyl-(tetrahydropyran-2-yloxy)-methyl4-4H-pyridin-1-yl}-ethyl)-acetamide: 2.6 g of crude 1-(2-amino-ethyl)-3-benzyloxy-2-[phenyl-(tetrahydropyran-2-yloxy)-methyl]-1H-pyridin-4-one are dissolved in 50 ml of dichloromethane. At room temperature, 3.5 ml of Hünig base [CAS No.: 7087-68-5] and then 0.85 ml of acetic anhydride are added. The solution is left to stand at room temperature for 18 hours and then washed once with 10 ml of 1N HCl and twice with 10 ml of water each time. The organic phase is dried over magnesium sulfate and filtered. The flitrate is concentrated to dryness by evaporation using a rotary evaporator. The residue is chromatographed on silica gel. A mixture of ethyl acetate and ethanol in a ratio of 6/1 is used as eluant. N-(2-{3-Benzyloxy-4-oxo-2-[phenyl-(tetrahydropyran-2-yloxy)-methyl]-4-4H-pyridin-1-yl}-ethyl)-acetamide is obtained in the form of a brown resin. $R_f$ value: 0.5 (silica gel 60, dichloromethane/ethanol 4/1).

c) N-{2-[3-Benzyloxy-2-(hydroxy-phenyl-methyl)-4-oxo-4H-pyridin-1-yl]-ethyl}-acetamide: 0.33 g of N-(2-{3-benzyloxy-4-oxo-2-[phenyl-(tetrahydropyran-2-yloxy)-methyl]-4-4H-pyridin-1-yl}-ethyl)-acetamide is dissolved in 3.5 ml of methanol, and 0.69 ml of 2N HCl is added. The solution is heated at 40° C. for 18 hours. An excess of aqueous sodium hydrogen carbonate solution is added and extraction is carried out three times with 50 ml of ethyl acetate each time. The extracts are washed three times with 10 ml of water each time and the organic phases are combined and dried over magnesium sulfate. Filtration is carried out and the flitrate is concentrated to dryness by evaporation using a rotary evaporator. The residue is crystallised from ethyl acetate to yield N-{2-[3-benzyloxy-2-(hydroxy-phenyl-methyl)-4-oxo-4H-pyridin-1-yl]-ethyl}-acetamide. Beige crystals, m.p.: 180°–182° C.

EXAMPLE 20

1-(2-Dimethylamino-ethyl)-3-hydroxy-2-(hydroxy-phenyl-methyl)-1H-pyridin-4-one

Hydrogenation of 1.97 g of 3-benzyloxy-1-(2-dimethylamino-ethyl)-2-(hydroxy-phenyl-methyl)-1H-pyridin-4-one analogously to Example 1 and crystallisation from methanol yield: 1-(2-dimethylamino-ethyl)-3-hydroxy-2-(hydroxy-phenyl-methyl)-1H-pyridin-4-one. Colourless crystals, m.p.: 186°–188° C.

The starting material can be prepared, for example, as follows:

a) 3-Benzyloxy-1-(2-dimethylamino-ethyl)-2-[phenyl-(tetrahydropyran-2-yloxy)-methyl]-1H-pyridin-4-one: Reaction of 3-benzyloxy-2-[phenyl-(tetrahydropyran-2-yloxy)-methyl]-pyran-4-one (Example 1b) with 2-dimethylamino-ethylamine [CAS No.: 108-00-9] analogously to Example 18a yields 3-benzyloxy-1-(2-dimethylamino-ethyl)-2-[phenyl-(tetrahydropyran-2-yloxy)-methyl]-1H-pyridin-4-one in the form of a diastereoisomeric mixture. Brown resin. $R_f$ value: 0.44 (silica gel 60, dichloromethane/ethanol 4/1).

b) 3-Benzyloxy-1-(2-dimethylamino-ethyl)-2-(hydroxy-phenyl-methyl)-1H-pyridin-4-one: From 5.2 g of 3-benzyloxy-1-(2-dimethylamino-ethyl)-2-[phenyl-(tetrahydropyran-2-yloxy)-methyl]-1H-pyridin-4-one there is obtained analogously to Example 6e, after chromatography: 3-benzyloxy-1-(2-dimethylamino-ethyl)-2-(hydroxy-phenyl-methyl)-1H-pyridin-4-one. Beige, amorphous foam. $R_f$ value: 0.16 (silica gel 60, dichloromethane/ethanol 4/1).

EXAMPLE 21

2-(Hydroxy-phenyl-methyl)-pyridine-3,4-diol

Hydrogenation of 0.465 g of 3-benzyloxy-2-(hydroxy-phenyl-methyl)-pyridin-4-ol analogously to Example 1 yields: 2-(hydroxy-phenyl-methyl)-pyridine-3,4-diol. Colourless crystals. M.p.: from 200° C. with decomposition.

The starting material can be prepared, for example, as follows:

a) 3-Benzyloxy-2-[phenyl-(tetrahydropyran-2-yloxy)-methyl]-pyridin-4-ol: At room temperature, 100 ml of a solution of ammonia in methanol (6M) is poured over 5 g of 3-benzyloxy-2-[phenyl-(tetrahydropyran-2-yloxy)-methyl]-pyran-4-one (Example 1b) and the reaction mixture is left to stand in a closed flask at room temperature for 6 days. The reaction mixture is concentrated to dryness by evaporation in vacuo and 100 ml of ether are added to the residue. The crystal suspension thus formed is filtered and the product is washed with ether and dried, yielding 3-benzyloxy-2-[phenyl-(tetrahydropyran-2-yloxy)-methyl]-pyridin-4-ol in the form of a diastereoisomeric mixture. Yellowish crystals, m.p.: 192°–192.5° C.

b) 3-Benzyloxy-2-(hydroxy-phenyl-methyl)-pyridin-4-ol: Treatment of 0.783 g of 3-benzyloxy-2-[phenyl-(tetrahydropyran-2-yloxy)-methyl]-pyridin-4-ol analogously to Example 1d yields: 3-benzyloxy-2-(hydroxy-phenyl-methyl)-pyridin-4-ol. Colourless crystals, m.p.: 215°–218° C. with decomposition, crystal transformation from 205° C.

EXAMPLE 22

2-[Hydroxy-(4-hydroxy-3-methoxy-phenyl)-methyl]-pyridine-3,4-diol 0.9 g of 3-benzyloxy-2-[(4-benzyloxy-3-methoxy-phenyl)-hydroxy-methyl]-pyridin-4-ol is dissolved in 100 ml of methanol and hydrogenated at room temperature in the presence of 0.18 g of palladium on carbon (5%) until 2 mol of $H_2$ per mol of starting material have been taken up. The catalyst is removed by filtration and the flitrate is concentrated by evaporation. Recrystallisation from methanol yields 2-[hydroxy-(4-hydroxy-3-methoxy-phenyl)-methyl]-pyridine-3,4-diol. Colourless crystals, m.p.: from 210° C. with decomposition.

The starting material can be prepared, for example, as follows:

a) 3-Benzyloxy-2-[(4-benzyloxy-3-methoxy-phenyl)-(tetrahydropyran-2-yloxyl)-methyl]-pydridin-4-ol: 3-Benzyloxy-2-[(4-benzyloxy-3-methoxy-phenyl)-(tetrahydropyran-2-yloxy)-methyl]-pyran-4-one (Example 11c) is reacted analogously to Example 21a to yield 3-benzyloxy-2-[(4-benzyloxy-3-methoxy-phenyl)-(tetrahydropyran-2-yloxy)-methyl]-pyfidin-4-ol in the form of a yellow resin. Diastereoisomeric mixture. $R_f$ value: 0.35 (silica gel 60, ethyl acetate/ethanol 9/1).

b) 3-Benzyloxy-2-[4-benzyloxy-3-methoxy-phenyl)-hydroxy-methyl]-pyridin-4-ol: Treatment of 3-benzyloxy-2-[(4-benzyloxy-3-methoxy-phenyl)-(tetrahydropyran-2-yloxy)-methyl]-pyridin- 4-ol analogously to Example 1d yields: 3-benzyloxy-2-[(4-benzyloxy-3-methoxy-phenyl)-hydroxy-methyl]-pyridin-4-ol. Colourless crystals. M.p.: 248°–252° C.

EXAMPLE 23

3-Hydroxy-1-methyl-2-(pyridine-3-carbonyl)-1H-pyridin-4-one

Hydrogenation of 1.35 g of 3-benzyloxy-1-methyl-2-(pyridine-3-carbonyl)-1H-pyridin-4-one analogously to Example 1 and crystallisation from ethyl acetate yields: 3-hydroxy-1-methyl-2-(pyridine-3-carbonyl)-1H-pyridin-4-one. Yellow crystals, m.p.: 210°–216° C.

The starting material can be prepared, for example, as follows:

a) 3-Benzyloxy-1-methyl-2-(pyridine-3-carbonyl)-1H-pyridin-4-one 2.2 g of 3-benzyloxy-2-(hydroxy-pyridin-3-yl-methyl)-1-methyl-1H-pyridin-4-one (Example 7b) are dissolved in 35 ml of dichloromethane and 7 ml of dimethyl sulfoxide. At room temperature, 4.9 ml of tri-ethylamine are added and, finally, 4.33 g of pyridine/ sulfur trioxide complex [CAS No.: 26412-87-3] are added to the solution. The solution is left to stand at room temperature for 8 days and then diluted with 50 ml of dichloromethane and extracted by shaking three times with 20 ml of water each time. The organic phase is dried over magnesium sulfate and filtered and concentrated to dryness by evaporation using a rotary evaporator. The residue is chromatographed on silica gel. A mixture of dichloromethane and ethanol in a ratio of 6/1 is used as eluant. 3-Benzyloxy-1-methyl-2-(pyridine-3-carbonyl)-1H-pyridin-4-one is obtained in the form of a yellow resin. $R_f$ value: 0.32 (silica gel 60, dichloromethane/ethanol 6/1).

EXAMPLE 24

3-Hydroxy-2-[pyridin-3-yl-(acetoxy)-methyl]-1-methyl-1H-pyridin-4-one 2.7 g of 3-benzyloxy-1-methyl-2-[pyridin-3-yl-(acetoxy)-methyl-1H-pyridin-4-one are dissolved in 50 ml of methanol and hydrogenated at room temperature over 0.6 g of palladium on carbon (5%) until 1 mol of $H_2$ per mol of starting material has been taken up. The catalyst is removed by filtration and the flitrate is concentrated to dryness by evaporation using a rotary evaporator. Recrystallisation from ethyl acetate yields 3-hydroxy-2-[pyridin-3-yl-(acetoxy)-methyl]-1-methyl-1H-pyridin-4-one. Pale-pink crystals, m.p.: 153°–154° C.

The starting material can be prepared, for example, as follows:

a) 3-Benzyloxy-1-methyl-2-[pyridin-3-yl-(acetoxy)-methyl-1H-pyridin-4-one: Acetylation of 3-benzyloxy-2-(hydroxy-pyridin-3-yl-methyl)-1-methyl-1H-pyridin-4-one (Example 7b) analogously to Example 9a yields 3-benzyloxy-1-methyl-2-[pyridin-3-yl-(acetoxy)-methyl-1H-pyridin-4-one in the form of a cloudy yellow resin. $R_f$ value: 0.37 (silica gel 60, dichloromethane/ethanol 4/1).

EXAMPLE 25

3-Hydroxy-1-methyl-2-pyridin-3-ylmethyl-1H-pyridin-4-one 2.83 g of 3-benzyloxy-1-methyl-2-[pyridin-3-yl-(acetoxy)-methyl-1H-pyridin-4-one (Example 24a) are dissolved in 50 ml of methanol and hydrogenated over 0.6 g of palladium on carbon (5%), initially at room temperature, until I mol ot $H_2$ per mol of starting material has been taken up. The temperature is then increased to 50° C. and hydrogenation is continued until a further mol of $H_2$ per mol of starting material has been taken up. The catalyst is removed by filtration and the flitrate is concentrated to dryness by evaporation using a rotary evaporator. Recrystallisation from ethanol/diethyl ether yields 3-hydroxy-1-methyl2-pyridin-3-ylmethyl-1H-pyridin-4-one. Colourless crystals, m.p.: 209°–212° C., crystal transformation from 188° C.

EXAMPLE 26

3-Hydroxy-1-(2-hydroxy-ethyl)-2-[hydroxy-(2-hydroxy-phenyl)-methyl]-1H-pyridin-4-one From 1.84 g of 3-benzyloxy-2-[(2-benzyloxy-phenyl)-hydroxy-methyl]-1-(2-hydroxy-ethyl)-1H-pyridin-4-one there is obtained analogously to Example 11: 3-hydroxy-1-(2-hydroxy-ethyl)-2-[hydroxy-(2-hydroxy-phenyl)-methyl]-1H-pyridin-4-one. Colourless crystals, m.p.: 196°–197° C.

The starting material can be prepared, for example, as follows:

a) 3-Hydroxy-2-[hydroxy-(2-hydroxy-Dhenyl)-methyl]-pyran-4-one: From 2.24 g of pyromeconic acid and 3.05 g of salicylaldehyde there is obtained analogously to Example 3a: 3-hydroxy-2-[hydroxy-(2-hydroxy-phenyl)-methyl]-pyran-4-one. $R_f$ value: 0.45 (silica gel 60, ethyl acetate/ethanol 95/5).

b) 3-Benzyloxy-2-[(2-benzyloxy-phenyl)-hydroxy-methyl]-pyran-4-one: From 4.22 g of 3-hydroxy-2-[hydroxy-(2-hydroxy-phenyl)-methyl]-pyran-4-one there is obtained analogously to Example 1a: 3-benzyloxy-2-[(2-benzyloxy-phenyl)-hydroxy-methyl]-pyran-4-one. Yellow crystals, m.p.: 144°–145.6° C.

c) 3-Benzyloxy-2-[(2-benzyloxy-phenyl)-(tetrahydropyran-2-yloxy)-methyl]-pyran-4-one: From 3-benzyloxy-2-[(2-benzyloxy-phenyl)-hydroxy-methyl]-pyran-4-one there is obtained analogously to Example 1b: 3-benzyloxy-2-[(2-benzyloxy-phenyl)-(tetrahydropyran-2-yloxy)-methyl]-pyran-4-one. Thick yellow oil. Diastereoisomeric mixture. $R_f$ values: 0.48 and 0.56 (silica gel 60, hexane/dichloromethane/ethyl acetate 1/1/1).

d) 3-Benzyloxy-2-[(2-benzyloxy-phenyl)-(tetrahydropyran-2-yloxy)-methyl]-1-(2-hydroxy-ethyl)-1H-pyridin-4-one: From 5.31 g of 3-benzyloxy-2-[(2-benzyloxy-phenyl)-(tetrahydropyran-2-yloxy)-methyl]-pyran-4-one there is obtained analogously to Example 1c, after chromatography: 3-benzyloxy-2-[(2-benzyloxy-phenyl)-(tetrahydropyran-2-yloxy)-methyl]-1-(2-hydroxy-ethyl)-1H-pyridin-4-one. Beige foam. Diastereoisomeric mixture. $R_f$ values: 0.15 and 0.2 (silica gel 60, ethyl acetate/ethanol 9/1).

e) 3-Benzyloxy-2-[(2-benzyloxy-phenyl)-hydroxy-methyl]-1-(2-hydroxy-ethyl)-.1H-pyridin-4-one: From 2.42 g of 3-benzyloxy-2-[(2-benzyloxy-phenyl)-(tetrahydropyran-2-yloxy)-methyl]-1-(2.-hydroxy-ethyl)-1H-pyridin-4-one there is obtained analogously to Example 6e, after chromatography: 3-benzyloxy-2-[(2-benzyloxy-phenyl)-hydroxy-methyl]-1-(2-hydroxy-ethyl)-1H-pyridin-4-one. Beige foam. $R_f$ value: 0.17 (silica gel 60, ethyl acetate/ethanol 9/1).

EXAMPLE 27

3-Hydroxy-2-(hydroxy-pyridin-2-yl-methyl)-1-methyl-1H-pyridin-4-one

From 1.88 g of 3-benzyloxy-2-(hydroxy-pyridin-2-yl-methyl)-1-methyl-1H-pyridin-4-one there is obtained analogously to Example 7: 3-hydroxy-2-(hydroxy-pyridin-2-yl-methyl)-1-methyl-1H-pyridin-4-one. Colourless crystals, m.p.: 202°–204° C.

The starting material can be prepared, for example, as follows:

a) 2-(Hydroxy-pyridin-2-yl-methyl)-3-hydroxy-pyran-4-one: From 5.05 g of pyromeconic acid and 4.82 g of pyridine-2-carbaldehyde [CAS No.: 1121-60-4] there is obtained analogously to Example 6a: 2-(hydroxy-pyridin-2-yl-methyl)-3-hydroxy-pyran-4-one. Yellow crystals, m.p.: 161.2°–164° C.

b) 3-Benzyloxy-2-(hydroxy-pyridin-2-yl-methyl)-pyran-4-one: From 2-(hydroxy-pyridin-2-yl-methyl)-3-hydroxy-pyran-4-one there is obtained analogously to Example 6b: 3-benzyloxy- 2-(hydroxy-pyridin-2-yl-methyl)-pyran-4-one. Orange oil. $R_f$ value: 0.56 (silica get 60, ethyl acetate/ethanol 9/1).

c) 3-Benzuloxy-2-[pyridin-2-yl-tetrahydropyran-2-yloxy)-methyl]-pyran-4-one: From 12 g of 3-benzyloxy-2-(hydroxy-pyridin-2-yl-methyl)-pyran-4-one there is obtained analogously to Example 6c: 3-benzyloxy-2-[pyridin-2-yl-(tetrahydropyran-2-yloxy)-methyl]-pyran-4-one in the form of a diastereoisomeric mixture. Beige crystals, m.p.: 107°–121 ° C.

d) 3-Benzyloxy-1-methyl-2-[pyridin-2-yl(tetrahydropyran-2-yloxy)-methyl]-1H-pyridin-4-one From 4.5 g of 3-benzyloxy-2-[pyridin-2-yl-(tetrahydropyran-2-yloxy)-methyl]-pyran-4-one there is obtained analogously to Example 7a: 3-benzyloxy-1-methyl-2-[pyridin-2-yl-(tetrahydropyran-2-yloxy)-methyl]-1H-pyridin-4-one. Red resin. Diastereoisomeric mixture. $R_f$ value: 0.05 (silica gel 60, ethyl acetate/ethanol 9/1).

e) 3-Benzyloxy-2-(hydrox-pyridin-2-yl-methyl-1-methyl-1H-pyridin-4-one: From 2.5 g of 3-benzyloxy-1-methyl-2-[pyridin-2-yl-(tetrahydropyran-2-yloxy)-methyl]-1H-pyridin-4-one there is obtained analogously to Example 7b: 3-benzyloxy-2-(hydroxy-pyridin-2-yl-methyl)-1-methyl-1H-pyridin-4-one. Yellow resin. $R_f$ value: 0.52 (silica gel 60, dichloromethane/ethanol 4/1).

Example 28

3-Hydroxy-1-2-hydroxy-ethyl-2-hydroxy-pyridin-2-yl-methyl)-1H-pyridin-4-one

From 0.877 g of 3-benzyloxy-1-(2-hydroxy-ethyl)-2-(hydroxy-pyridin-2-yl-methyl)-1H-pyridin-4-one there is obtained analogously to Example 6:3-hydroxy-1-(2-hydroxy-ethyl)-2-(hydroxy-pyridin-2-yl-methyl)-1H-pyridin-4-one. Colourless crystals, m.p.: decomposition from 185° C.

The starting material can be prepared, for example, as follows:

a) 3 Benzyloxy-1-2 hydroxy-ethyl)-2-[pyridin 2yl-(tetrahydropyran-2-ylox)-methl]-1H-pyridin-4-one: From 4.4 g of 3-benzyloxy-2-[pyridin-2-yl-(tetrahydropyran-2-yloxy)-methyl]-pyran-4-one (Example 27c) there is obtained analogously to Example 6d: 3-benzyloxy-1-(2-hydroxy-ethyl)-2-[pyridin-2-yl-(tetrahydropyran-2-yloxy)-methyl]-1H-pyridin-4-one. Yellow foam. Diastereoisomeric mixture. $R_f$ value: 0.43 (silica gel 60, dichloromethane/ethanol 6/1).

b) 3-Benzyloxy-1-(2-hydroxy-ethyl)-2-(hydroxy-pyridin-2-yl-methyl)-1H-pyridin-4-one: From 1.4 g of 3-benzyloxy-1-(2-hydroxyethyo)-2.[pyridin-2-yl-(tetrahydropyran-2-yloxy)-methyl]-1H-pyridin-4-one there is obtained analogously to Example 6e: 3-benzyloxy-1-(2-hydroxy-ethyl)-2-(hydroxy-pyridin-2-yl-methyl)-1H-pyridin-4-one. Beige crystals. M.p.: 173°–176° C.

EXAMPLE 29

2-(Benzo[1,3]dioxol-5-yl-hydroxy-methyl)-3-hydroxy-1-methyl-1H-pyridin-4-one Hydrogenation of 1.19 g of 2-(benzo[1,3]dioxol-5-yl-hydroxy-methyl)-3-benzyloxy-1-methyl-1H-pyridin-4-one analogously to Example 1 yields 2-(benzo[1,3]dioxol-5-yl-hydroxy-methyl)-3-hydroxy-1-methyl-1H-pyridin-4-one. Light-beige crystals, m.p.: 230°–232° C.

The starting material can be prepared, for example, as follows:

a) 2-(Benzol1,3]dioxol-5-yl-hydroxy-methyl)-3-hydroxy-pyran-4-one: From 5.04 g of pyromeconic acid and 7.11 g of piperonal [CAS-No.: 120-57-0] there is obtained analogously to Example 3a: 2-(benzol1,3]dioxol-5-yl-hydroxy-methyl)-3-hydroxy-pyran-4-one. Beige crystals. M.p.: 158°–160° C.

b) 2-(Benzol1,3]dioxol-5-yl-hydroxy-methyl)-3-benzyloxy-pyran-4-one: From 6.74 g of 2-(benzo[1,3]dioxol-5-yl-hydroxy-methyl)-3-hydroxy-pyran-4-one there is obtained analogously to Example 1a, after chromatography: 2-(benzo[1,3]dioxol-5-yl-hydroxy-methyl)-3-benzyloxy-pyran-4-one. Yellow resin. $R_f$ value: 0.19 (silica gel 60, hexane/ethyl acetate 1/1).

c) .2-[Benzol[1,3]dioxol-5-yl-(tetrahydropyran-2-yloxy)-methyl]-3-benzyloxy-pyran-4-one: From 7.1 g of 2-(benzo[1,3]dioxol-5-yl-hydroxy-methyl)-3-benzyloxy-pyran-4-one there is obtained analogously to Example 1b, after chromatography: 2-[benzo[1,3]dioxol-5-yl-(tetrahydropyran-2-yloxy)-methyl]-3-benzyloxy-pyran-4-one. Light-yellow oil. $R_f$ value: 0.47 (silica gel 60, hexane/ethyl acetate 1/1).

d) 2-[Benzo[1,3]dioxol-5-yl-(tetrahydropyran-2-yloxy)-methyl]-3-benzyloxy-1-methyl-1H-pyridin-4-one: From 2.4 g of 2-[benzo[1,3]dioxol-5-yl-(tetrahydropyran-2-yloxy)-methyl]-3-benzyloxy-pyran-4-one there is obtained analogously to Example 7a: 2-[benzol1,3]dioxol-5-yl-(tetrahydropyran-2-yloxy)-methyl]-3-benzyloxy-1-methyl-1H-pyridin-4-one. Yellow crystals. Diastereoisomeric mixture. M.p.: 148.6°–153° C.

e) 2-(Benzo[1,3]dioxol-5-yl-hydroxy-methyl)-3-benzyloxy-1-methyl-1H-pyridin-4-one: From 1.6 g of 2-[benzo[1,3]dioxol-5-yl-(tetrahydropyran-2-yloxy)-methyl]-3-benzyloxy-1-methyl-1H-pyridin-4-one there is obtained analogously to Example 7b: 2-(benzol1,3]dioxol-5-yl-hydroxy-methyl)-3-benzyloxy-1-methyl-1H-pyridin-4-one. Light-beige crystals, m.p.: 207.5–209.3° C.

EXAMPLE 30

2-(Benzo[1,3]dioxol-5-yl-hydroxy-methyl)-3-hydroxy-1-(2-hydroxy-ethyl)-1H-pyridin-4-one Hydrogenation of 1.5 g of 2-(benzo[1,3]dioxol-5-yl-hydroxy-methyl)-3-benzyloxy-1-(2-hydroxy-ethyl)-1H-pyridin-4-one analogously to Example 1 yields 2-(benzo[1,3]dioxol-5-yl-hydroxy-methyl)-3-hydroxy-1-(2-hydroxy-ethyl)-1H-pyridin-4-one. Beige crystals, m.p.: 195°–196° C.

The starting material can be prepared, for example, as follows:

a) 2-[Benzol,3-]dioxol-5-yl-(tetrahydropyran-2-yloxy)-methyl]-3-benzyloxy-1-(2-hydroxy-ethyl)-1H-pyridin-4-one: From 2.4 g of 2-[benzo[1,3]dioxol-5-yl-(tetrahydropyran-2-yloxy)-methyl]-3-benzyloxy-pyran-4-one (Example 29c) there is obtained analogously to Example 1c: 2-[benzo[1,3]dioxol-5-yl-(tetrahydropyran-2-yloxy)-methyl]-3-benzyloxy-1-(2hydroxy-ethyl)-1H-pyridin-4-one in the form of a diastereoisomeric mixture. Yellow resin. $R_f$ value: 0.17 (silica gel 60, ethyl acetate/ethanol 9/1).

b) 2-(Benzo-[1,3]dioxol-5-yl-hydroxy-methyl)-3-benzyloxy-1-(2-hydroxy-ethyl)-1H-pyridin-4-one: From 2.28 g of 2-[benzo[1,3]dioxol-5-yl-(tetrahydropyran-2-yloxy)-methyl]-3-benzyloxy-1-(2-hydroxy-ethyl);1H-pyridin-4-one there is obtained analogously to Example 1d: 2-(benzo-[1,3]dioxol-5-yl-hydroxy-methyl)-3-benzyloxy-1-(2-hydroxy-ethyl)-1H-pyridin-4-one. Yellow crystals, m.p.: 85°–87° C.

EXAMPLE 31

3-Hydroxy-1-(2-hydroxy-ethyl)-2-[hydroxy-4-nitro-phenyl)-methyl]-1H-pyridin-4-one hydrochloride 1.9 ml of 37% conc. HCl are poured over 0.19 g of 3-benzyloxy-1-(2-hydroxy-ethyl)-2-[hydroxy-(4-nitro-phenyl)-methyl]-1H-pyridin-4-one. The mixture is heated with stirring at 100° C. for 45 minutes. 20 ml of toluene are added and distillation is carried out at a bath temperature of 50° C. and under a pressure of 60 mbar using a rotary evaporator. The addition of toluene and the distillation are repeated four times. The crystalline residue is recrystallised from ethanol, yielding 3-hydroxy-1-(2-hydroxy-ethyl)-2-[hydroxy-(4-nitro-phenyl)-methyl]-1H-pyridin-4-one hydrochloride. Brown crystals, m.p.: from 204° C. with decomposition.

The starting material can be prepared, for example, as follows:

a) 3-Hydroxy-2-[hydroxy-(4-nitro-phenyl)-methyl]-pyran-4-qne: From 16.8 g of pyromeconic acid and 22.7 g of 4-nitrobenzaldehyde there is obtained analogously to Example 3a: 3-hydroxy-2-[hydroxy-(4-nitro-phenyl)-methyl]-pyran-4-one. Yellow crystals, m.p.: decomposition from 176° C.

b) 3.-Benzyloxy-2-[hydroxy-(4-nitro-phenyl)-methyl]-pyran-4-one: From 3-hydroxy-2-[hydroxy-(4-nitro-phenyl)-methyl]pyran-4-one there is obtained analogously to Example 1a, after recrystallisation from ethyl acetate: 3-benzyloxy-2-[hydroxy-(4-nitro-phenyl)-methyl]-pyran-4-one. Yellow crystals, m.p.: 167°–168.5° C.

c) 3-Benzyloxy-2-[(4-nitro-phenyl)-(tetrahydropyran-2-yloxy)-methyl]-pyran-4-one: From 3-benzyloxy-2-[hydroxy-(4-nitro-phenyl)-methyl]pyran-4-one there is obtained analogously to Example 1b: 3-benzyloxy-2-[(4-nitro-phenyl)-(tetrahydropyran-2-yloxy)-methyl]-pyran-4-one in the form of a diastereoisomeric mixture. Yellow resin. $R_f$ value: 0.48 and 0.55 (silica gel 60, hexane/dichloromethane/ethyl acetate 1/1/1).

d) 3-Benzyloxy-1-(2-hydroxy-ethyl)-2-[(4-nitro-phenyl)-(tetrahydropyran-2-yloxy)-methyl]-1H-pyridin-4-one: From 3-benzyloxy-2-[(4-nitro-phenyl)-(tetrahydropyran-2-yloxy)-methyl]-pyran-4-one there is obtained analogously to Example 1c: 3-benzyloxy-1-(2-hydroxy-ethyl)-2-[(4-nitro-phenyl)-(tetrahydropyran-2-yloxy)-methyl]-1H-pyridin-4-one in the form of a diastereoisomeric mixture. Yellow resin. $R_f$ value: 0.16 (silica gel 60, ethyl acetate/ethanol 9/1).

e) 3-Benzyloxy-1-(2-hydroxy-ethyl)-2-[hydroxy-(4-nitro-phenyl)-methyl]-1H-pyridin-4-one: From 0.51 g of 3-benzyloxy-1-(2-hydroxy-ethyl)-2-[(4-nitro-phenyl)-(tetrahydropyran-2-yl-oxy)-methyl]-1H-pyridin-4-one there is obtained analogously to Example 1d: 3-benzyloxy-1-(2-hydroxy-ethyl)-2-[hydroxy-(4-nitro-phenyl)-methyl]-1H-pyridin-4-one. Yellow resin. $R_f$ value: 0.2 (silica gel 60, ethyl acetate/ethanol 9/1).

EXAMPLE 32

3-Hydroxy-1-(2-hydroxy-ethyl)-2-(hydroxy-p-tolyl-methyl)-1H-pyridin-4-one

Hydrogenation of 1.9 g of 3-benzyloxy-1-(2-hydroxy-ethyl)-2-(hydroxy-p-tolyl-methyl)-1H-pyridin-4-one analogously to Example 1 yields 3-hydroxy-1-(2-hydroxy-ethyl)-2-(hydroxy-p-tolyl-methyl)-1H-pyridin-4-one. Light-yellow crystals, m.p.: 205.5°–207° C.

The starting material can be prepared, for example, as follows:

a) 3-Hydroxy-2-(hydroxy-p-tolyl-methyl)-pyran-4-one: From 11.2 g of pyromeconic acid and 12.0 g of p-toluyl aidehyde [CAS No.: 104-87-0] there is obtained analogously to Example 3a: 3-hydroxy-2-(hydroxy-p-tolyl-methyl)-pyran-4-one. Colourless crystals, m.p.: 1 61.3°–165.3° C.

b) 3-Benzyloxy-2-(hydroxy-p-tolyl-methyl)-pyran-4-one: From 16.1 g of 3-hydroxy-2-(hydroxy-p-tolyl-methyl)-pyran-4-one there is obtained analogously to Example 1a, from ethyl acetate: 3-benzyloxy-2-(hydroxy-p-tolyl-methyl)-pyran-4-one. Colourless crystals, m.p.: 134.4°–135.7° C.

c) .3-Benzyloxy-2-[(tetrahydropyran-2-yloxy)-p-tolyl-methyl]-pyran-4-one: From 3-benzyloxy-2-(hydroxy-p-tolyl-methyl)-pyran-4-one there is obtained analogously to Example 1b: 3-benzyloxy-2-[(tetrahydropyran-2-yloxy)-p-tolyl-methyl]-pyran-4-one in the form of a diastereoisomeric mixture. Yellow oil. $R_f$ value: 0.74 (silica gel 60, dichloromethane/ethyl acetate 1/1).

d) 3-Benzyloxy-1-(2-hydroxy-ethyl)-2-[(tetrahydropyran-2-yloxy)-p-tolyl-methyl]1H-pyridin-4-one: From 4.4 g of 3-benzyloxy-2-[(tetrahydropyran-2-yloxy)-p-tolyl-methyl]-pyran-4-one there is obtained analogously to Example 1c: 3-benzyloxy-1-(2-hydroxy-ethyl)-2-[(tetrahydropyran-2-yloxy)-p-tolyl-methyl]-1H-pyridin-4-one in the form of a diastereoisomeric mixture. Yellow oil. $R_f$ value: 0.22 (silica gel 60, ethyl acetate/ethanol 9/1).

e) 3-Benzyloxy-1-(2-hydroxy-ethyl)-2-(hydroxy-p-tolyl-methyl)-1H-pyridin-4-one: From 4.5 g of 3-benzyloxy-1-(2-hydroxy-ethyl)-2-[(tetrahydropyran-2-yloxy)-p-tolyl-methyl]-1H-pyridin-4-one there is obtained analogously to Example 1d: 3-benzyloxy-1-(2-hydroxy-ethyl)-2-(hydroxy-p-tolyl-methyl)-1H-pyridin-4-one. Colourless crystals, m.p.: 95°–97° C.

EXAMPLE 33

2-[(4-Bromo-phenyl)-hydroxy-methyl]-3-hydroxy-1-(2-hydroxy-ethyl)-1H-pyridin-4-one 1.2 g of 3-benzyloxy-1-(2-hydroxy-ethyl)-2-[hydroxy-(4-bromo-phenyl)-methyl]-1H-pyrdin-4-one are dissolved in 100 ml of methanol. 0.2 ml of 1,2-dichlorobenzene is added and the reaction mixture is hydrogenated over 0.24 g of palladium on carbon at room temperature and under normal pressure until 1 mol of $H_2$ per mol of starting material has been taken up. The catalyst is removed by filtration and the flitrate is concentrated to dryness by evaporation. The residue is recrystallised from ethanol, yielding 2-[(4-bromophenyl)-hydroxy-methyl]-3-hydroxy-1-(2-hydroxyethyl)-1H-pyridin-4-one. Colourless crystals, m.p. 189°–193° C.

The same product can also be prepared as follows:

12 ml of 37% conc. HCl are poured over 1.2 g of 3-benzyloxy-1-(2-hydroxy-ethyl)-2-[hydroxy-(4-bromo-phenyl)-methyl]-1H-pyridin-4-one and the reaction mixture is heated with stirring at 110° C. for 10 minutes. After cooling, 15 g of ice are added. With stirring and cooling in an ice bath, the reaction mixture is neutralised with sodium hydroxide solution to a pH of 6.5. 15 ml of ethyl acetate are added and stirring is carried out at room temperature for 18 hours. The resulting product is filtered off and washed with water and ethyl acetate. Recrystallisation from ethanol yields 2-[(4-bromo-phenyl)-hydroxy-methyl]-3-hydroxy-1-(2-hydroxy-ethyl)-1H-pyridin-4-one.

The starting material can be prepared, for example, as follows:

a) 3-Hydroxy-2-[hydroxy-(4-bromo-phenyl)-methyl]-pyran-4-one: From 5.6 g of pyromeconic acid and 9.53 g of 4-bromobenzaldehyde [CAS No.: 1122-91-4] there is obtained analogously to Example 3a: 3-hydroxy-2-[hydroxy-(4-bromo-phenyl)-methyl]-pyran-4-one. Beige crystals, m.p.: 143°–145° C.

b) 3-Benzyloxy-2-[hydroxy-(4-bromo-phenyl)-methyl]-pyran-4-one: From 14.0 g of 3-hydroxy-2-[hydroxy-(4-bromo-phenyl)-methyl]pyran-4-one there is obtained analogously to Example 1a, after recrystallisation from ethyl acetate: 3-benzyloxy-2-[hydroxy-(4-bromo-phenyl)-methyl]-pyran-4-one. Colourless crystals, m.p.: 148°–149° C.

c) 3-Benzyloxy-2-[(4-bromo-phenyl)-(tetrahydropyran-2-yloxy)-methyl]-pyran-4-one: From 3-benzyloxy-2-[hydroxy-(4-bromo-phenyl)-methyl]pyran-4-one there is obtained analogously to Example 1b: 3-benzyloxy-2-[(4-bromo-phenyl)-(tetrahydropyran-2-yloxy)-methyl]-pyran-4-one in the form of a diastereoisomeric mixture. Yellow resin. $R_f$ value: 0.47 (silica gel 60, hexane/dichloromethane/ethyl acetate 1/1/1).

d) 3-Benzyloxy-1-(2-hydroxy-ethyl)-2-[(4-bromo-phenyl)-(tetrahydropyran-2-yloxy)-methyl]-1H-pyridin-4-one: From 5.25 g of 3-benzyloxy-2-[(4-bromo-phenyl)-(tetrahydropyran-2-yloxy)-methyl]-pyran-4-one there is obtained analogously to Example 1c: 3-benzyloxy-1-(2-hydroxy-ethyl)-2-[(4-bromo-phenyl)-(tetrahydropyran-2-yloxy)-methyl]-1H-pyridin-4-one in the form of a diastereoisomeric mixture. Yellow foam. $R_f$ value: 0.19 (silica gel 60, ethyl acetate/ethanol 9/1).

e) 3-Benzyloxy-1-(2-hydroxy-ethyl)-2-[hydroxy-(4-bromo-phenyl)-methyl]-1H-pyridin-4-one: From 5.2 g of 3-benzyloxy-1-(2-hydroxy-ethyl)-2-[(4-bromo-phenyl)-(tetrahydropyran-2-yloxy)-methyl]-1H-pyridin-4-one there is obtained analogously to Example 1d: 3-benzyloxy-1-(2-hydroxy-ethyl)-2-[hydroxy-(4-bromo-phenyl)-methyl]-1H-pyridin-4-one. Light-beige crystals, m.p.: 97°–102° C.

EXAMPLE 34

2-[(4-Chloro-phenyl)-hydroxy-methyl]-3-hydroxy-1-(2-hydroxy-ethyl)-1H-pyridin-4-one 26 ml of 37% conc. HCl are poured over 2.65 g of 3-benzyloxy-1-(2-hydroxy-ethyl)-2-[hydroxy-(4-chloro-phenyl)-methyl]-1H-pyridin-4-one and the reaction mixture is heated with stirring at 110° C. for 10 minutes. After cooling, 100 g of ice are added. With stirring and cooling in an ice-bath, the reaction mixture is neutralised with approximately 22 ml of conc. sodium hydroxide solution to a pH of 6.5. 50 ml of ethyl acetate are added and stirring is carried out at room temperature for 4 hours. The resulting product is filtered off and washed with water and ethyl acetate, yielding 2-[(4-chloro-phenyl)-hydroxy-methyl]-3-hydroxy-1-(2-hydroxy-ethyl)-1H-pyridin-4-one. M.p.: 184°–186° C.

The starting material can be prepared, for example, as follows:

a) 3-Hydroxy-2-[hydroxy-(4-chloro-phenyl)-methyl]-pyran-4-one: From 5.6 g of pyromeconic acid and 7.1 g of 4-chlorobenzaldehyde [CAS No.: 104-88-1] there is obtained analogously to Example 3a: 3-hydroxy-2-[hydroxy-(4-chloro-phenyl)-methyl]-pyran-4-one. Beige crystals, m.p.: 144°–146° C.

b) 3-Benzyloxy-2-[hydroxy-(4-chloro-phenyl)-methyl]-pyran-4-one: From 11.4 g of 3-hydroxy-2-[hydroxy-(4-chloro-phenyl)-methyl]pyran-4-one there is obtained analogously to Example 1a, after recrystallisation from ethyl acetate: 3-benzyloxy-2-[hydroxy-(4-chloro-phenyl)-methyl]-pyran-4-one. Colourless crystals, m.p.: 142°–143° C.

c) 3-Benzyloxy-2-[(4-chloro-phenyl)-(tetrahydropyran-2-yloxyl)-methyl]-pyran-4-one: From 12.0 g of 3-benzyloxy-2-[hydroxy-(4-chloro-phenyl)-methyl]pyran-4-one there is obtained alogously to Example 1b: 3-benzyloxy-2-[(4-chloro-phenyl)-(tetrahydropyran-2-yloxy)-methyl]-pyran-4-one in the form of a diastereoisomeric mixture. Yellow resin, $R_f$ value: 0.2 (silica gel 60, hexane/dichloromethane/ethyl acetate 1/1/1).

d) 3-Benzyloxy-1-(2-hydroxy-ethyl)-2-[(4-chloro-phenyl)-(tetrahydropyran-2-yloxy)-methyl]-1H-pyridin-4-one: From 5.0 g of 3-benzyloxy-2-[(4-chloro-phenyl)-(tetrahydropyran-2-yloxy)-methyl]-pyran-4-one there is obtained analogously to Example 1c: 5.1 g of 3-benzyloxy-1-(2-hydroxy-ethyl)-2-[(4-chloro-phenyl)-(tetrahydropyran-2-yloxy)-methyl]-1H-pyridin-4-one in the form of a diastereoisomeric mixture. Yellow crystals, m.p.: 157°–167° C. $R_f$ value: 0.25 (silica gel 60, ethyl acetate/ethanol 9/1).

e) 3-Benzyloxy-1-(2-hydroxy-ethyl)-2-[hydroxy-(4-chloro-phenyl)-methyl]-1H-pyridin-4-one: From 5.1 g of 3-benzyloxy-1-(2-hydroxy-ethyl)-2-[(4-chloro-phenyl)-(tetrahydropyran-2-yloxy)-methyl]-1H-pyridin-4-one there is obtained analogously to Example 1d: 3-benzyloxy-1-(2-hydroxy-ethyl)-2-[hydroxy-(4-chloro-phenyl)-methyl]-1H-pyridin-4-one. Beige crystals. M.p.: 87°–92° C.

EXAMPLE 35

1-(4-Chloro-phenyl)-9-hydroxy-3,4-dihydro-1H-pyrido[2,1-c][1,4]oxazin-8-one 2.5 ml of 37% conc. hydrochloric acid are added to 0.245 g of 3-benzyloxy-1-(2-hydroxy-ethyl)-2-[hydroxy-(4-chloro-phenyl)-methyl]-1H-pyridin-4-one (Example 34e) and the solution is heated with stirring at 110° C. for 45 minutes. After cooling, 5 g of ice are added. The reaction mixture is neutralised with sodium hydroxide solution to a pH of 6.5, then 5 ml of ethyl acetate are added and stirring is carried out for 4 hours in an ice-bath. The reaction mixture is filtered and washed with water and ethyl acetate. Drying yields 1-(4-chloro-phenyl)-9-hydroxy-3,4-dihydro-1H-pyrido[2,1-c][1,4]oxazin-8-one. Pink crystals, m.p.: 211°–214° C.

EXAMPLE 36

1-(4-Fluoro-phenyl)-9-hydroxy-3,4-dihydro-1H-pyrido[2,1-c][1,4]oxazi

From 1.1 g of 3-benzyloxy-1-(2-hydroxy-ethyl)-2-[hydroxy-(4-fluoro-phenyl)-methyl]-1H-pyridin-4-one (Example 3e) there is obtained analogously to Example 35: 1-(4-fluoro-phenyl)-9-hydroxy-3,4-dihydro-1H-pyrido[2,1-c][1,4]oxazin-8-one. Orange crystals, m.p.: 221°–223° C.,

EXAMPLE 37

1-(4-Bromo-phenyl)-9-hydroxy-3,4-dihydro-1H-pyrido[2,1-c][1,4]oxazin-8-one

From 1.0 g of 3-benzyloxy-1-(2-hydroxy-ethyl)-2-[hydroxy-(4-bromo-phenyl)-methyl]-1H-pyridin-4-one (Example 33e) there is obtained analogously to Example 35: 1-(4-bromo-phenyl)-9-hydroxy-3,4-dihydro-1H-pyrido[2,1-c][1,4]oxazin-8-one. Orange crystals, m.p.: 200°–212° C.

EXAMPLE 38

6-[(4-Fluoro-phenyl)-hydroxy-methyl]-7-hydroxy-3,4-dihydro-pyrido[2,1-c][1,4]-oxazine-1,8-dione 0.266 g of 5-benzyloxy-6-[(4-fluoro-phenyl)-hydroxy-methyl]-1-(2-hydroxy-ethyl)-4-oxo-1,4-dihydro-pyridine-2-carboxylic acid are dissolved in 20 ml of methanol and hydrogenated at room temperature over 0.05 g of palladium on carbon (5%) until 1 mol of $H_2$ per mol of starting material has been taken up. The catalyst is removed by filtration and the flitrate is concentrated to dryness by evaporation using a rotary evaporator. Recrystallisation from methanol yields 6-[(4-fluoro-phenyl)-hydroxy-methyl]-7-hydroxy-3,4-dihydro-pyrido[2,1-c]-[1,4]oxazine-1,8-dione in the form of colourless crystals. M.p.: 221°–225° C.

The starting material can be prepared, for example, as follows:
a) 6-[(4-Fluoro-phenyl)-hydroxy-methyl]5-hydroxy-4-oxo-4H-pyran-2-carboxylic acid: 7.8 g of 5-hydroxy-4-oxo-4H-pyran-2-carboxylic acid [CAS No.: 499-78-5] are dissolved in 15 of water and 47.5 ml of 2N NaOHo 6.2 g of 4-fluorobenzaldehyde and then 20 ml of methanol are added. Stirring is carried out at room temperature for 48 hours. The methanol is removed using a rotary evaporator and the aqueous solution that remains is neutralised with 47.5 ml of 2N HCl. The resulting crystal suspension is stirred in an ice-bath for one hour and then the product is filtered off and washed with water. Drying yields: 10.9 g of 6-[(4-fluorophenyl)-hydroxy-methyl]-5-hydroxy-4-oxo-4H-pyran-2-carboxylic acid. $R_f$ value: 0.27 (silica gel 60, dichloromethane/methanol/water/glacial acetic acid 75/27/5/0.5).
b) 5-Benzyloxy-6-[(4-fluoro-phenyl)-hydroxy-methyl]-4-oxo-4H-pyran-2-carboxylic acid benzyl ester: From 6-[(4-fluoro-phenyl)-hydroxy-methyl]-5-hydroxy-4-oxo-4H-pyran-2-carboxylic acid there is obtained analogously to Example 15b, after chromatography: 5-benzyloxy-6-[(4-fluoro-phenyl)-hydroxy-methyl]-4-oxo-4H-pyran-2-carboxylic acid benzyl ester. $R_f$ value: 0.2 (silica gel 60, hexane/ethyl acetate 2/1).
c) 5-Benzyloxy-6-[(4-fluoro-phenyl)-(tetrahydropyran-2-yloxy)-methyl]-4-oxo-4H-pyran-2-carboxylic acid benzyl ester: From 5-benzyloxy-6-[(4-fluoro-phenyl)-hydroxy-methyl]-4-oxo-4H-pyran-2-carboxylic acid benzyl ester there is obtained analogously to Example 6c: 5-benzyloxy-6-[(4-fluoro-phenyl)-(tetrahydropyran-2-yloxy)-methyl]-4-oxo-4H-pyran-2-carboxylic acid benzyl ester. Yellow oil. $R_f$ value: 0.33 (silica gel 60, hexane/ethyl acetate 4/1).
d) 5-Benzyloxy-6-[(4-fluoro-phenyl)-(tetrahydropyran-2-yloxy)-methyl]-1-(2-hydroxy-ethyl-4-oxo-1,4-dihydro-pyridine-2-carboxylic acid(2-hydroxy-ethyl)-amide: 7.2 g of 5-benzyloxy-6-[(4-fluoro-phenyl)-(tetrahydropyran-2-yloxy)-methyl]-4-oxo-4H-pyran-2-carboxylic acid benzyl ester are boiled under reflux for 48 hours in 70 ml of ethanol and 7 ml of ethanolamine. The solvent is removed using a rotary evaporator. The residue is taken up in 100 ml of ethyl acetate and washed three times with 30 ml of water each time. The organic phase is dried over magnesium sulfate and filtered and concentrated to dryness by evaporation using a rotary evaporator. Chromatography on silica gel yields 5-benzyloxy-6-[(4-fluoro-phenyl)-(tetrahydropyran-2-yloxy)-methyl]-1-(2-hydroxy-ethyl-4-oxo-1,4-dihydro-pyridine-2-carboxylic acid (2-hydroxy-ethyl)-amide. $R_f$ value: 0.1 (silica gel 60, dichloromethane/ethanol 4/1).
e) 5-Benzyloxy-6-[(4-fluoro-phenyl)-hydroxy-methyl]-1-(2-hydroxy-ethyl)-4-oxo-1,4-dihydro-pyridine-2-carboxylic acid: 1 g of 5-benzyloxy-6-[(4-fluoro-phenyl)-(tetrahydropyran-2-yloxy)-methyl]-1-(2-hydroxy-ethyl)-4-oxo-1,4-dihydro-pyridine-2-carboxylic acid (2-hydroxy-ethyl)-amide is dissolved in a mixture of 5 ml of 2N HCl and 5 ml of ethanol and boiled under reflux for 3 hours. After cooling to room temperature, 7.5 ml of 2N NaOH are added. The ethanol is removed using a rotary evaporator and the aqueous solution that remains is adjusted to pH 4 with 2N HCl. The crystals that precipitate are filtered off and dried, yielding 5-benzyloxy-6-[(4-fluoro-phenyl)-hydroxy-methyl]-1-(2-hydroxy-ethyl)-4-oxo-1,4-dihydro-pyridine-2-carboxylic acid. Beige crystals. $R_f$ value: 0.26 (silica gel 60, dichloromethane/methanol/water/glacial acetic acid 75/27/5/0.5).

EXAMPLE 39

9-Hydroxy-1-phenyl-3,4-dihydro-1H-pyrido[2,1-c][1,4]oxazin-8-one

From 1.49 g of an approximately equimolar mixture of 3-benzyloxy-1-(2-hydroxy-ethyl)-2-(hydroxy-phenyl-methyl)-1H-pyridin-4-one (Example 1d) and 3-hydroxy-1-(2-hydroxy-ethyl)-2-(hydroxy-phenyl-methyl)-1H-pyridin-4-one (Example 1) there is obtained analogously to Example 35: 9-hydroxy-1-phenyl-3,4-dihydro-1H-pyrido[2,1-c][1,4]oxazin-8-one. Beige crystals, m.p.: 229°–234° C.

EXAMPLE 40

9-Hydroxy-1-p-tolyl-3,4-dihydro-1H-pyrido[2,1-c][1,4]oxazin-8-one

From 0.46 g of 3-benzyloxy-1-(2-hydroxy-ethyl)-2-(hydroxy-p-tolyl-methyl)-1H-pyridin-4-one (Example 32e) there is obtained analogously to Example 35: 9-hydroxy-1-p-tolyl-3,4-dihydro-1H-pyrido[2,1-c][1,4]oxazin-8-one. Reddish crystals, m.p.: 210°–218° C. with decomposition. Crystal transformation from rods to needles from 200° C.

EXAMPLE 41

4-[2-(4-Fluorobenzyl)-3-hydroxy-4-oxo-4H-pyridin-1-yl]-butyric acid ethyl 2.1 g of 4-{2-[acetoxy-(4-fluoro-phenyl)-methyl]-3-benzyloxy-4-oxo-4H-pyridin-1-yl}-butyric acid ethyl ester are hydrogenated in 50 ml of tetrahydrofuran over 0.5 g of palladium on carbon (5%) under normal pressure and at a temperature of 50° C. until 2 mol of $H_2$ per mol of starting material have been taken up. The catalyst is removed by filtration and the flitrate is concentrated by evaporation using a rotary evaporator. Recrystallisation from ethyl acetate yields: 4-[2-(4-fluorobenzyl)-3-hydroxy-4-oxo-4H-pyridin-1-yl]-butyric acid ethyl ester. Slightly reddish crystals. M.p.: 137°–141° C.

The starting material can be prepared, for example, as follows:

a) 4-{3-Benzyloxy-2-[(4-fluoro-phenyl)-hydroxy-methyl]-4-oxo-4H-pyridin-1-yl}-butyric acid ethyl ester: 2.15 g of 4-{3-benzyloxy-2-[(4-fluoro-phenyl)-hydroxy-methyl]-4-oxo-4H-pyridin-1-yl}-butyric acid (Example 17b) are dissolved in 100 ml of absolute ethanol. 2 ml of hydrogen chloride in ether (5N) are added and the solution is boiled under reflux for 5 hours and then concentrated by evaporation using a rotary evaporator. Approximately 50 ml of toluene are added to the residue. After concentration to dryness by evaporation again, 20 ml of ethyl acetate are added to the residue. The crystals thai have precipitated are filtered off, washed with ethyl acetate and dried, yielding 4-{3-benzyloxy-2-[(4-fluoro-phenyl)-hydroxy-methyl]-4-oxo-4H-pyridin-1-yl}-butyric acid ethyl ester in the form of the hydrochloride. Colourless crystals, m.p.: 136°–138° C.

b) 4-{2-[Acetoxy-(4-fluoro-phenyl)-methyl]-3-benzyloxy-4-oxo-4H-pyridin-1-yl}-butyric acid ethyl ester: From 4-{3-benzyloxy-2-[(4-fluoro-phenyl)-hydroxy-methyl]-4-oxo-4H-pyridin-1-yl}-butyric acid ethyl ester there is obtained analogously to Example 9a: 4-{2-[acetoxy-(4-fluoro-phenyl)-methyl]-3-benzyloxy-4-oxo-4H-pyridin-1-yl}-butyric acid ethyl ester. Slightly opaque resin. $R_f$ value: 0.12 (silica gel 60, dichloromethane/ethyl acetate 1/1).

EXAMPLE 42

2-Benzyl-3-hydroxy-1-(2-acetoxy-ethyl)-1H-pyridin-4-one 2.2 g of acetic acid [1-(2-acetoxy-ethyl)-3-benzyloxy-4-oxo-1,4-dihydropyridin-2-yl-methyl]-phenyl-methyl ester are hydrogenareal in 50 ml of tetrahydrofuran over 0.5 g of palladium on carbon (5%) under normal pressure and at a temperature of 50° C. until 2 mol of $H_2$ per mol of starting material have been taken up. The catalyst is removed by filtration and the flitrate is concentrated by evaporation using a rotary evaporator. Recrystallisation from tetrahydrofuran yields 2-benzyl-3-hydroxy-1-(2-acetoxy-ethyl)-1H-pyridin-4-one, Colourless crystals, m.p.: 139.7°–140.7° C.

The starting material can be prepared, for example, as follows:

a) Acetic acid [1-(2-acetoxy-ethyl)-3-benzyloxy-4-oxo-1,4-dihydropyridin-2-yl-methyl]-phenyl-methyl ester: 1.76 g of 3obenzyloxy-1-(2-hydroxy-ethyl)-2-(hydroxy-phenylomethyl)-1H-pyridin-4-one (Example 1d) are suspended in 20 ml of dichloromethane, and 1.5 ml of triethylamine are added. 1.04 ml of acetic anhydride and then 20 mg of 4-dimethylamino-pyridine are added, Stirring is carried out at room temperature. After 5 hours, the reaction solution is diluted with 100 ml of ethyl acetate and washed four times with 20 ml of water each time and once with 10 ml of saturated brine. The organic phase is dried over magnesium sulfate, filtered and concentrated by evaporation, yielding acetic acid [1-(2-acetoxy-ethyl)-3-benzyloxy-4-oxo-1,4-dihydropyridin-2-yl-methyl]-phenyl-methyl ester in the form of a crude product. Opaque resin. $R_f$ value: 0.5 (silica gel 60, ethyl acetate/ethanol 9/1).

EXAMPLE 43

Acetic acid [1-(2-acetoxy-ethyl)-3-hydroxy-4-oxo-1,4-dihydropyridin-2-yl-methyl]-phenyl-methyl ester 1.62 g of acetic acid [1-(2-acetoxy-ethyl)-3-benzyloxy-4-oxo-1,4-dihydropyridin-2-yl-methyl]-phenyl-methyl ester are hydrogenated in 100 ml of tetrahydrofuran over 200 mg of palladium on carbon (5%) under normal pressure and at room temperature until 1 mol of $H_2$ per mol of starting material has been taken up. The catalyst is removed by filtration and the filtrate is concentrated by evaporation using a rotary evaporator, yielding: acetic acid [1-(2-acetoxy-ethyl)-3-hydroxy-4-oxo-1,4-dihydropyridin-2-yl-methyl]-phenyl-methyl ester. Colourless crystals, m.p.: 154°–156° C.

The starting material can be prepared, for example, as follows:

a) Acetic acid [1-(2-acetoxy-ethyl)-3-benzyloxy-4-oxo-1,4-dihydropyridin-2-yl-methyl]-phenyl-methyl ester: 17.4 g of 3-benzyloxy-1-(2-hydroxy-ethyl)-2-(hydroxy-phenyl-methyl)-1H-pyrdin-4-one (Example 1d) are suspended at room temperature in 200 methane. 33 mmethane. 33 ml of triethylamine and 18.7 ml of acetic anhydride are added. After the addition of 0.05 g of 4-dimethylaminopyridine [CAS No.: 1122-58-3], the reaction mixture is stirred at room temperature for 23 hours. 5 ml of ethanol are added and stirring is carried out at room temperature for 30 minutes. For working-up, the reaction mixture is washed three times with 50 ml of water each time. The organic phase is dried over magnesium sulfate and filtered. The flitrate is concentrated by evaporation using a rotary evaporator, yielding acetic acid [1-(2-acetoxy-ethyl)-3-benzyloxy-4-oxo-1,4-dihydropyridin-2-yl-methyl]-phenyl-methyl ester. Orange resin. $R_f$ value 0.125 (silica gel 60, dichloromethane/ethyl acetate 1/1).

The compounds listed below can also be prepared analogously to Examples 1 to 43:

EXAMPLE 44

4-{2-[(4-Fluoro-phenyl)-hydroxy-methyl]-3-hydroxy-4-oxo-4H-pyridin-1-yl}-butyric acid ethyl ester

EXAMPLE 45

4-[3-Hydroxy-2-(hydroxy-phenyl-methyl)-4-oxo-4H-pyridin-1-yl]-butyric acid ethyl ester

EXAMPLE 46

4-(2-Benzyl-3-hydroxy-4-oxo-4H-pyridin-1-yl)-butyric acid ethyl ester

EXAMPLE 47

3,9-Dihydroxy-1-pheny-1-3,4-dihydro-1H-pyrido[2,1-c][1,4]oxazino8-one

EXAMPLE 48

1-(4-Fluorophenyl)-3,9-dihydroxy-3,4-dihydro-1H-pyrido[2,1-c[]1,4]oxazin-8-one

EXAMPLE 49

2-[(2-Fluorophenyl)-hydroxy-methyl]-3-hydroxy-1-(2-hydroxy-ethyl)-1H-pyridin-4-one Hydrogenation of 1.5 g of 2-[(2-fluorophenyl)-hydroxy-methyl]-3-benzyloxy-1-(2-hydroxy-ethyl)-1H-pyridin-4-one analogously to Example 1and recrystallisation from ethanol yield 2-[(2-fluorophenyl)-hydroxy-methyl]-3-hydroxy-1-(2-hydroxy-ethyl)-1H-pyridin-4-one in the form of colourless crystals. M.p.: 177°–178° C.

The starting material can be prepared, for example, as follows:

a) 2-[(2-Fluorophenyl)-hydroxy-methyl]-3-hydroxy-pyran-4-one: From 5.6 g of pyromeconic acid and 6.33 g of 2-fluorobenzaldehyde [CAS No.: 446-52-6] there is obtained analogously to Example 3a: 2-[(2-fluorophenyl)-hydroxy-methyl]-3-hydroxy-pyran-4-one in the form of colourless crystals. M.p.: 122.5°–124° C.

b) 2-[(2-Fluorophenyl)-hydroxy-methyl]-3-benzyloxy-pyran-4-one: Reaction of 10.9 g of 2-[(2-fluorophenyl)-hydroxy-methyl]-3-hydroxy-pyran-4-one with benzyl bromide in N,N-dimethylformamide and potassium carbonate analogously to Example 1a yields 2-[(2-fluorophenyl)-hydroxy-methyl]-3-benzyloxy-pyran-4-one. Colourless crystals, m.p.: 116°–116.5° C.

c) 3-Benzyloxy-2-[(2-fluorophenyl)-(tetrahydro-pyran-2-yloxy)-methyl]-pyran-4-one: Reaction of 13.2 g of 2-[(2-fluorophenyl)-hydroxy-methyl]-3-benzyloxy-pyran-4-one with 3,4-dihydro-H-pyran analogously to Example 1b yields crude 3-benzyloxy-2-[(2-fluorophenyl)-(tetrahydro-pyran-2-yloxy)-methyl]-pyran-4-one in the form of a diastereoisomeric mixture. $R_f$ value 0.55 (silica gel 60, hexane/dichloromethane/ethyl acetate 1/1/1).

d) 3-Benzyoxy-1-(2-hydroxy-ethyl)-2-[-2-fluorophenyl)-(tetrahydro-pyran-2-yloxo)-methyl]-1H-pyridin-4oone: 5.66 g of 3-benzyloxy-2-[(2-fluorophenyl)-(tetrahydro-pyran-2-yloxy)-methyl]-pyran-4-one are boiled under reflux for 24 hours in 50 ml of ethanol and 10 ml of ethanolamine. Working-up analogously to Example 1c yields 3-benzyloxy-1-(2-hydroxy-ethyl)-2-[(2-fluorophenyl)-(tetrahydro-pyran-2-yloxy)-methyl]-1H-pyridin-4-one in the form of a semi-crystalline yellow mass. $R_f$ value: 0.2 (silica gel 60, ethyl acetate/ethanol 9/1).

e) 2-[(2-Fluorophenyl)-hydroxy-methyl]-3-benzyloxy-1-(2-hydroxy-ethyl)-1H-pyridin-4-one: 6.3 g of 3-benzyloxy-1-(2-hydroxy-ethyl)-2-[(2-fluorophenyl)-(tetrahydro-pyran-2-yloxy)-methyl]-1H-pyridin-4-one are boiled under reflux for 3 hours in 65 ml of ethanol and 13 ml of 2N hydrochloric acid. For working-up, the ethanol is removed using a rotary evaporator. The residue is diluted with 50 ml of water and covered with 50 ml of ethyl acetate. With stirring, 50 ml of saturated sodium hydrogen carbonate solution are added. The resulting product is filtered off and washed with water and ethyl acetate. Drying yields 2-[(2-fluorophenyl)-hydroxy-methyl]-3-benzyloxy-1-(2-hydroxy-ethyl)-1H-pyridin-4-one in the form of colourless crystals. M.p.: 164°–166° C.

EXAMPLE 50

2-[(3-Fluorophenyl)-hydroxy-methyl]-3-hydroxy-1-(2-hydroxy-ethyl)-1H-pyridin-4-one Hydrogenation of 1.2 g of 2-[(3-fluorophenyl)-hydroxy-methyl]-3-benzyloxy-1-(2-hydroxy-ethyl)-1H-pyridin-4-one analogously to Example 1 yields 2-[(3-fluorophenyl)-hydroxy-methyl]-3-hydroxy-1-(2-hydroxy-ethyl)-1H-pyridin-4-one in the form of colourless crystals. M.p.: 194.2°–196.2° C.

The starting material can be prepared, for example, as follows:

a) 2-[(3-fluorophenyl)-hydroxy-methyl]-3-hydroxy-pyran-4-one: From 5.6 g of pyromeconic acid and 6.33 g of 3-fluorobenzaldehyde [CAS No.: 456-48-4] there is obtained analogously to Example 3a: 2-[(3-fluorophenyl)-hydroxy-methyl]-3-hydroxy-pyran-4-one in the form of colourless crystals. M.p.: 149°–150.5° C.

b) 2-[(3-Fluorophenyl)-hydroxy-methyl]-3-benzyloxy-pyran-4-one: Reaction of 11.2 g of 2-[(3-fluorophenyl)-hydroxy-methyl]-3-hydroxy-pyran-4-one with benzyl bromide in N,N-dimethylformamide and potassium carbonate analogously to Example 1a yields 2-[(3-fluorophenyl)-hydroxy-methyl]-3-benzyloxy-pyran-4-one. Colourless crystals, m.p.: 95°–96° C.

c) 3-Benzyloxy-2-[(3-fluorophenyl)-(tetrahydro-pyran-2-yloxy)-methyl]-pyran-4-one: Reaction of 11.3 g of 2-[(3-fluorophenyl)-hydroxy-methyl]-3-benzyloxy-pyran-4-one with 3,4-dihydro-2H-pyran analogously to Example 1b yields crude 3-benzyloxy-2-[(3-fluorophenyl)-(tetrahydro-pyran-2-yloxy)-methyl]-pyran-4-one in the form of a diastereoisomeric mixture. $R_f$ value 0.5 (silica gel 60, hexane/dichloromethane/ethyl acetate 1/1/1).

d) 3-Benzyloxy-1-(2-hydroxy-ethyl)-2-[(3-fluorophenyl)-(tetrahydro-pyran-2-yloxy)-methyl]-1H-pyridin-4-one: 5.0 g of 3-benzyloxy-2-[(3-fluorophenyl)-(tetrahydro-pyran-2-yloxy)-methyl]-pyran-4-one are boiled under reflux for 24 hours in 50 ml of ethanol and 10 ml of ethanolamine. Working-up analogously to Example 1c yields 3-benzyloxy-1-(2-hydroxy-ethyl)-2-[(3-fluorophenyl)-(tetrahydro-pyran-2-yloxy)-methyl]-1H-pyridin-4-one in the form of a yellow resin. $R_f$ value: 0.22 (silica gel 60, ethyl acetate/ethanol 9/1).

e) 2-[(3-Fluorophenyl)-hydroxy-methyl]-3-benzyloxy-1-(2-hydroxy-ethyl)-1H-pyridin-4-one: From 5.3 g of 3-benzyloxy-1-(2-hydroxy-ethyl)-2-[(3-fluorophenyl)-(tetrahydro-pyran-2-yl-oxy)-methyl]-1H-pyridin-4-one there is obtained analogously to Example 49e: 2-[(3-fluoro-phenyl)-hydroxy-methyl]-3-benzyloxy-1-(2-hydroxy-ethyl)-1H-pyridin-4-one in the form of colourless crystals. M.p.: 179°–182° C. Crystal transformation from 80° C.

EXAMPLE 51

5-Hydroxy-1-(2-hydroxy-ethyl)-6-(hydroxy-phenyl-methyl)-4-oxo-1,4-dihydro-pyridine-2-carboxylic acid

EXAMPLE 52

5-Hydroxy-1-(2-hydroxy-ethyl)-6-(hydroxy-phenyl-methyl)-4-oxo-1,4-dihydro-pyridine-2-carboxylic acid (2-hydroxyethyl)-amide

EXAMPLE 53

2-[(4-Fluoro-phenyl)-hydroxy-methyl]-3-hydroxy-1-(2-hydroxy-ethyl)-6-hydroxy-methyl-1H-pyridin-4-one

EXAMPLE 54

Acetic acid 1-(2-acetoxy-ethyl)-6-[acetoxy-(4-fluoro-phenyl)-methyl]-5-hydroxy-4-oxo-1,4-dihydro-pyridin-2-yl methyl ester

EXAMPLE 55

3-Hydroxy-1-(2-hydroxy-ethyl)-2-(hydroxy-naphth-2-yl-methyl)-1H-pyridin-4-one

Hydrogenation of 1.5 g of 2-(hydroxy-naphth-2-yl-methyl)-3-benzyloxy-1-(2-hydroxy-ethyl)-1H-pyridin-4-one analogously to Example 1 yields: 3-hydroxy-1-(2-hydroxy-ethyl)-2-(hydroxy-naphth-2-yl-methyl)-1H-pyridin-4-one in the form of orange crystals. M.p.: slow decomposition from 207° C.

The starting material can be prepared, for example, as follows:

a) 2-(Hydroxy-naphth-2-yl-methyl)-3-hydroxy-pyran-4-one: From 5.6 g of pyromeconic acid and 8.05 g of 2-naphthaldehyde [CAS No.: 66-99-9] there is obtained analogously to Example 3a: 2-(hydroxy-naphth-2-yl-methyl)-3-hydroxy-pyran-4-one in the form of colourless crystals. M.p.:140°–144° C.

b) 2-(Hydroxy-naphth-2-yl-methyl)-3-benzyloxy-pyran-4-one: Reaction of 12.9 g of 2-(hydroxy-naphth-2-yl-methyl)-3-hydroxy-pyran-4-one with benzyl bromide in N,N-dimethylformamide and potassium carbonate analogously to Example 1a yields 2-(hydroxy-naphth-2-yl-methyl)-3-benzyloxy-pyran-4-one. Beige crystals, m.p.: 159°–160° C.

c) 3-Benzyloxy-2-[naphth-2-yl-(tetrahydro-pyran-2-yloxy)-methyl]-pyran-4-one: Reaction of 12.9 g of 2-(hydroxy-naphth-2-yl-methyl)-3-benzyloxy-pyran-4-one with 3,4-dihydro-2H-pyran analogously to Example 1b yields crude 3-benzyloxy-2-[naphth-2-yl-(tetrahydro-pyran-2-yloxy)-methyl]-pyran-4-one in the form of a diastereoisomeric mixture, $R_f$ value: 0.52 (silica gel 60, hexane/dichloromethane/ethyl acetate 1/1/1).

d) 3-Benzyloxy-1-(2-hydroxy-ethyl)-2-[naphth-2-yl-(tetrahydro-pyran-2-yloxy)-methyl]-1H-pyridin-4-one: 5.7 g of 3-benzyloxy-2-[naphth-2-yl-(tetrahydro-pyran-2-yloxy)-methyl]-pyran-4-one are boiled under reflux for 24 hours in 60 ml of ethanol and 6 ml of ethanolamine. Working-up analogously to Example 1c yields crude 3-benzyloxy-1-(2-hydroxy-ethyl)-2-[naphth-2-yl-(tetrahydro-pyran-2-yloxy)-methyl]-1H-pyridin-4-one in the form of a hard yellow foam. $R_f$ value: 0.25 (silica gel 60, ethyl acetate/ethanol 9/1).

e) 2-[Naphth-2-yl-hydroxy-methyl]-3-benzyloxy-1-(2-hydroxy-ethyl)-1H-pyridin-4-one: 5.9 g of 3-benzyloxy-1-(2-hydroxy-ethyl)-2-[naphth-2-yl-(tetrahydro-pyran-2-yloxy)-methyl]-1H-pyridin-4-one are boiled under reflux for 3 hours in a mixture of 60 ml of ethanol and 12 ml of 2N hydrochloric acid. The ethanol is removed using a rotary evaporator and the aqueous solution that remains is neutralised with excess aqueous sodium hydrogen carbonate solution. The resulting product is extracted twice with 50 ml of ethyl acetate each time. The organic phases are washed twice with 20 ml of water each time and once with 20 ml of brine. The organic phases are combined, dried over magnesium sulfate and filtered and the flitrate is concentrated to dryness by evaporation using a rotary evaporator. Recrystallisation from ethyl acetate yields 2-[naphth-2-yl-hydroxy-methyl]-3-benzyloxy-1-(2-hydroxy-ethyl)-1H-pyridin-4-one with, per mol, ⅓ mol of ethyl acetate as crystal solvent. Colourless crystals. M.p.: 110.5°–111.5° C.

EXAMPLE 56

4-[3-Hydroxy-2-(hydroxy-naphth-2-yl-methyl)-4-oxo-4H-pyridin-1-yl]-butyric acid

EXAMPLE 57

4-[3-Hydroxy-2-(hydroxy-naphth-2-yl-methyl)-4-oxo-4H-pyridin-1-yl]-butyric acid ethyl ester

EXAMPLE 58

4-(3-Hydroxy-naphth-2-ylmethyl-4-oxo-4H-pyridin-1-yl)-butyric acid ethyl ester

EXAMPLE 59

4-{Hydroxy-[3-hydroxy-1-(2-hydroxy-ethyl)-4-oxo-1,4-dihydro-pyridin-2-yl]-methyl}-benzamide 0.7 g of 4-{[3-benzyloxy-1-(2-hydroxy-ethyl)-4-oxo-1,4-dihydro-pyridin-2-yl]-hydroxy-methyl}-benzamide is hydrogenated in 20 ml of methanol over 0.07 g of palladium on carbon (5%) under normal pressure and at room temperature. The catalyst is removed by filtration and the product is recrystallised from methanol, yielding 4-{hydroxy-[3-hydroxy-1-(2-hydroxy-ethyl)-4-oxo-1,4-dihydro-pyridin-2-yl]-methyl}-benzamide in the form of colourless crystals. M.p.: 215.4°–216.5° C.

The starting material can be prepared, for example, as follows:

a) 4-[Hydroxy-(3-hydroxy-4-oxo-4H-pyran-2-yl)-methyl]-benzonitrile: From 11.2 g of pyroroeconic acid and 13.1 g of 4-cyanobenzaldehyde [GAS No.: 105-07-7] there is obtained analogously to Example 3a: 4-[hydroxy-(3-hydroxy-4-oxo-4H-pyran-2-yl)-methyl]-benzonitrile in the form of colourless crystals, m.p.: 164°–167° C.

b) 4-[(3-Benzyloxy-4-oxo-4H-pyran-2-yl)-hydroxy-methyl]-benzonitrile: Reaction of 23.3 g of 4-[hydroxy-(3-hydroxy-4-oxo-4H-pyran-2-yl)-methyl]-benzonitrile with benzyl bromide in N,N-dimethylformamide and potassium carbonate analogously to Example 1a yields 4-[(3-benzyloxy-4-oxo-4H-pyran-2-yl)-hydroxy-methyl]-benzonitrile. Light-yellow crystals, m.p.: 134.9°–137.8° C.

c) 4-[(3-Benzyloxy-4-oxo-4H-pyran-2-yl)-(tetrahydro-pyran-2-yloxy)-methyl]-benzonitrile: Reaction of 26.8 g of 4-[(3-benzyloxy-4-oxo-4H-pyran-2-yl)-hydroxy-methyl]-benzonitrile with 3,4-dihydro-2H-pyran analogously to Example 1b, followed by chromatography, yields 4-[(3-benzyloxy-4-oxo-4H-pyran-2-yl)-(tetrahydro-pyran-2-yloxy)-methyl]-benzonitrile in the form of a diastereoisomeric mixture. $R_f$ value 0.42 (silica gel 60, hexane/ethyl acetate1/1).

d) 4-[[3-Benzyloxy-1-(2-hydroxy-ethyl)-4-oxo-1,4-dihydro-pyridin-2-yl]-(tetrahydro-pyran-2-yloxy)-methyl]-benzamide: 4.17 g of 4-[(3-benzyloxy-4-oxo-4H-pyran-2-yl)-(tetrahydro-pyran-2-yloxy)-methyl]-benzonitrile are boiled under reflux for 140 hours in 40 ml of ethanol and 4.2 ml of ethanolamine. Working-up analogously to Example 1c and chromatography yield 4-[[3-benzyloxy-1-(2-hydroxy-ethyl)-4-oxo-1,4-dihydro-pyridin-2-yl]-(tetrahydro-pyran-2yl-oxy)-methyl]-benzamide in the form of a yellow resin. $R_f$ value: 0.4 (silica gel 60, dichloro-methane/ethanol 4/1).

e) 4-{[3-Benzyloxy-1-(2-hydroxy-ethyl)-4-oxo-1,4-dihydro-pyridin-2-yl]-hydroxy-methyl}-benzamide: 1.7 g of 4-[[3-benzyloxy-1-(2-hydroxy-ethyl)-4-oxo-1,4-dihydro-pyridin-2-yl]-(tetrahydro-pyran-2-yloxy)-methyl]-benzamide are boiled under reflux for 90 minutes in 5 ml of methanol and 3.7 ml of 2N hydrochloric acid. For working-up, the methanol is removed using a rotary evaporator. The residue is diluted with 50 ml of water, covered with 20 ml of ethyl acetate and neutralised with 3.7 ml of 2N sodium hydroxide solution. The resulting product is filtered off and washed with water and ethyl acetate. Drying yields 4-{[3-benzyl-oxy-1-(2-hydroxy-ethyl)-4-oxo-1,4-dihydro-pyridin-2-yl]-hydroxy-methyl}-benzamide in the form of colourless crystals. M.p.: 132°–137° C.

EXAMPLE 60

4-{Hydroxy-[3-hydroxy-1-(2-hydroxy-ethyl)-4-oxo-1,4-dihydro-pyridin-2-yl]-methyl}-benzonitrile

EXAMPLE 61

3-Hydroxy-1-(2-hydroxy-ethyl)-2-(4-methyl-benzyl)-1H-pyridin-4-one

At room temperature, 1.18 g of acetic acid 2-[3-hydroxy-2-(4-methyl-benzyl)-4-oxo-4H-pyridin-1-yl]-ethyl ester are dissolved in 3 ml ol methanol, and 3 ml of 2N sodium hydroxide solution are added. The solution is stirred at room temperature for 18 hours and then neutralised with 3 ml of 2N hydrochloric acid. The methanol is removed using a rotary evaporator and the resulting product is filtered. Drying yields: 3-hydroxy-1-(2-hydroxy-ethyl)-2-(4-methylbenzyl)-1H-pyridin-4-one in the form of colourless crystals, m.p.: 217°–219° C.

The starting material can be prepared, for example, as follows:

a) Acetic acid [1-(2-acetoxy-ethyl)-3-benzyloxy-4-oxo-1,4-dihydropyridin-2-yl]-p-tolyl-methyl ester: At room temperature, 3.46 g of 3-benzyloxy-1-(2-hydroxy-ethyl)-2-(hydroxy-p-tolyl-methyl)-1H-pyridin-4-one (Example 32e) are suspended in 35 ml of dichloromethane. 5.7 ml of triethylamine and 2.35 ml of acetic anhydride are added. After the addition of 0.05 g of 4-dimethylaminopyridine [CAS-No.: 1122-58-3], the reaction mixture is stirred at room temperature for 18 hours. 2 ml of ethanol are added and stirring is carried out at room temperature for 30 minutes. For working-up, the reaction mixture is washed once with 10 ml of 2N hydrochloric acid and three times with 10 ml of water. The aqueous phases are back-extracted once with 20 ml of dichloromethane. The combined organic phases are dried over magnesium sulfate and filtered. The flitrate is concentrated by evaporation using a rotary evaporator, yielding crude acetic acid [1-(2-acetoxy-ethyl)-3-benzyloxy-4-oxo-1,4-dihydro-pyridin-2-yl]-p-tolyl-methyl ester in the form of a beige resin. $R_f$ value 0.7 on silica gel 60 in the eluant dichloromethane/ethanol 4/1).

b) Acetic acid 2-[3-hydroxy-2-(4-methyl-benzyl)-4-oxo-4H-pyridin-1-yl]-ethyl ester: 4.1 g of acetic acid [1-(2-acetoxy-ethyl)-3-benzyloxy-4-oxo-1,4-dihydropyridin-2-yl]-p-tolyl-methyl ester are hydrogenated in 100 ml of tetrahydrofuran over 0.4 g of palladium on carbon (5%) at 50° C. and under normal pressure until 2 mol of $H_2$ per mol of $H_2$ starting material have been taken up. Filtering off the catalyst and concentrating the flitrate yield acetic acid 2-[3-hydroxy-2-(4-methyl-benzyl)-4-oxo-4H-pyridin-1-yl]-ethyl ester. Colourless crystals, m.p.: 205°–206.3° C.

EXAMPLE 62

4-[3-Hydroxy-2-(hydroxy-p-tolyl-methyl)-4-oxo-4H-pyridin-1-yl]-butyric acid

EXAMPLE 63

4-[3-Hydroxy-2-(hydroxy-p-tolyl-methyl)-4-oxo-4H-pyridin-1-yl]-butyric acid ethyl ester

EXAMPLE 64

4-[3-Hydroxy-2-(4-methyl-benzyl)-4-oxo-4H-pyridin-1-yl]-butyric acid ethyl ester

EXAMPLE 65

(+)-3-Hydroxy-1-(2-hydroxy-ethyl)-2-(hydroxy-phenyl-methyl)-1H-pyridin-4-one

Hydrogenation of 0.278 g of (+)-3-benzyloxy-1-(2-hydroxy-ethyl)-2-(hydroxy-phenyl-methyl)-1H-pyridin-4-one analogously to Example 1 yields (+)3-hydroxy-1-(2-hydroxy-ethyl)-2-(hydroxy-phenyl-methyl)-1H-pyridin-4-one. Colourless crystals, m.p.: 169°–170° C., $[\alpha]_D$=358°. (c=1% in methanol).

The starting material can be prepared, for example, as follows:

a) (+)-Acetic acid [1-(2-acetoxy-ethyl)-3-benzyloxy-4-oxo-1,4-dihydropyridin-2-yl-methyl]-phenyl-methyl ester: Racemic acetic acid [1-(2-acetoxy-ethyl)-3-benzyloxy-4-oxo-1,4-dihydropyridin-2-yl-methyl]-phenyl-methyl ester (Example 43a) is chromatographed on a column containing a chiral support, such as Chiralcel OD. Hexane/ethanol in a ratio of 8/2 is used as eluant. The first non-polar fraction eluted is (+)-acetic acid [1-(2-acetoxy-ethyl)-3-benzyloxy-4-oxo-1,4-dihydropyridin-2-yl-methyl]-phenyl-methyl ester. Yellow resin, $[\alpha]_D$=104° (c=1% in methanol).

b) (+)-3-Benzyloxy-1-(2-hydroxy-ethyl)-2-(hydroxy-phenyl-methyl)-1H-pyridin-4-one: 0.5 g of (+)-acetic acid [1-(2-acetoxy-ethyl)-3-benzyloxy-4-oxo-1,4-dihydropyridin-2-yl-methyl]-phenyl-methyl ester are dissolved in 5 ml of a 6M solution of ammonia in methanol and stirred at room temperature for 5 hours. The reaction solution is concentrated to dryness by evaporation using a rotary evaporator and the residue is stirred with ether. Filtering and drying yield (+)-3-benzyloxy-1-(2-hydroxy-ethyl)-2-(hydroxy-phenyl-methyl)-1H-pyridin-4-one in the form of colourless crystals. M.p.: 222°–224.6° C., $[\alpha]_D$=+277° (c=1% in methanol).

EXAMPLE 66

(−)-3-Hydroxy-1-(2-hydroxy-ethyl)-2-(hydroxy-phenyl-methyl)-1H-pyridin-4-one

Hydrogenation of 5.98 g of (−)-3-benzyloxy-1-(2-hydroxy-ethyl)-2-(hydroxy-phenyl-methyl)-1H-pyridin-4-one analogously to Example 1 yields (−)-3-hydroxy-1-(2-hydroxy-ethyl)-2-(hydroxy-phenyl-methyl)-1H-pyridin-4-one. Colourless crystals, m.p.: 168°–170° C., $[\alpha]_D$=−352° (c=1% in methanol).

The starting material can be prepared, for example, as follows:

a) (−)-Acetic acid [1-(2-acetoxy-ethyl)-3-benzyloxy-4-oxo-1,4-dihydropyridin-2-yl-methyl]-phenyl-methyl ester: From racemic acetic acid [1-(2-acetoxy-ethyl)-3-benzyloxy-4-oxo-1,4-dihydropyridin-2-yl-methyl]-phenyl-methyl ester as in Example 65a. The more polar fraction yields (−)-acetic acid [1-(2-acetoxy-ethyl)-3-benzyloxy-4-oxo-1,4-dihydropyridin-2-yl-methyl]-phenyl-methyl ester. Yellow resin, $[\alpha]_D$=−100.5° (c=1% in methanol).

b) (−)-3-Benzyloxy-1-(2-hydroxy-ethyl)-2-(hydroxy-phenyl-methyl)-1H-pyridin-4-one: From 1.6 g of (−)-acetic acid [1-(2-acetoxy-ethyl)-3-benzyloxy-4-oxo-1,4-dihydropyridin-2-yl-methyl]-phenyl-methyl ester there is obtained analogously to Example 65b: (−)-3-benzyloxy-1-(2-hydrooxy-ethyl)-2-(hydroxy-phenyl-methyl)-1H-pyridin-4-one in the form of colourless crystals. M.p.: 223°–225.5° C., $[\alpha]_D$=−272° (c=1% in methanol).

EXAMPLE 67

Acetic acid 2-[2-(4-fluoro-benzoyl)-3-hydroxy-4-oxo-4H-pyridin-1-yl]-ethyl ester

EXAMPLE 68

2-[(4-Fluorophenyl)-hydroxy-methyl]-3-hydroxy-1-methyl-1H-pyridin-4-one

EXAMPLE 69

2-(4-Fluorobenzyl)-3-hydroxy-1-methyl-1H-pyridin-4-one

EXAMPLE 70

2-(4-Fluoro-benzoyl)-3-hydroxy-1-(2-hydroxy-ethyl)-1H-pyridin-4-one

Treatment of 3-benzyloxy-2-(4-fluoro-benzoyl)-1-(2-hydroxy-ethyl)-1H-pyridin-4-one with conc. hydrochloric acid analogously to Example 34 yields 2-(4-fluoro-benzoyl)-3-hydroxy-1-(2-hydroxy-ethyl)-1H-pyridin-4-one. M.p.: 209°–216° C.

The starting material can be prepared, for example, as follows:

a) 3-Benzyloxy-2-(4-fluoro-benzoyl)-1-(2-hydroxy-ethyl)-1H-pyrdin-4-one: 3.69 g of 2-[(4-fluorophenyl)-hydroxy-methyl]-3-benzyloxy-1-(2-hydroxy-ethyl)-1H-pyridin-4-one are dissolved in 95 ml of acetonitrile, and 7.85 g of sodium percarbonate [CAS No.: 15630-89-4], 0.37 g of pyridinium dichromate [CAS No.: 20039-37-6] and 0.4 g of Aliquat 336 [CAS No.: 5137-55-3] are added. With vigorous stirring, the reaction mixture is heated under reflux for hours and the suspension is then concentrated to dryness by evaporation. Water is added to the residue and the product is extracted with ethyl acetate. Recrystallisation from ethyl acetate yields 3-benzyloxy-2-(4-fluoro-benzoyl)-1-(2-hydroxy-ethyl)-1H-pyridin-4-one. M.p.: 182°–182.6° C.

EXAMPLE 71

Acetic acid 2-[3-hydroxy-2-(4-fluorobenzyl)-4-oxo-4H-pyridin-1-yl]-ethyl

Hydrogenation of 6.2 g of acetic acid [1-(2-acetoxy-ethyl)-3-benzyloxy-4-oxo-1,4-dihydro-pyridin-2-yl]-(4-fluorophenyl)-methyl ester analogously to Example 61b yields acetic acid 2-[3-hydroxy-2-(4-fluorobenzyl)-4-oxo-4H-pyridin-1-yl]-ethyl ester in the form of colourless crystals, m.p.: 118°–119° C.

The starting material can be prepared, for example, as follows:

a) Acetic acid [1-(2-acetoxy-ethyl)-3:benzyloxy-4-oxo-1,4-dihydropyridin-2-yl]-(4-fluorophenyl)-methyl ester: From 4.7 g of 2-[(4-fluorophenyl)-hydroxy-methyl]-3-benzyloxy-1-(2-hydroxy-ethyl)-1H-pyridin-4-one (Example 3e) there is obtained analogously to Example 61a: acetic acid [1-(2-acetoxy-ethyl)-3-benzyloxy-4-oxo-1,4-dihydropyridin-2-yl]-(4-flurophenyl)-methyl ester in the form of a colourless resin. R$_f$ value: 0.48 (silica gel 60, ethyl acetate/ethanol 9/1).

EXAMPLE 72

3-Hydroxy-1-(2-hydroxy-ethyl)-2-(4-fluorobenzyl)-1H-pyridin-4-one 2.0 g of acetic acid 2-[3-hydroxy-2-(4-fluorobenzyl)-4-oxo-4H-pyridin-1-yl]-ethyl ester dissolved in 20 ml of methanol, and 5 ml of a 6M solution of ammonia in methanol are added. The reaction solution is stirred at room temperature for 18 hours, the product precipitating in the form of a thick crystal mass. Filtering, washing with methanol and drying yield 3-hydroxy-1-(2-hydroxy-ethyl)-2-(4-fluorobenzyl)-1H-pyridin-4-one in the form of colourless crystals. M.p.: 225°–231° C., decomp. from 190° C.

EXAMPLE 73

2-(4-Fluoro-benzoyl)-pyridine-3,4-diol

Hydrogenation of 0.88 g of (3-benzyloxy-4-hydroxy-pyridin-2-yl)-(4-fluorophenyl)-methanone analogously to Example 1, and recrystallisation, yield 2-(4-fluoro-benzoyl)-pyridine-3,4-diol in the form of reddish crystals. M.p.: 249°–251 ° C. with decomposition.

The starting material can be prepared, for example, as follows:

a) 3-Benzyloxy-2-[(4-fluorophenyl)-(tetrahydro-pyran-2-yloxy)-methyl]-pyridin-4-ol: Reaction of 3-benzyloxy-2-[(4-fluorophenyl)-(tetrahydro-pyran-2-yloxy)-methyl]-pyran-4-one (Example 3c) with ammonia analogously to Example 21a yields 3-benzyloxy-2-[(4-fluorophenyl)-(tetrahydro-pyran-2-yloxy)-methyl]-pyridin-4-ol. Resin. R$_f$ value: 0.62 (silica gel 60, dichloromethane/ethanol 4/1).

b) 3-Benzyloxy-2-[hydroxy-(4-fluorophenyl)-methyl]-pyridin-4-ol: Treatment of 3-benzyloxy-2-[(4-fluorophenyl)-(tetrahydro-pyran-2-yloxy)-methyl]-pyridin-4-ol analogously to Example 1d yields 3-benzyloxy-2-[hydroxy-(4-fluorophenyl)-methyl]-pyridin-4-ol. Colourless crystals, m.p.: 208°–213° C. with decomposition.

c) (3-Benzyloxy-4-hydroxy-pyridin-2-yl)-(4-fluorophenyl)-methanone: From 1.62 g of 3-benzyloxy-2-[hydroxy-(4-fluorophenyl)-methyl]-pyridin-4-ol there is obtained analogously to Example 70a, after chromatography, (3-benzyloxy-4-hydroxy-pyridin-2-yl)-(4-fluorophenyl)-methanone in the form of a greenish resin, R$_f$ value: 0.53 (silica gel 60, ethyl acetate/ethanol 6/1).

EXAMPLE 74

[2-(4-Fluorobenzyl)-3-hydroxy-4-oxo-4H-pyridin-1-yl]-acetic acid

Reddish crystals, m.p.: 233°–235° C., decomp. from 215° C.

EXAMPLE 75

[2-(4-Fluorobenzyl)-3-hydroxy-4-oxo-4H-pyridin-1-yl]-acetic acid ethyl ester

EXAMPLE 76

2-(4-Fluorobenzyl)-pyridine-3,4-diol:

Yellowish crystals, m.p.: 236°–240° C.; crystal transformation from 180° C., slow decomposition from 215° C.

EXAMPLE 77

2-(4-Fluorobenzyl)-3-hydroxy-1-(2-morpholin-4-yl-ethyl)-1H-pyridin-4-one

Colourless crystals, m.p.: 160.3°–1 61.2° C.

EXAMPLE 78

4-[2-(4-Fluorobenzyl)-3-hydroxy-4-oxo-4H-pyridin-1-ylmethyl]-benzoic acid

EXAMPLE 79

Acetic acid 2-[3-hydroxy-2-(4-methyl-benzyl)-4-oxo-4H-pyridin-1-yl]-ethyl

Colourless crystals, m.p.: 205°–206.3° C. Corresponds to Example 61b.

EXAMPLE 80

3-Hydroxy-1-(2-hydroxy-ethyl)-2-(4-chlorobenzyl)-1H-pyridin-4-one:

Beige crystals, m.p.: 222°–224° C., with decomposition.

EXAMPLE 81

Acetic acid 2-[3-hydroxy-2-(4-chlorobenzyl)-4-oxo-4H-pyridin-1-yl]-ethyl ester

EXAMPLE 82

3-Hydroxy-1-(2-hydroxy-ethyl)-2-(4-bromobenzyl)-1H-pyridin-4-one

EXAMPLE 83

Acetic acid [1-(2-acetoxy-ethyl)-3-hydroxy-4-oxo-1,4-dihydropyridin-2-yl]-(2-fluorophenyl)-methyl ester Hydrogenation of 2.15 g of acetic acid [1-(2-acetoxy-ethyl)-3-benzyloxy-4-oxo-1,4-dihydropyridin-2-yl]-(2- fluorophenyl)-methyl ester analogously to Example 1 yields acetic acid [1-(2-acetoxy-ethyl)-3-hydroxy-4-oxo-1,4-dihydropyridin-2-yl]-(2-fluorophenyl)-methyl ester. Colourless crystals, m.p.: 173°–174.5° C.

The starting material can be prepared, for example, as follows:

a) Acetic acid [1-(2-acetoxy-ethyl)-3-benzyloxy-4-oxo-1,4-dihydropyridin-2-yl]-(2-fluorophenyl)-methyl ester: Acetylation of 1.71 g of 2-[(2-fluorophenyl)-hydroxymethyl]-3-benzyloxy-1-(2-hydroxy-ethyl)-1Hopyridin-4-one (Example 49e) analogously to Example 61a yields crude acetic acid [1-(2-acetoxy-ethyl)-3-benzyloxy-4-oxo-1,4-dihydropyridin-2-yl]-(2-fluorophenyl)-methyl ester in the form of a beige resin. $R_f$ value: 0.27 (silica gel 60, ethyl acetate/ethanol 9/1).

EXAMPLE 84

Acetic acid 2-[3-hydroxy-2-(3-fluorobenzyl)-4-oxo-4H-pyridin-1-yl]-ethyl ester

Hydrogenation of 1.95 g of acetic acid [1-(2-acetoxy-ethyl)-3-benzyloxy-4-oxo-1,4-dihydropyridin-2-yl]-(3-fluorophenyl)-methyl ester analogously to Example 61b yields acetic acid 2-[3-hydroxy-2-(3-fluorobenzyl)-4-oxo-4H-pyridin-1-yl]-ethyl ester in the form of colourless crystals, m.p.: 147.9°–149.3° C.

The starting material can be prepared, for example, as follows:

a) Acetic acid [1-(2-acetoxy-ethyl)-3-benzyloxy-4-oxo-1,4-dihydropyridin-2-yl]-(3-fluorophenyl)-methyl ester: Acetylation of 1.67 g of 2-[(3-fluorophenyl)-hydroxymethyl]-3-benzyloxy-1-(2-hydroxy-ethyl)-1H-pyridin-4-one (Example 49e) analogously to Example 61a yields crude acetic acid [1-(2-acetoxy-ethyl)-3-benzyloxy-4-oxo-1,4-dihydropyridin-2-yl]-(3-fluorophenyl)-methyl ester. $R_f$ value: 0.37 (silica gel 60, ethyl acetate/ethanol 9/1).

EXAMPLE 85

3-Hydroxy-1-(2-hydroxy-ethyl)-2-(3-fluorobenzyl)-1H-pyridin-4-one

From 0.702 g of acetic acid 2-[3-hydroxy-2-(3-fluorobenzyl)-4-oxo-4H-pyridin-1-yl]-ethyl-ester (Example 84) there is obtained analogously to Example 72: 3-hydroxy-1-(2-hydroxy-ethyl)-2-(3-fluorobenzyl)-1H-pyridin-4-one in the form of colourless crystals, m.p.: 235°–242° C., slow decomposition from 204° C.

EXAMPLE 86

3-Hydroxy-1-(2-hydroxy-ethyl)-2-(hydroxy-thiophen-2-yl-methyl)-1H-pyridin-4-one

Hydrogenation of 0.952 g of 3-benzyloxy-1-(2-hydroxy-ethyl)-2-(hydroxy-thiophen-2-yl-methyl)-1H-pyridin-4-one analogously to Example 1, and chromatography, yield: 3-hydroxy-1-(2-hydroxy-ethyl)-2-(hydroxy-thiophen-2-yl-methyl)-1H-pyridin-4-one. M.p.: 186.9°–187.3° C.

The starting material can be prepared, for example, as follows:

a) 3-Hydroxy-2-(hydroxy-thiophen-2-yl-methyl)-pyran-4-one: From 5.6 g of pyromeconic acid and 5.6 g of thiophene-2-carbaldehyde [CAS No.: 98-03-3] there is obtained analogously to Example 3a: 3-hydroxy-2-(hydroxy-thiophen-2-yl-methyl)-pyran-4-one in the form of yellowish crystals, m.p.: from 144° C. with decomposition.

b) 3-Benzyloxy-2-(hydroxy-thiophen-2-yl-methyl)-pyran-4-one: Reaction of 4.39 g of 3-hydroxy-2-(hydroxy-thiophen-2-yl-methyl)-pyran-4-one with benzyl bromide in N,N-dimethylformamide and potassium carbonate analogously to Example 1 a yields 3-benzyloxy-2-(hydroxy-thiophen-2-yl-methyl)-pyran-4-one. Yellowish crystals, m.p.: 114.8°–117° C.

c) 3-Benzyloxy-2-[(tetrahydro-pyran-2-yloxy)-thiophen-2-yl-methyl]-pyran-4-one: Reaction of 4.3 g of 3-benzyloxy-2-(hydroxy-thiophen-2-yl-methyl)-pyran-4-one with 3,4-dihydro-2H-pyran analogously to Example 1b, and chromatography, yield 3-benzyloxy-2-[(tetrahydro-pyran-2-yloxy)-thiophen-2-yl-methyl]-pyran-4-one in the form of a diastereoisomeric mixture. $R_f$ value 0.28 (silica gel 60, hexane/ethyl acetate 2/1).

d) 3-Benzyloxy-1-(2-hydroxy-ethyl)-2-[(tetrahydro-pyran-2-yloxy)-thiophen-2-yl-methyl]-1H-pyridin-4-one: Reaction of 4.0 g of 3-benzyloxy-2-[(tetrahydro-pyran-2-yloxy)-thiophen-2-yl-methyl]-pyran-4-one with ethanolamine analogously to Example 1c, and chromatography, yield 3-benzyloxy-1-(2-hydroxy-ethyl)-2-[(tetrahydro-pyran-2-yloxy)-thiophen-2-yl-methyl]-1H-pyridin-4-one in the form of a brown resin. $R_f$ value: 0.24 (silica gel 60, ethyl acetate/ethanol 9/1).

e) 3-Benzyloxy-1-(2-hydroxy-etbyl)-2-(hydroxy-thiophen-2-yl-methyl)-1H-pyridin-4-one: 1.88 g of 3-benzyloxy-1-(2-hydroxy-ethyl)-2-[(tetrahydro-pyran-2-yloxy)-thiophen-2-yl-methyl]-1H-pyridin-4-one are boiled under reflux for 90 minutes in 7 ml of methanol and 4.25 ml of 2N hydrochloric acid. For working-up, the methanol is removed using a rotary evaporator. The residue is diluted with 20 ml of water and covered with 20 ml of ethyl acetate. Then, with stirring, 10 ml of saturated sodium hydrogen carbonate solution are added. The resulting product is filtered off and washed with water and ethyl acetate. Drying yields 3-benzyloxy-1-(2-hydroxy-ethyl)-2-(hydroxy-thiophen-2-yl-methyl)-1H-pyridin-4-one in the form of colourless crystals. M.p.: 193.8°–196° C.

EXAMPLE 87

9-Hydroxy-1-(4-methylthio-phenyl)-3,4-dihydro-1H-pyrido[2,1-c][1,4]oxazin-8-one hydrochloride 5.99 g of 3-benzyloxy-1-(2-hydroxy-ethyl)-2-[hydroxy-(4-methylthio-phenyl)-methyl]-1H-pyridin-4-one are boiled under reflux for 45 minutes in 60 ml of 6N hydrochloric acid. The reaction mixture is cooled to room temperature and covered with 10 ml of ethyl acetate. With vigorous stirring, the reaction mixture is neutralised with dilute sodium hydroxide solution until the product precipitates in the form of crystals. The reaction mixture is left to stand overnight in a refrigerator and then filtered. The crystals are washed with a small amount of cold alcohol. Drying yields 9-hydroxy-1-(4-methylthio-phenyl)-3,4-dihydro-1H-pyrido [2,1-c]-[1,4]oxazin-8-one hydrochloride, M.p.: 235°–238° C.

The starting material can be prepared, for example, as follows:

a) 3-Hydroxy-2-[hydroxy-(4-methylthio-phenyl)-methyl]-pyran-4-one: From 9.3 g of pyromeconic acid and 14 g of 4-(methylthio)-benzaldehyde [CAS No.: 3446-89-7] there is obtained analogously to Example 3a: 3-hydroxy-2-[hydroxy-(4-methylsulfanyl-phenyl)-methyl]-pyran-4-one in the form of beige crystals.

b) 3-Benzyloxy-2-[hydroxy-(4-methylthio-phenyl)-methyl]-pyran-4-one: Reaction of 16.6 g of 3-hydroxy-2-[hydroxy-(4-methylthio-phenyl)-methyl]-pyran-4-one with benzyl bromide in N,N-dimethylformamide and potassium carbonate analogously to Example 1a yields 3-benzyloxy-2-[hydroxy-(4-methylthio-phenyl)-methyl]-pyran-4-one. Yellowish crystals, m.p.: 82°–82.5° C.

c) 3-Benzyoxy-2-[(4-methylthiophenyl)-(tetrahydropyran-2-yoxy)-methyl]-pyran4-one: Reaction of 16.7 g of 3-benzyloxy-2-[hydroxy-(4-methylthio-phenyl)-methyl]-pyran-4-one with 3,4-dihydro-2H-pyran analogously to Example 1b yields crude 3-benzyloxy-2-[(4-methylthiophenyl)-(tetrahydro-pyran-2-yloxy)-methyl]-pyran-4-one in the form of a diastereoisomeric mixture. $R_f$ value 0.65 (silica gel 60, hexane/dichloromethanelethyl acetate 1/1/1).

d) 3-Benzyloxy-1-(2-hydroxy-ethyl)-2-[(4-methylthiophenyl)-(tetrahydro-pyran-2-yloxy)-methyl]-1H-pyridin-4-one: Reaction of 11.3 g of 3-benzyloxy-2-[(4omethylthio-phenyl)-(tetrahydro-pyran-2-yloxy)-methyl]-pyran-4-one with ethanolamine analogously to Example 1c, and chromatography, yield 3-benzyloxy-1-(2-hydroxy-ethyl)-2-[(4-methylthio-phenyl)-(tetra-hydro-pyran-2-yloxy)-methyl]-1H-pyridin-4-one. Yellow foam. $R_f$ value: 0.16 (silica gel 60, ethyl acetate/ethanol 9/1).

e) 3-Benzyloxy-1-(2-hydroxy-ethyl)-2-[hydroxy-(4-methylthio-phenyl)-methyl]-1H-pyridin-4-one: From 7.8 g of 3-benzyloxy-1-(2-hydroxy-ethyl)-2-[(4-methylthiophenyl)-(tetrahydro-pyran-2-yloxy)-methyl]-1H-pyridin-4-one there is obtained analogously to Example 1d: 3-benzyloxy-1-(2-hydroxy-ethyl)-2-[hydroxy-(4-methylthio-phenyl)-methyl]-1H-pyridin-4-one. M.p.: 120°–125° C.

EXAMPLE 88

9-Hydroxy-3-methoxy-1-phenyl-3, 4-dihydro-1H-pyrido[2,1-c][1,4]oxazin-8-one

Hydrogenation of 1.3 g of 9-benzyloxy-3-methoxy-1-phenyl-3,4-dihydro-1H-pyrido[2,1-c]-[1,4]oxazin-8-one analogously to Example 1 yields 9-hydroxy-3-methoxy-1-phenyl-3,4-dihydro-1H-pyrido[2,1-c][1,4]oxazin-8-one. Colourless crystals, m.p.: 201.7°–203.5° C.

The starting material can be prepared, for example, as follows:

a) 3-Benzyloxy-1-(2,2-dimethoxy-ethyl)-2-[phenyl-(tetrahydro-pyran-2-yloxy)-methyl]-1H-pyridin-4-one: 4.04 g of 3-benzyloxy-2-[phenyl-(tetrahydro-pyran-2-yloxy)-methyl]-pyran-4-one (Example 1c) are boiled under reflux for 45 hours in 40 ml of ethanol and 4 ml of 2-aminoacetaldehyde dimethyl acetal [CAS No.: 22483-09-6]. For working-up, the ethanol is removed using a rotary evaporator. The residue is taken up in 200 ml of ethyl acetate and washed three times with 50 ml of water each time. The organic phase is dried over magnesium sulfate and filtered. Concentration to dryness by evaporation using a rotary evaporator, and chromatography, yields 3-benzyloxy-1-(2,2-dimethoxy-ethyl)-2-[phenyl-(tetrahydropyran-2-yloxy)-methyl]-1H-pyridin-4-one in the form of a diastereoisomeric mixture. Orange resin, $R_f$ value: 0.45 (silica gel 60, ethyl acetate/ethanol 9/1).

b) 9-Benzyloxy-3-methoxy-1-phenyl-3,4-dihydro-1H-pyrido[2,1-c][1,4]oxazin-8-one: 2.13 g of 3-benzyloxy-1-(2,2-dimethoxy-ethyl)-2-[phenyl-(tetrahydro-pyran-2-yloxy)-methyl]-1H-pyridin-4-one are boiled under reflux for 2 hours in 5 ml of methanol and 8.8 ml of 2N hydrochloric acid. The methanol is distilled off using a rotary evaporator and the residue is diluted with water and neutralised with 8.8 ml of 2N sodium hydroxide solution. Extraction is carried out with ethyl acetate and the extracts are washed twice with water. The extracts are dried, filtered and concentrated by evaporation. Chromatography yields: 1.3 g of 9-benzyloxy-3-methoxy-1-phenyl-3,4-dihydro-1H-pyrido[2,1-c][1,4]oxazin-8-one in the form of a diastereoisomeric mixture. Yellow resin. $R_f$ value: 0.45 (silica gel 60, ethyl acetate/ethanol 9/1).

EXAMPLE 89

9-Hydroxy-1-phenyl-1H-pyrido[2,1-c][1,4]oxazine-3,8-dione

EXAMPLE 90

9-Hydroxy-1-thiophen-2-yl-3,4-dihydro-1H-pyrido[2,1-c][1,4]oxazin-8-one

From 3-benzyloxy-1-(2-hydroxy-ethyl)-2-(hydroxy-thiophen-2-yl-methyl)-1H-pyridin-4-one there is obtained analogously to Example 35: 9-hydroxy-1-thiophen-2-yl-3,4-dihydro-1H-pyrido[2,1-c][1,4]oxazin-8-one. Beige crystals, m.p.: 226°–229° C.

EXAMPLE 91

2-(Furan-2-yl-hydroxy-methyl)-3-hydroxy-1-(2-hydroxy-ethyl)-1H-pyridin-4-one

Colourless crystals, m.p.: 180°–182° C.

EXAMPLE 92

2-1Furan-2-yl-hydroxy-methyl)-3-hydroxy-1-methyl-1H-pyridin-4-one

EXAMPLE 93

1-Ethyl-3-hydroxy-2-(hydroxy-phenyl-methyl)-1H-pyridin-4-one

Colourless crystals, m.p.: 209°–216° C.

EXAMPLE 94

2-Benzylol-ethyl-3-hydroxy-1H-pyridin-4-one

Colourless crystals, m.p.: 179°–180° C.

EXAMPLE 95

N-(2-Hydroxy-ethyl)-2-[3-hydroxy-2-(hydroxy-phenyl-methyl)-4-oxo-4H-pyridin-1-yl]-acetamide Colourless crystals, m.p.: 177°–179° C.

EXAMPLE 96

1-Ethyl-2-[(4-flurophenyl)-hydroxy-methyl]-3-hydroxy-1H-pyridin-4-one

Colourless crystals, m.p.: 206°–209° C.

EXAMPLE 97

1-Ethyl-2-(4-fluorobenzyl)-3-hydroxy-1H-pyridin-4-one

Colourless crystals, m.p.: 170°–1 75° C.

EXAMPLE 98

[2-(4-fluorobenzyl)-3-hydroxy-4-oxo-4H-pyridin-1-yl]-acetic acid methyl ester

Colourless crystals, m.p.: 208°–212° C.

EXAMPLE 99

3-Hydroxy-2-(hydroxy-p-tolyl-methyl)-1-methyl-1H-pyridin-4-one

EXAMPLE 100

3-Hydroxy-1-methyl-2-(4-methylbenzyl)-1H-pyridin-4-one

EXAMPLE 101

2-[(4-Chlorophenyl)-hydroxy-methyl]-3-hydroxy-1-methyl-1H-pyridin-4-one

EXAMPLE 102

2-(4-Chlorobenzyl)-3-hydroxy-1-methyl-1H-pyridin-4-one

EXAMPLES A TO D

Pharmaceutical compositions

Hereinbelow, the term "active ingredient" is to be understood to denote a compound of formula I, in free form or in the form of a pharmaceutically acceptable salt, especially a compound that is described as a product in one of the above Examples.

Example A:

Tablets, each comprising 200 mg of active ingredient, can be prepared as follows:

| Composition (10000 tablets) | |
|---|---|
| active ingredient | 2000.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |
| ethanol | q.s. |

The active ingredient is mixed with the lactose and 292 g of the potato starch, and the mixture is moistened with an ethanolic solution of the gelatin and granulated through a sieve. After drying, the remainder of the potato starch, the magnesium stearate, the talc and the silicon dioxide are mixed in and the mixture is compressed to form tablets each weighing 295.0 mg and comprising 200 mg of active ingredient; if desired, the tablets may be provided with dividing notches for finer adaptation of the dose.

Example B:

Film-coated tablets, each comprising 400 mg of active ingredient, can be prepared as follows:

| Composition (1000 tablets) | |
|---|---|
| active ingredient | 400.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| dichloromethane | q.s. |

The active ingredient, the lactose and 40 g of the corn starch are mixed together, moistened with a paste prepared from 15 g of corn starch and water (with heating), and granulated. The granules are dried and the remainder of the corn starch, the talc and the calcium stearate are added and mixed with the granules. The mixture is compressed to form tablets which are then film-coated with a solution of the hydroxypropylmethylcellulose and the shellac in dichloromethane; final weight of the film-coated tablet: 583 mg.

Example C:

Hard gelatin capsules comprising 500 mg of active ingredient can be prepared, for example, as follows:

| Composition (for 1000 capsules): | |
|---|---|
| active ingredient | 500.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. The lactose is then added through a sieve of 0.6 mm mesh size and then the microcrystalline cellulose through a sieve of 0.9 mm mesh size. The mixture is then intimately mixed again for 10 minutes. Finally, the magnesium stearate is added through a sieve of 0.8 mm mesh size. After a further 3 minutes' mixing, 790 mg portions of the resulting formulation are introduced into hard gelatin capsules of a suitable size.

Example D:

An oral suspensible powder comprising 300 mg of active ingredient can be prepared, for example, as follows:

| Composition (1 dose): | |
|---|---|
| active ingredient | 300 mg |
| hydroxypropylcellulose (Klucel HF) | 50 mg |
| tartaric acid | 100 mg |
| sodium lauryl sulfate | 100 mg |

The sodium lauryl sulfate is added to the lyophilised active ingredient through a sieve of 0.2 mm mesh size. The two components are intimately mixed. The microcrystalline cellulose is then added through a sieve of 0.9 mm mesh size. The mixture is then intimately mixed again for 10 minutes. Finally, the tartaric acid is added through a sieve of 0.8 mm mesh size. After a further 3 minutes' mixing, the mixture is introduced into a container having a capacity of at least 10 ml. For use, the mixture is made up to 10 ml with water and shaken vigorously.

What is claimed is:

1. A compound of formula I $$\text{(I)}$$

$$R_3 \underset{\underset{R_2}{|}}{\overset{O}{\underset{N}{\bigcirc}}} \overset{OR_4}{\underset{A}{\overset{B}{\diagdown}}} R_1$$

wherein:

$R_1$ is hydrogen, halogen, substituted or unsubstituted lower alkyl or lower alkoxy, lower alkoxycarbonyl, amino, substituted or unsubstituted lower alkylamino or di-lower alkylamino, aminocarbonyl, substituted or unsubstituted N-lower alkylaminocarbonyl or N,N-di-lower alkylaminocarbonyl, carboxyl, lower alkylsulfonyl, aminosulfonyl, cyano, hydroxy, nitro, tetrazolyl, or lower alkylenedioxy which with the group B forms a heterocyclic oxygen-containing ring system;

$R_2$ is hydrogen, substituted or unsubstituted lower alkyl or lower alkylenehydroxy, substituted or unsubstituted lower alkylene-lower alkoxy, lower alkylenecarboxy, lower alkylenecarbonyl-lower alkoxy, substituted or unsubstituted lower alkyleneamine, substituted or unsubstituted N-lower alkanoyl-lower alkyleneamine, lower alkanoyloxy-lower alkylene, formyl-lower alkylene;

$R_3$ is hydrogen, substituted or unsubstituted lower alkyl, substituted or unsubstituted lower alkanoyloxy-lower alkylene, aminocarbonyl, substituted or unsubstituted N-lower alkylaminocarbonyl, N,N-di-lower alkylaminocarbonyl;

$R_4$ is hydrogen, lower alkanoyl, lower alkoxycarbonyl, or a radical that can be removed under physiological conditions;

A is substituted or unsubstituted methylene, carbonyl; and

B is mono- or poly-substituted or unsubstituted aryl or mono- or poly-substituted or unsubstituted heteroaryl;

or a stereoisomer, a tautomer or a salt thereof.

2. A compound according to claim 1, wherein $R_1$ is hydrogen, halogen, substituted or unsubstituted lower alkyl or lower alkoxycarbonyl, amino, lower alkylamino, di-lower alkylamino, aminocarbonyl, substituted or unsubstituted N-lower alkylaminocarbonyl or N,N-di-lower alkylaminocarbonyl, carboxyl, cyano, hydroxy, nitro, or lower alkylenedioxy which with the group B forms a heterocyclic oxygen-containing ring system;

$R_2$ is hydrogen, substituted or unsubstituted lower alkyl or lower alkylenehydroxy, substituted or unsubstituted lower alkylene-lower alkoxy, lower alkylenecarboxy, lower alkylenecarbonyl-lower alkoxy, substituted or unsubstituted lower alkyleneamine, substituted or unsubstituted N-lower alkanoyl-lower alkyleneamine;

$R_3$ is hydrogen, substituted or unsubstituted lower alkyl, carboxyl, substituted or unsubstituted lower alkanoyloxy-lower alkylene, substituted or unsubstituted N-lower alkyleneaminocarbonyl;

$R_4$ is hydrogen, lower alkanoyl, lower alkoxycarbonyl or a radical that can be removed under physiological conditions;

A is substituted or unsubstituted methylene, carbonyl; and

B is mono- or poly-substituted or unsubstituted aryl or mono-or poly-substituted or unsubstituted heteroaryl;

or a stereoisomer, a tautomer or a pharmaceutically acceptable salt thereof.

3. A compound according to claim 1, wherein $R_1$ is hydrogen, halogen, substituted or unsubstituted lower alkyl, substituted or unsubstituted lower alkoxy, cyano, hydroxy or nitro;

$R_2$ is substituted or unsubstituted lower alkyl, substituted or unsubstituted lower alkylenehydroxy or lower alkyleneamine;

$R_3$ is hydrogen;

$R_4$ is hydrogen, lower alkanoyl, lower alkoxycarbonyl or a radical that can be removed under physiological conditions;

A is substituted or unsubstituted methylene, carbonyl; and

B is mono-substituted or unsubstituted aryl or mono-substituted or unsubstituted heteroaryl; or a stereoisomer, a tautomer or a pharmaceutically acceptable salt thereof.

4. A compound according to claim 1, wherein $R_1$ is hydrogen, halogen or unsubstituted lower alkyl;

$R_2$ is substituted or unsubstituted lower alkyl, substituted or unsubstituted lower alkylenehydroxy;

$R_3$ and $R_4$ are hydrogen;

A is substituted or unsubstituted methylene; and

B is mono-substituted or unsubstituted aryl or mono-substituted or unsubstituted heteroaryl; or a stereoisomer, a tautomer or a pharmaceutically acceptable salt thereof.

5. A compound from the group consisting of 3-hydroxy-1-(2-hydroxy-ethyl)-2-(hydroxy-phenyl-methyl)-1H-pyridin-4-one;

3-hydroxy-1-(2-hydroxy-ethyl)-2-(4-methyl-benzyl)-1H-pyridin-4-one;

3-hydroxy-1-(2-hydroxy-ethyl)-2-(hydroxy-4-fluorophenyl-methyl)-1H-pyiidin-4-one;

3-hydroxy-1-(2-hydroxy-ethyl)-2-(4-fluorobenzyl)-1H-pyridin-4-one;

3-hydroxy-1-(2-hydroxy-ethyl)-2-(hydroxy-4-chlorophenyl-methyl)-1H-pyridin-4-one; and 3-hydroxy-1-(2-hydroxy-ethyl)-2-(4-chlorobenzyl)-1H-pyridin-4-one;

or a stereoisomer, a tautomer or a pharmaceutically acceptable salt thereof.

6. A pharmaceutical composition comprising a therapeutically effective amount of a compound of the formula I or a pharmaceutically acceptable salt thereof according to claim 1, together with a suitable carrier.

7. A pharmaceutical composition for oral administration comprising a pharmaceutical composition according to claim 6 wherein the carrier is suitable for oral uptake.

8. A method of treatment of pathological conditions in a mammal that are associated with an excess of iron ions in the body, comprising administering to said mammal a therapeutically effective amount of a compound of formula I or a pharmaceutically acceptable salt thereof according to claim 1.

9. A method according to claim 8 wherein the compound of formula I or a pharmaceutically acceptable salt thereof is administered orally.

10. A process for the preparation of a compound of formula I according to claim 1, or of a stereoisomer, a tautomer or a pharmaceutically acceptable salt thereof, which process comprises reacting a compound of formula II

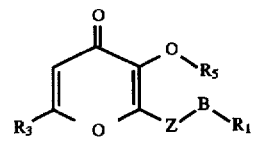

(II)

wherein $R_1$, $R_3$ and B are as defined for formula I, Z is unsubstituted or substituted methylene (substituents being, if necessary, in protected form) or carbonyl and $R_5$ has the same meaning as $R_4$ as defined for formula I or, if necessary, is a suitable protecting group, with a compound of formula III

(III)

wherein $R_2$ is as defined for formula I, to form a compound of formula IV

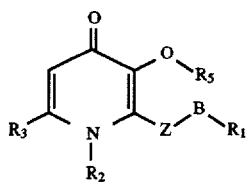

(IV)

wherein $R_1$, $R_2$, $R_3$, $R_5$, B and Z are as defined for formulae I and II, and converting that compound, a) if necessary by simultaneously removing a protecting group $R_5$ and a protecting group that may be present at the group Z, into a compound of formula I and, if desired, into a different compound of formula I, and/or, if desired, converting a resulting salt into the free compound or into a different salt, and/or, if desired, converting a resulting free compound of formula I having salt-forming properties into a salt, or b) if necessary after removing a protecting group $R_5$ or a protecting group that may be present at the group Z, first into a different protected form of a compound of formula I and, if desired, into a protected form of a different compound of formula I, and then, by removing the remaining protecting groups, into a compound of formula I, and, if desired, into a different compound of formula I, and/or, if desired, converting a resulting salt into the free compound or into a different salt, and/or, if desired, converting a resulting free compound of formula I having salt-forming properties into a salt.

* * * * *